US011739164B2

(12) United States Patent
Demirel et al.

(10) Patent No.: US 11,739,164 B2
(45) Date of Patent: Aug. 29, 2023

(54) COMPOSITIONS AND METHODS RELATED TO 2 DIMENSIONAL MOLECULAR COMPOSITES

(71) Applicant: The Penn State Research Foundation, University Park, PA (US)

(72) Inventors: Melik Demirel, State College, PA (US); Mert Vural, State College, PA (US); Mauricio Terrones, State College, PA (US); Yu Lei, State College, PA (US); Ibrahim Tarik Ozbolat, Boalsburg, PA (US)

(73) Assignee: The Penn State Research Foundation, University Park, PA (US)

( * ) Notice: Subject to any disclaimer, the term of this patent is extended or adjusted under 35 U.S.C. 154(b) by 1134 days.

(21) Appl. No.: 16/463,158

(22) PCT Filed: Dec. 14, 2017

(86) PCT No.: PCT/US2017/066380
§ 371 (c)(1),
(2) Date: May 22, 2019

(87) PCT Pub. No.: WO2018/140145
PCT Pub. Date: Aug. 2, 2018

(65) Prior Publication Data
US 2019/0352430 A1    Nov. 21, 2019

Related U.S. Application Data

(60) Provisional application No. 62/433,971, filed on Dec. 14, 2016.

(51) Int. Cl.
| C07K 17/14 | (2006.01) |
| B41M 5/00 | (2006.01) |
| C07K 1/04 | (2006.01) |
| B82Y 15/00 | (2011.01) |
| B82Y 40/00 | (2011.01) |

(52) U.S. Cl.
CPC ........... C07K 17/14 (2013.01); B41M 5/0011 (2013.01); C07K 1/042 (2013.01); B82Y 15/00 (2013.01);
(Continued)

(58) Field of Classification Search
CPC ...... C07K 17/14; C07K 1/042; B41M 5/0011; B82Y 15/00; B82Y 40/00; Y10S 977/705;
(Continued)

(56) References Cited

U.S. PATENT DOCUMENTS

2003/0108743 A1    6/2003    Anderson

OTHER PUBLICATIONS

Hu, Kesong, et al. "Ultra-robust graphene oxide-silk fibroin nanocomposite membranes." Advanced Materials 25.16 (2013): 2301-2307. (Year: 2013).*

(Continued)

*Primary Examiner* — Robert J Eom
(74) *Attorney, Agent, or Firm* — Hodgson Russ LLP

(57) ABSTRACT

Provided are compositions that include at least one two-dimensional layer of an inorganic compound and at least one layer of an organic compound in the form of one or more polypeptides. Methods of making and using the materials are provided. The organic layer contains one or more polypeptides, each of which have alternating repeats of crystallite-forming subsequences and amorphous subsequences. The crystallite-forming subsequences form crystallites comprising stacks of one or more beta-sheets. The amorphous subsequences form a network of hydrogen bonds. A method includes i) combining one or more polypeptides with an inorganic material and an organic solvent, and ii) depositing one or more polypeptides, the inorganic material and the organic solvent onto a substrate. These steps can be repeated to provide a composite material that is a multilayer composite material. The composite materials can be used in a (Continued)

wide array of textile, electronic, semi-conducting, and other applications.

21 Claims, 35 Drawing Sheets

Specification includes a Sequence Listing.

(52) U.S. Cl.
CPC ............ *B82Y 40/00* (2013.01); *Y10S 977/705* (2013.01); *Y10S 977/712* (2013.01); *Y10S 977/725* (2013.01); *Y10S 977/727* (2013.01); *Y10S 977/828* (2013.01)

(58) Field of Classification Search
CPC ............ Y10S 977/712; Y10S 977/725; Y10S 977/727; Y10S 977/828
See application file for complete search history.

(56) References Cited

OTHER PUBLICATIONS

Cheng, Yuan, et al. "Peptide-graphene interactions enhance the mechanical properties of silk fibroin." ACS Applied Materials & Interfaces 7.39 (2015): 21787-21796. (Year: 2015).*

Vozar, Steven, et al. "Automated spin-assisted layer-by-layer assembly of nanocomposites." Review of Scientific Instruments 80.2 (2009): 023903. (Year: 2009).*

Hu, Kesong. Ultra-robust graphene based bio-nanocomposites and their electronic applications. Diss. Georgia Institute of Technology, 2016. (Year: 2016).*

Wen, Hongxiu, et al. "Transgenic silkworms (*Bombyx mori*) produce recombinant spider dragline silk in cocoons." Molecular biology reports 37 (2010): 1815-1821. (Year: 2010).*

Wang, Fen, et al. "An organ-like titanium carbide material (MXene) with multilayer structure encapsulating hemoglobin for a mediator-free biosensor." Journal of the Electrochemical Society 162.1 (2014): B16. (Year: 2014).*

Brown, C.L., et al., Template-Directed Assembly of a de Novo Designed Protein, Journal of the American Chemical Society, May 23, 2002, vol. 124, pp. 6846-6848.

So, C.R., et al., Controlling Self-Assembly of Engineered Peptides on Graphite by Rational Mutation, ACS Nano, Feb. 28, 2012, vol. 6, No. 2, pp. 1648-1656.

Wang, X., et al., Nanolayer Biomaterial Coatings of Silk Fibroin for Controlled Release, Journal of Controlled Release, Aug. 28, 2007, vol. 121, No. 3, pp. 190-199.

Lvov, Y., et al., Assembly of Multicomponent Protein Films by Means of Electrostatic Layer-by-Layer Adsorption, Journal of the American Chemical Society, 1995, vol. 117, pp. 6117-6123.

* cited by examiner a  maaklitllavialsnyayall*P*GLLGG
YGY*P*AATTYRQTTHHGYGGLY
GGLGYHY*P*AATAVSHTTHHA*P*
[YGYGGLYGGLYGGLGY*P*AAAS
VSTVHH*P*]VGYGGYGLGAYGAY
GLGYGLHY*P*AATAVSHTTHHA
*P*YGYGGLYGGLYGGLGAVSTVS
HGLGYGLHH*P*VGYAGYGLGAT
AVSHTTHHA*P*YGGFGYGLY

YGYGGLYGGLYGGLGY*P*AAASVSTVHH*P* g)

h)

COMPOSITIONS AND METHODS RELATED TO 2 DIMENSIONAL MOLECULAR COMPOSITES

CROSS REFERENCE TO RELATED APPLICATIONS

This application claims priority to U.S. provisional application No. 62/433,971, filed Dec. 14, 2016, the disclosure of which is incorporated herein by reference.

STATEMENT REGARDING FEDERALLY SPONSORED RESEARCH

This invention was made with government support under Contract No. W911NF-16-1-0019 awarded by the Army Research Office. The government has certain rights in the invention.

FIELD OF THE DISCLOSURE

The present disclosure relates generally to compositions and methods for designing and using high 2D molecular composites with tunable distances between layers.

BACKGROUND OF THE DISCLOSURE

Graphene-based composites offer unique physical properties in materials synthesis and fabrication. Following the groundbreaking discovery of graphene, other 2D layered materials such as hexagonal boron nitride-hBN, layered oxides, metal dichalcogenides and metal carbides enchanted condensed matter community. Novel types of 2D hybrids have been built either by mixing organic/inorganic materials to control their arrangement and interlayer spacing (e.g. composites), or by layer-by-layer reassembling of 2D layered materials into heterostructures (e.g. van der Waals solids). These materials form the bases of new devices and multifunctional composites because 2D materials respond to physical cues strongly. Molecular composites will establish the foundation of next generation programmable, flexible, biocompatible, optically superior, energy efficient and mechanical strong materials and devices. For example, composites of carbon nanotubes with polymers show thermal actuation response in millisecond time and at low voltage (~1V). For practical applications, the strong mechanical actuations in 2D materials could be further enhanced by integrating them with molecular bio-organic composites such as bimorph structures. Such integration with biomorph structures will lead to significantly faster actuation and enhanced sensitivity in thermal sensitivity due to the molecular nature of these layers. Although previous work shows the synthesis of 2D composites using graphene oxide (GO) with h-bonded polymers (e.g., PMMA, PVA), polymers used in these studies lacked of supramolecular chemistry. The present disclosure provides improved 2D composites that comprise supramolecular chemistry and have utility in a wide array of products and processes.

SUMMARY

The present disclosure provides improved compositions of matter, and methods of making and using the same. In one approach the disclosure provides a method of making a composite material comprising at least one two-dimensional (2D) inorganic layer and an at least one organic layer. The organic layer comprises one or more polypeptides, each of which comprise alternating repeats of crystallite-forming subsequences and amorphous subsequences. The crystallite-forming subsequences form crystallites comprising stacks of one or more β-sheets. The amorphous subsequences form a network of hydrogen bonds. The method generally includes the steps of i) combining the one or more polypeptides with an inorganic material and an organic solvent, and ii) depositing the one or more polypeptides, the inorganic material and the organic solvent onto a substrate. These steps result in formation of at least one composite layer comprising the polypeptides and the inorganic material. The method optionally includes repeating i) and ii) to form the composite material that is a multilayer composite material. In embodiments the inorganic material comprises Graphene, Graphyne, Borophene, Germanene, Silicene, Stanene, Phosphorene, Molybdenite, Graphane Oxide (GO), Hexagonal boron nitride, a Germanane compound, a Methyl Oxide, a Methyl Carbide, a Methyl nitride, a transition metal oxide, a transition metal di-chalcogenide, or a combination thereof. In embodiments, the composites include heterostructures. In certain embodiments, the organic layer has a thickness of from 0.5 nm-10.0 nm. In embodiments, the crystallite-forming subsequence is from about 2 nm to about 5 nm long. In embodiments, the polypeptide comprises from 4 to 20 repeats of the crystallite-forming subsequences. In embodiments, a polypeptide that is present in the composite materials described herein comprises a sequence that exhibits crystallinity between 0% and 60%. In certain examples the amorphous subsequence comprises from 10 to 60 amino acids. In certain examples, a method comprises forming a multilayer composite material, which can have between 2 and $10^9$ composite layers, each of which includes an organic layer and an inorganic layer.

In certain approaches, depositing a combination of the polypeptides, the inorganic layer and the organic solvent onto a substrate comprises vacuum assisted self-assembly, or passing a combination of the polypeptides, the inorganic material and the organic solvent through a nozzle onto the substrate, including but not necessarily limited to depositing by printing, such as inkjet printing. In such cases, the printing droplets may have a diameter of from 50 to 70 μm, and/or the printing is such that lines are formed and have a minimum distance between one another of not less than 40 μm. The composite materials can comprise, consist essentially of, and consist of the polypeptides and the inorganic material, wherein consisting essentially of the polypeptides and the inorganic material provides for residual, trace amounts of other compositions of matter, such as the inorganic solvent and/or other impurities. Composite materials made by any method described herein are included. Such materials can be shaped in various three-dimensional objects, and can be coated onto any surface, including porous and non-porous surfaces that are described further below. In certain embodiments the composite material comprises an electronic conductor or semi-conductor. In certain embodiments the composite material can and does function as an actuator, which can be actuated so as to change its shape in response to a stimulus, such as a thermal and/or electrical stimulus. Methods for selecting materials for use in making composite materials described herein are provided, and take advantage in part of the numerous examples of polypeptides, as well as inorganic materials, that are provided herein, such that any of a wide variety of composite materials can be produced.

PAAAAAAAVHHP, (SEQ ID NO: 303)

PAAAPVAPVHHP; (SEQ ID NO: 304)

PAAASVSTVHHP; (SEQ ID NO: 305)

PAAAALPAVHHP; (SEQ ID NO: 306)

PAAAPLSTVHHP. (SEQ ID NO: 307)

Figure 2:
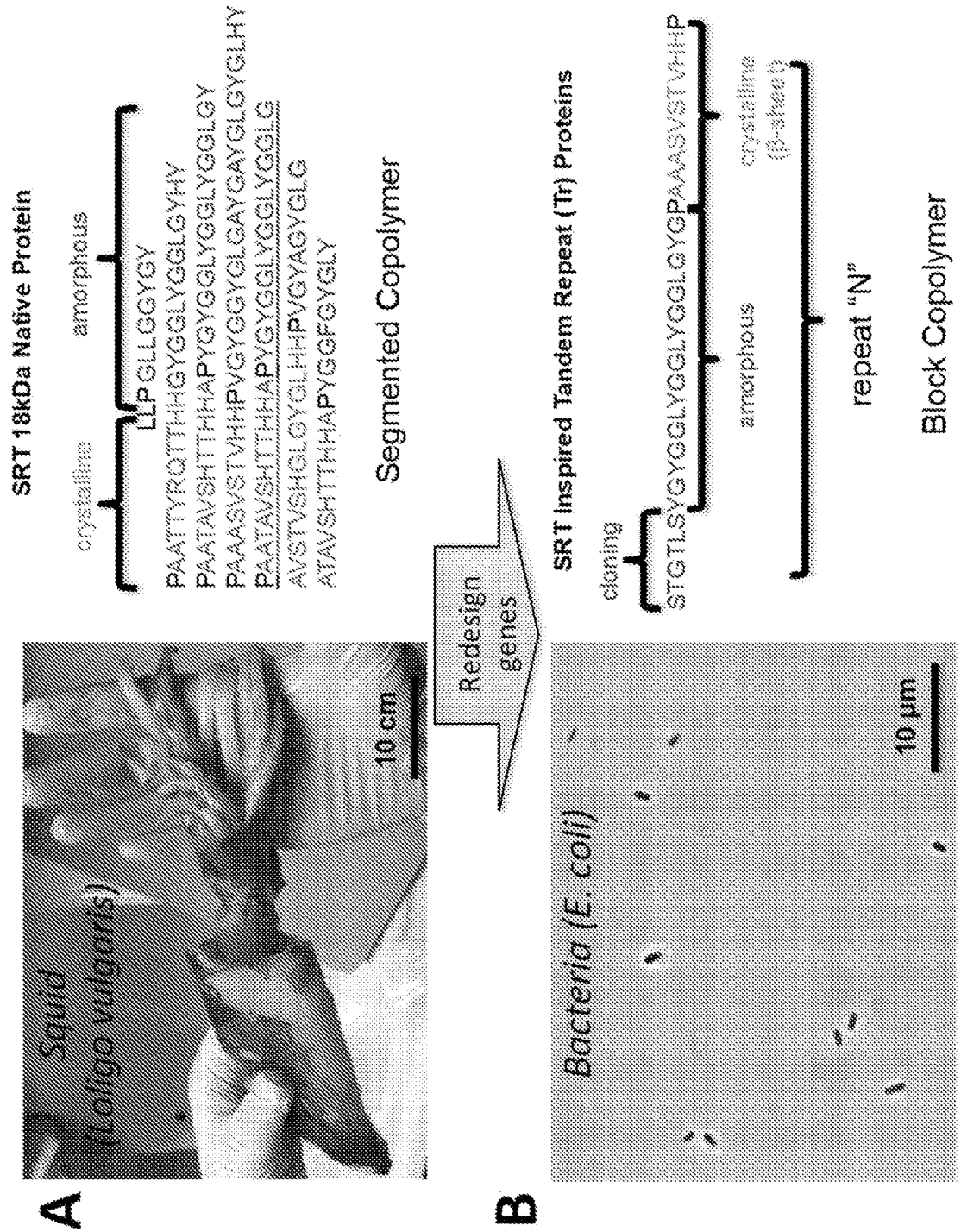
Figure 2:
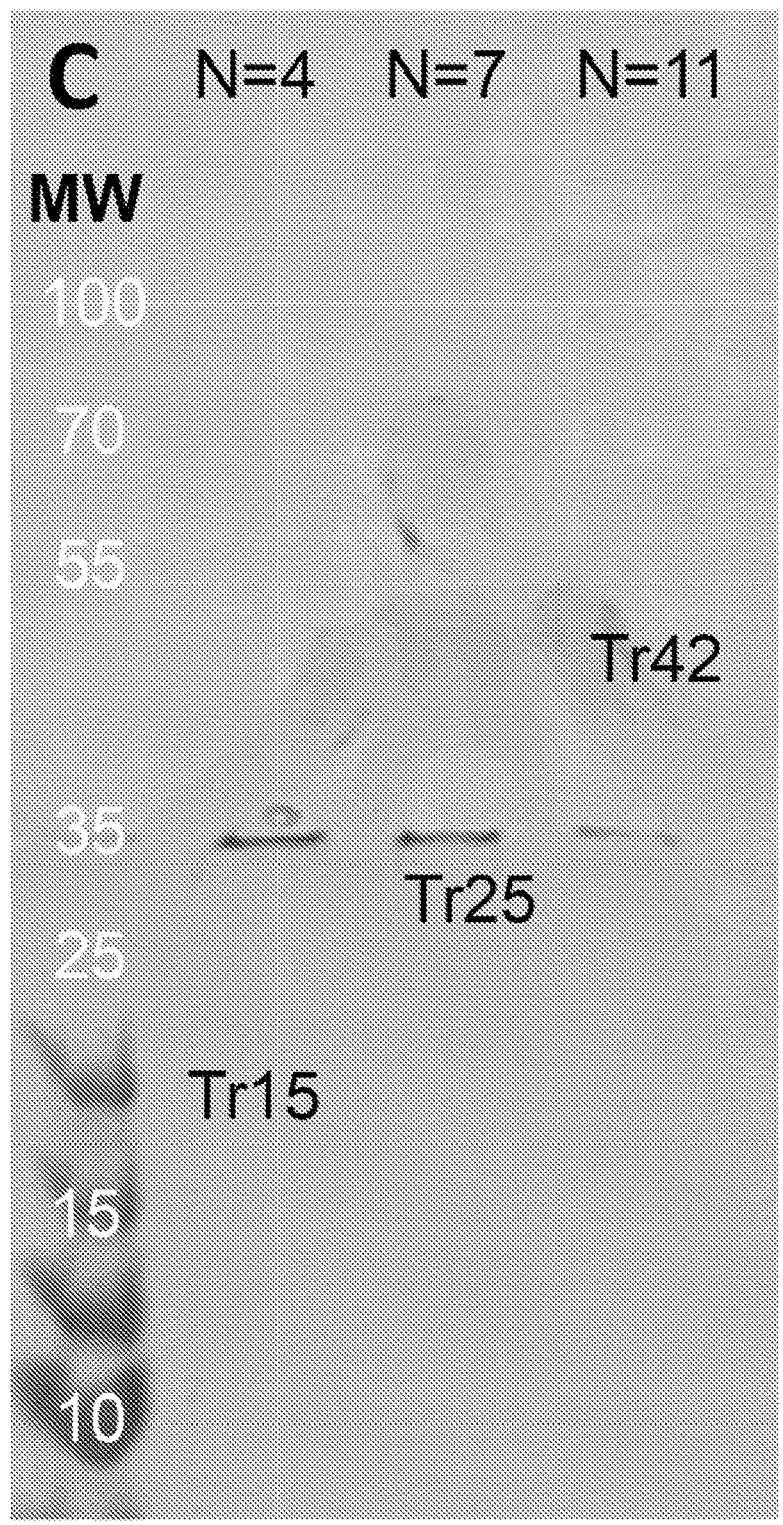

FIG. 2 shows A) Native Squid ring teeth (SRT) proteins are found in the tentacles of the squid suction cups. However these proteins show random segmented copolymer sequence with varying crystalline and amorphous domains. B) Engineered sequences of SRT inspired tandem repeat proteins, expressed in E. coli, have ordered block copolymer morphology, which is ideal for controlling interlayer distances of 2d-layered materials. C) SDS/Page gel chromatography identifying molecular weight values for three tandem repeat proteins (i.e., Tr15, Tr25, and Tr42) with specific repetitions of 4, 7, and 11 respectively.

Figure 3:
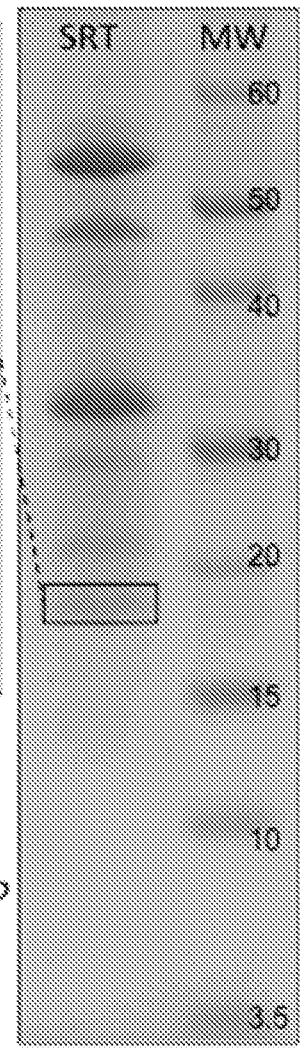
Figure 3:
Figure 3:
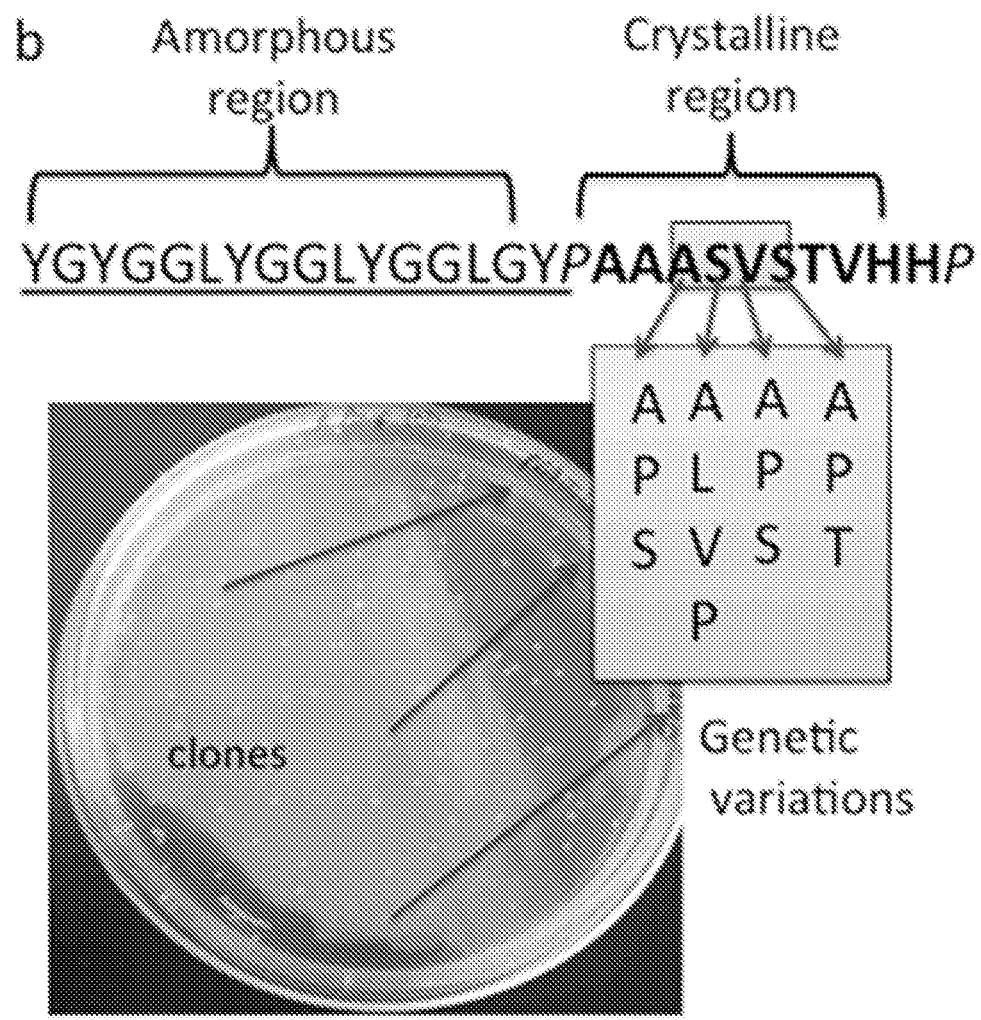
Figure 3:
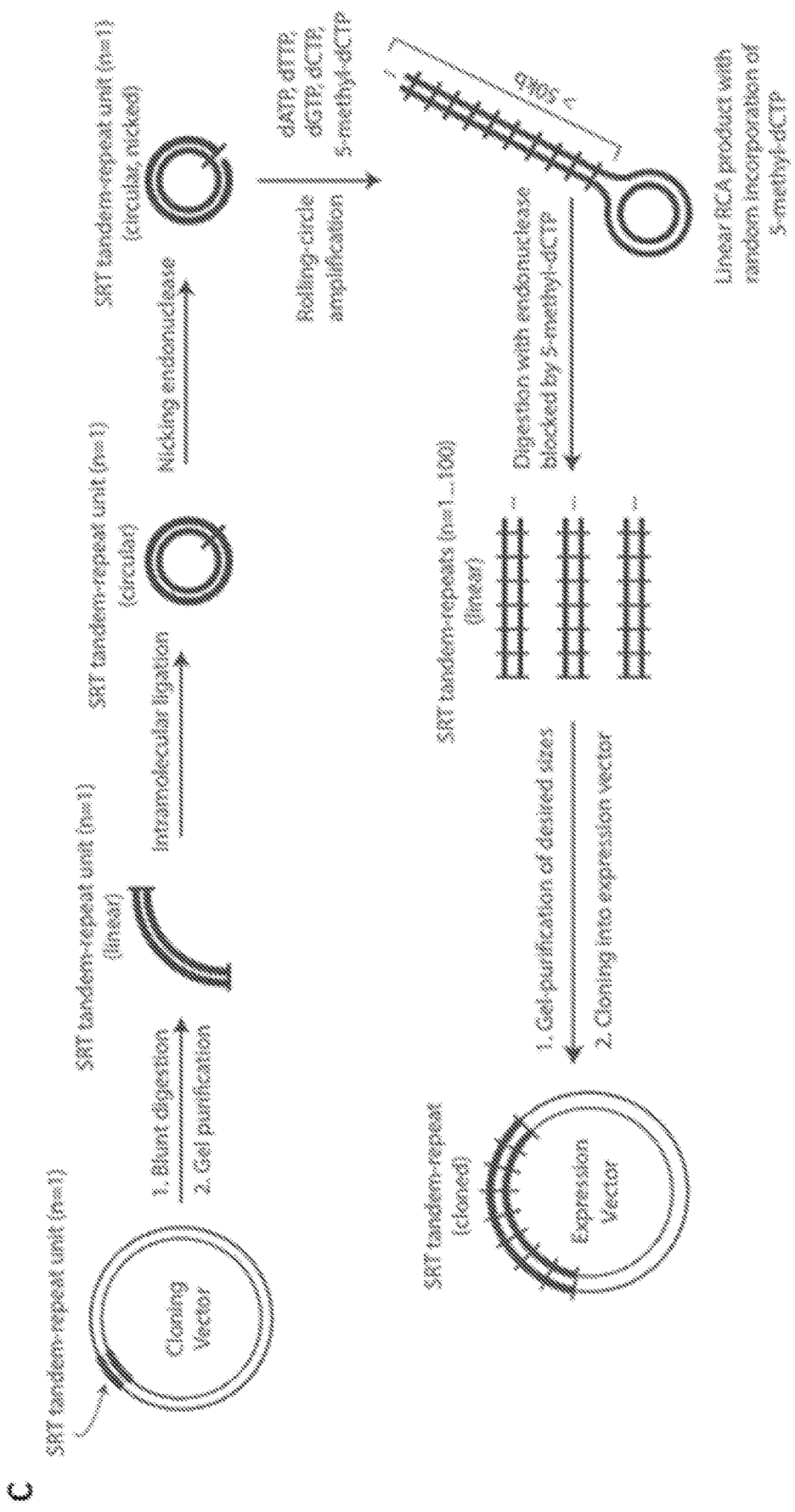
Figure 3:
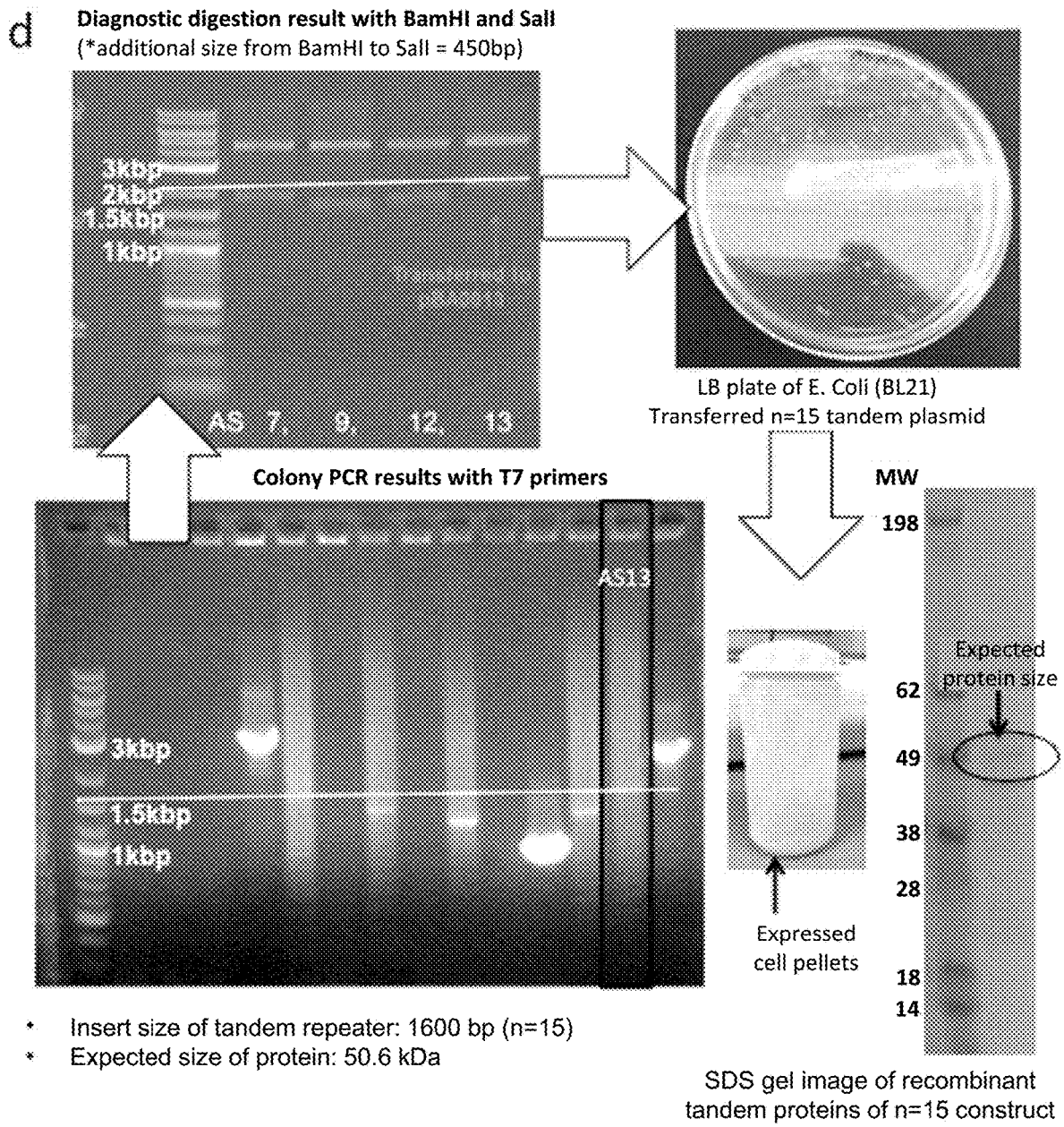

FIG. 3 shows (a) Segmented copolymer architecture of the protein sequence is marked as signal sequence: lower case, prolines: italics, amorphous: underlined, crystalline: bold, amorphous/crystalline: underlined and bold. The SDS-Page (middle) shows sizes of native SRT proteins. The 195 amino acid sequence is SEQ ID NO:303. The sequence YGYGGLYGGLYGGLGYPAAASVSTVHHP is SEQ ID NO:304. (b) The library is prepared based on the protein template of 18 kDa native sequence. (c) Tandem repeat construction strategy to control the length of synthetic protein. (d) Example of tandem repeat construction of N=13 with DNA and SDS-page gels.

Figure 4:
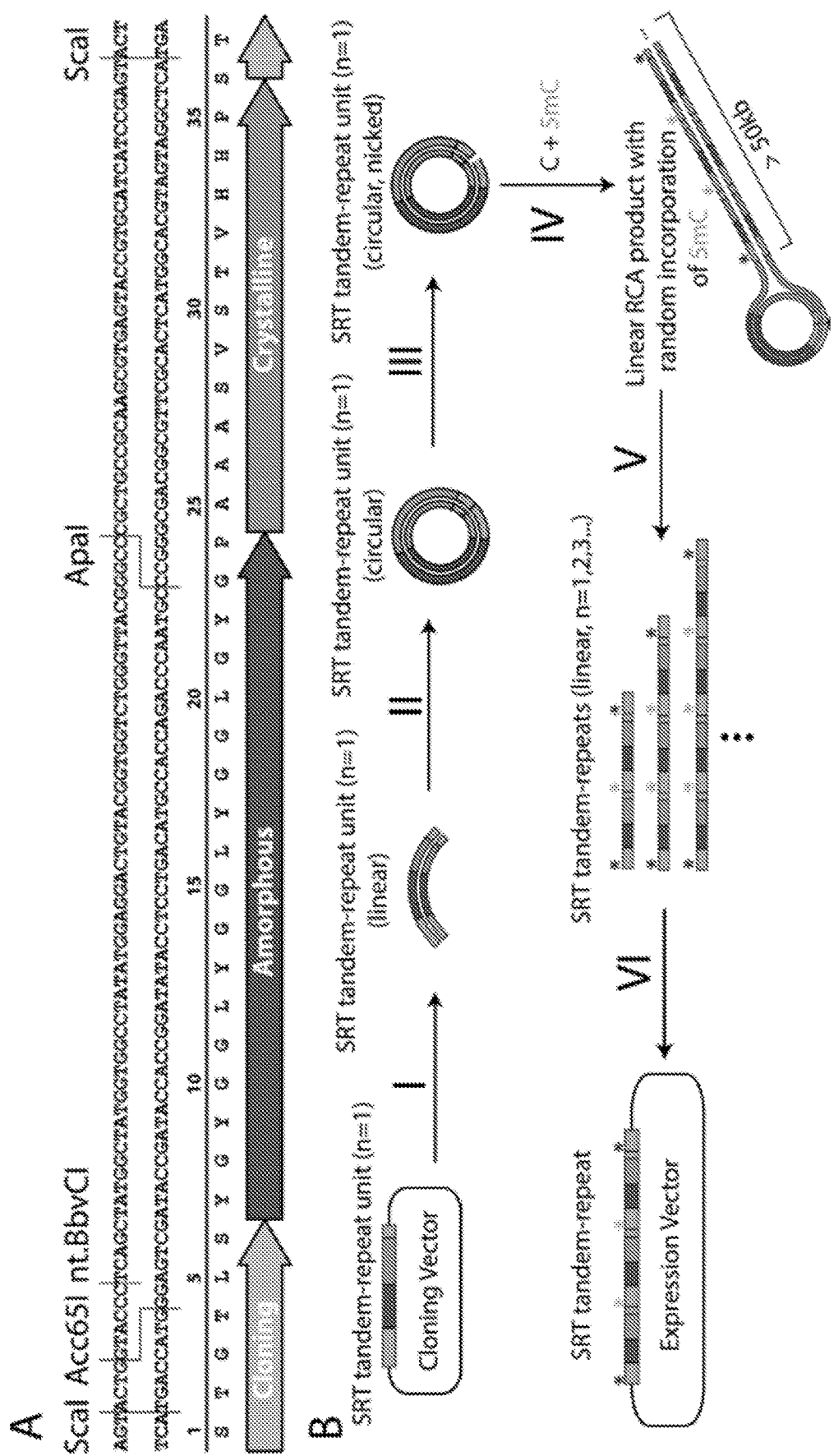

FIG. 4 shows tandem-repeat (TR) construction strategy to control the length of synthetic SRT proteins. (A) DNA and protein sequence of the tandem-repeat unit (n=1). Restriction sites introduced for DNA manipulation are indicated. Protein sequence is STGTLSYGYGGLYGGLYG-GLGYPAAASVSTVHHPST (SEQ ID NO:308). The top strand DNA sequence is AGTACTGGTACCCTCAGC-TATGGCTATGGTGGCCTATATG-GAGGACTGTACGGTGGT CTGGGT-TACGGGCCCGCTGCCGCAAGCGTGAGTACC-GTGCATCATCCGAGTACT (SEQ ID NO:309) and the bottom strand is GGATATACCTCCTGACATGCCACCA-GACCCAATGCCCGGGCGACGGCGTTCGCACT CATGGCACGTAGTAAGGCTCATGA (SEQ ID NO:310; given in the 5'-3' direction). (B) The tandem-repeat procedure. I: The TR unit is removed from its vector by digestion and gel purification. II: The TR unit is circularized by intramolecular ligation. III: The circular unit is nicked to create a priming site for rolling-circle amplification (RCA). IV: RCA in the presence of standard dNTPs plus 5-methyl dCTP causes 5-methylcytosine to be incorporated into the RCA product at random cytosine positions. V: Digestion of the RCA product with restriction enzymes that are blocked by 5-methylcytosine yields TR products with a distribution of different lengths. VI: The mixture of TR products is separated on a gel; the size range of interest is gel-purified and cloned into an expression vector.

Figure 5:
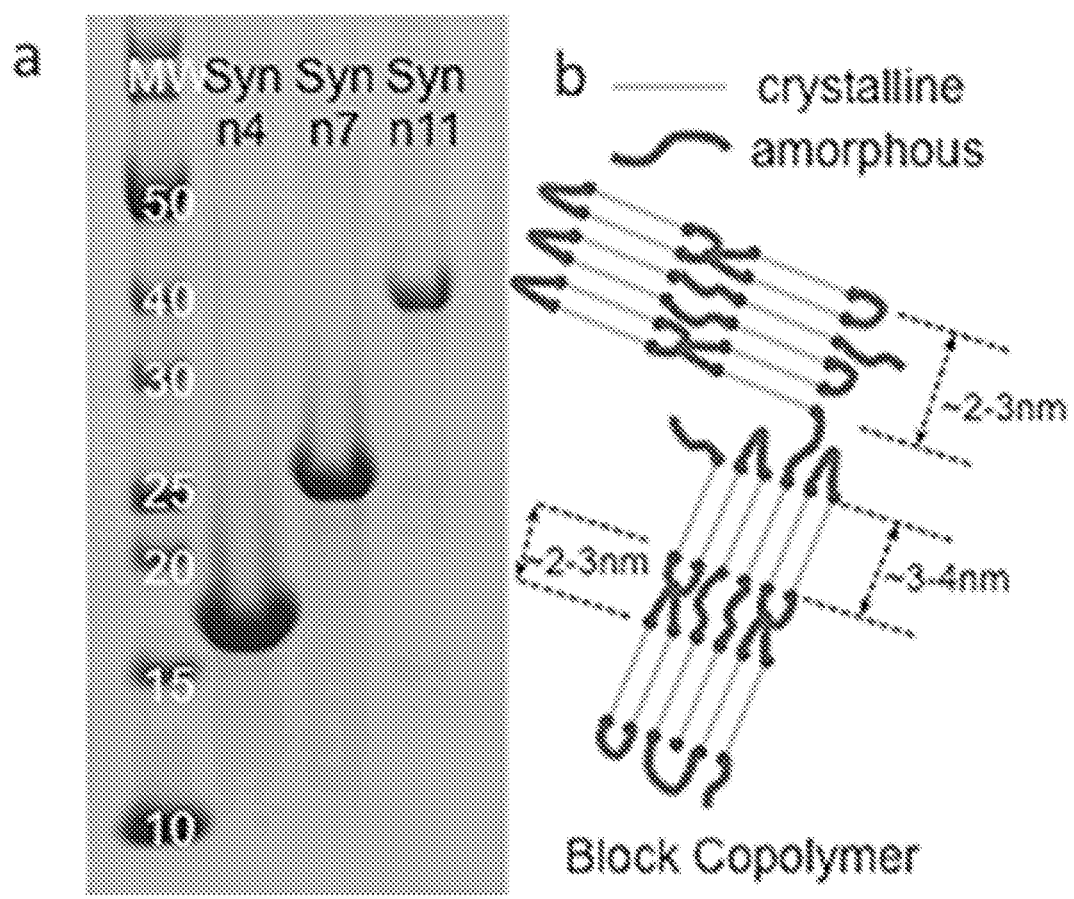
Figure 5:
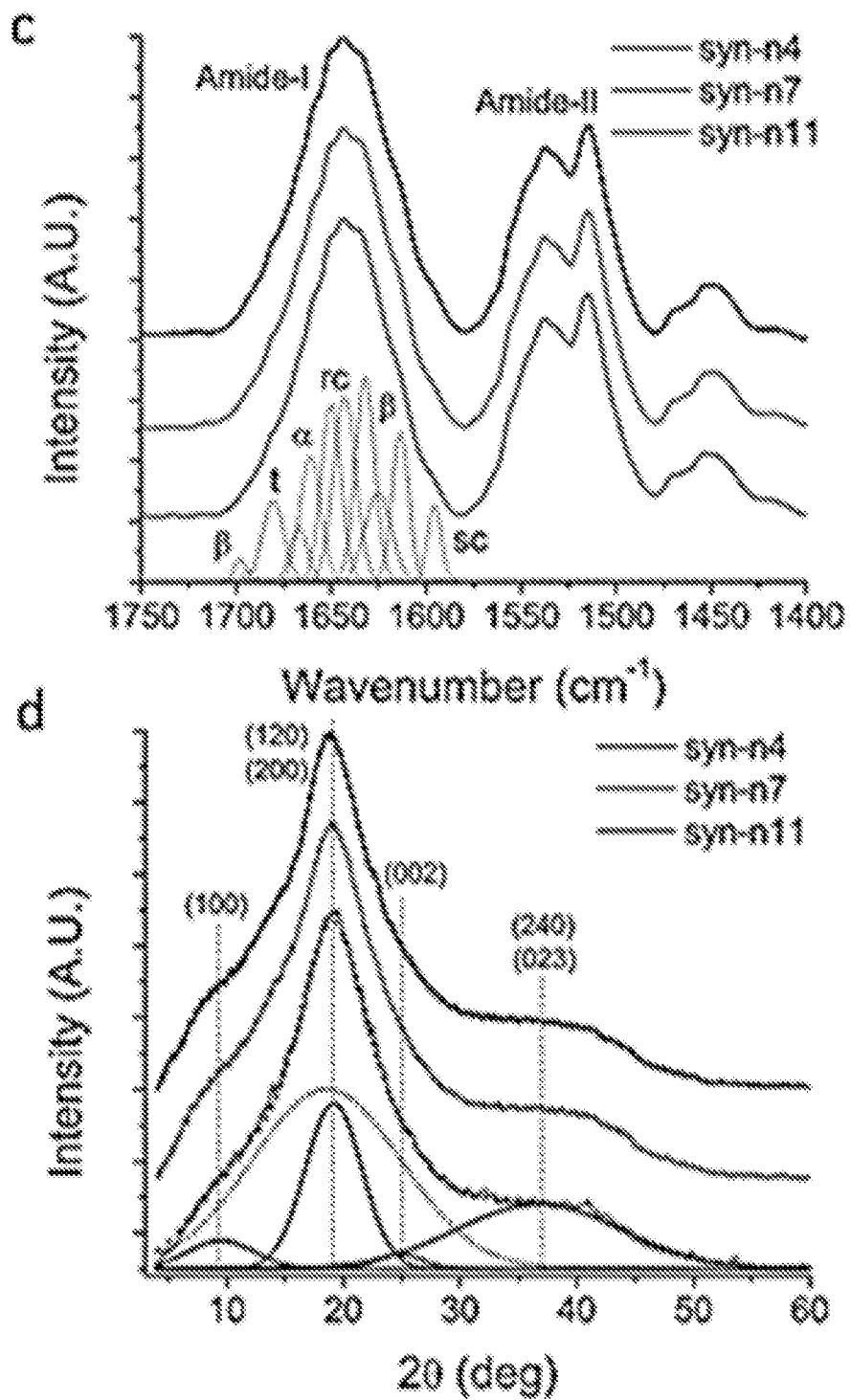

FIG. 5 shows (a) SDS-Page showing the sizes of the synthetic proteins with n=4, 7, 11. (b) Cartoon representation of the segmented polymer architecture of assembled polypeptides containing ordered β-sheet crystals and amorphous Gly-rich regions. Amorphous and crystalline are colored in green and red respectively. The FTIR (c) and XRD (d) spectra for all three samples are shown.

Figure 6:
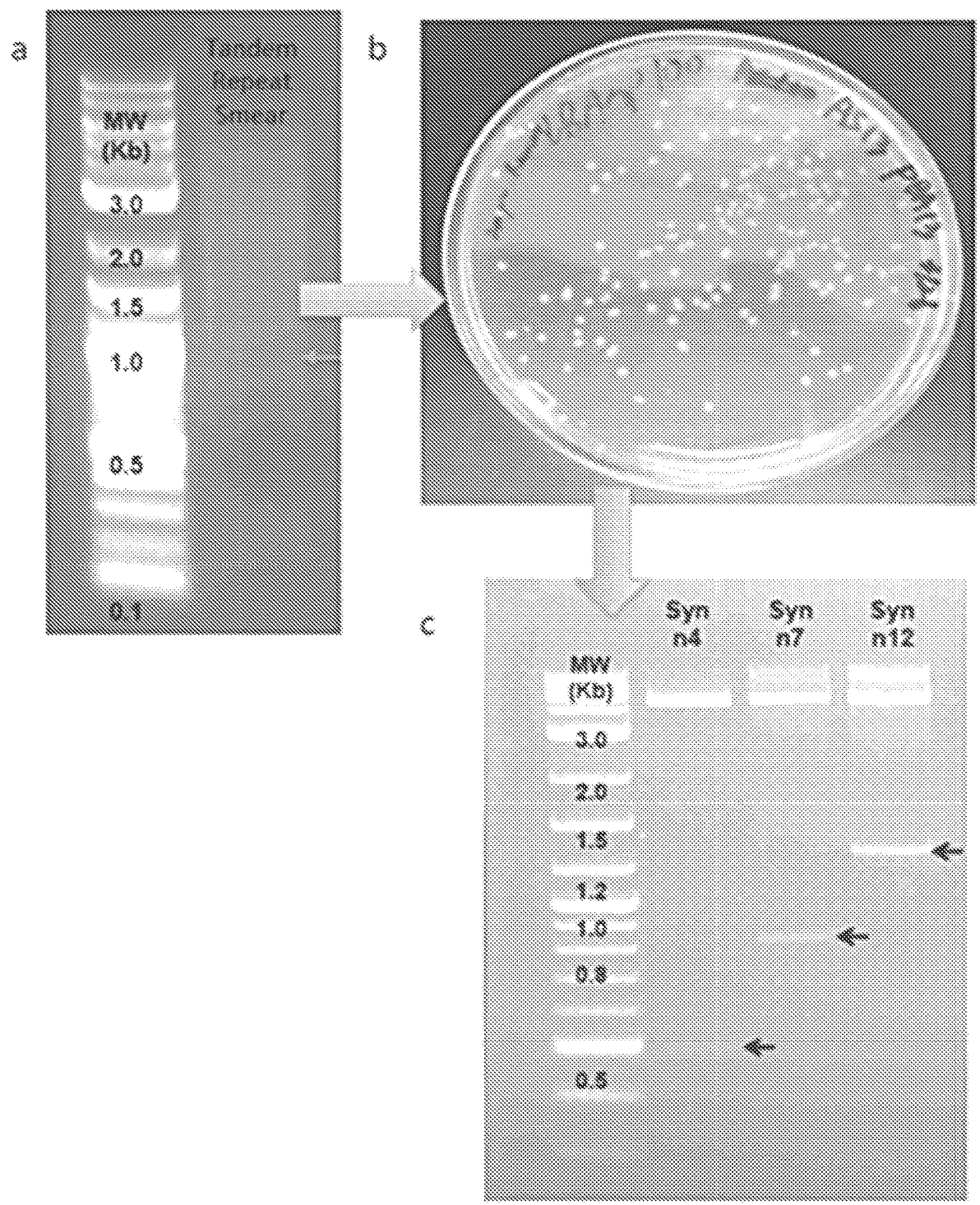

FIG. 6 shows (a) synthetic polypeptides are obtained using the rolling circle amplification method, which created a smear band in the DNA gel. Once the sequence of interest is identified, the resulting gene sequence is then ligated into a cloning vector and recombinantly expressed in E. Coli (b). Examples of tandem repeat construction of n=4,7 12 with DNA gels are shown in (c).

Figure 7:
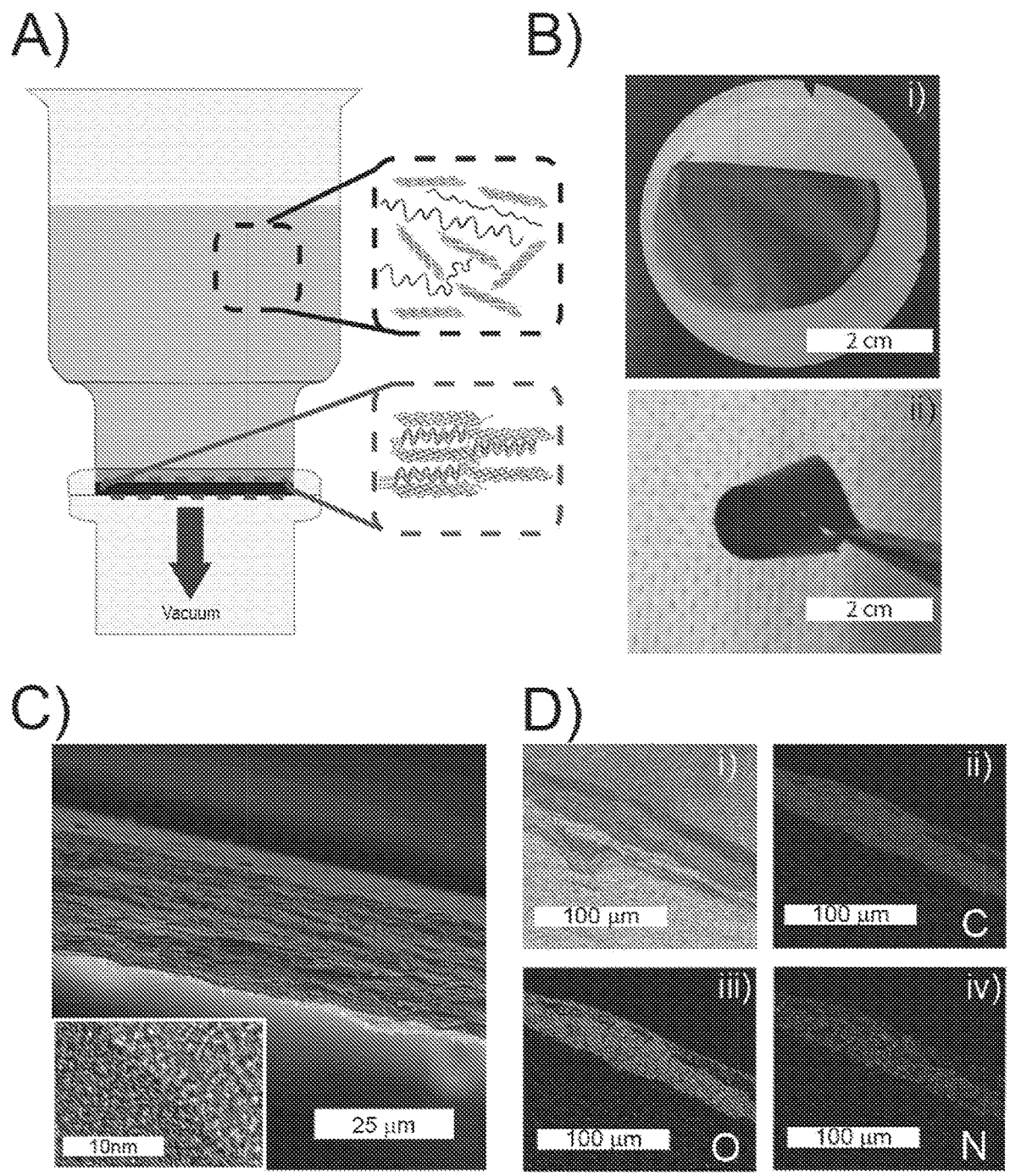
Figure 8:
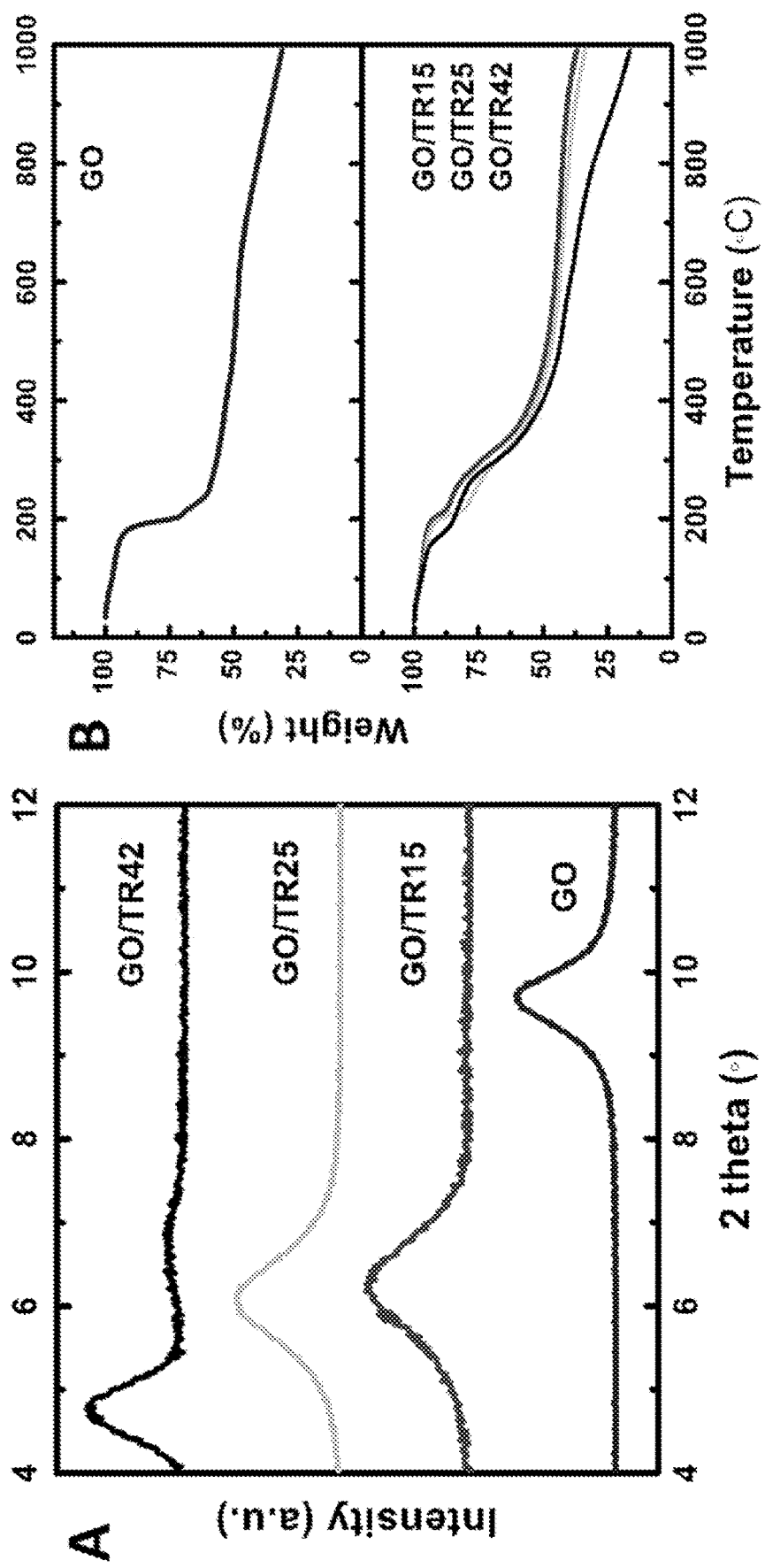

FIG. 7 shows A) schematic illustration of vacuum assisted self-assembly (VASA) of 2D molecular composites. B) Image of free-standing molecular composite consisting of GO and synthetic protein with 42 kDa molecular weight. C) Cross-section scanning electron microscope (SEM) and transmission electron microscope (inset) image of molecular composite consisting of GO and synthetic protein with 25 kDa molecular weight. D) i) Backscattered electron image, and energy dispersive X-ray spectroscopy (EDS) patterns of ii) carbon, iii) oxygen, iv) nitrogen for molecular composite consisting of GO and synthetic protein with 25 kDa molecular weight FIG. 8 shows A) XRD spectra for GO, and molecular composites prepared using TR15, TR25, TR42 synthetic proteins. d-spacing between individual layers of GO increases as a function of the molecular weight of the intercalating Tr-proteins (i.e., interlayer distance of 4.96, 5.41, 9.50 Å for Tr15, 25, 42 proteins respectively). B) Thermogravimetric analysis coupled with a mass spectrometry (TGA-MS) for GO, and molecular composites consisting of GO/TR15, GO/TR25 and GO/TR42 show approximately 55% protein content, which agrees with the density measurements (i.e., $\rho_{Go/Tr\text{-}15}$=1.82, $\rho_{Go/Tr\text{-}25}$=1.78, and $\rho_{Go/Tr\text{-}42}$=1.61) of these composites.

Figure 9:
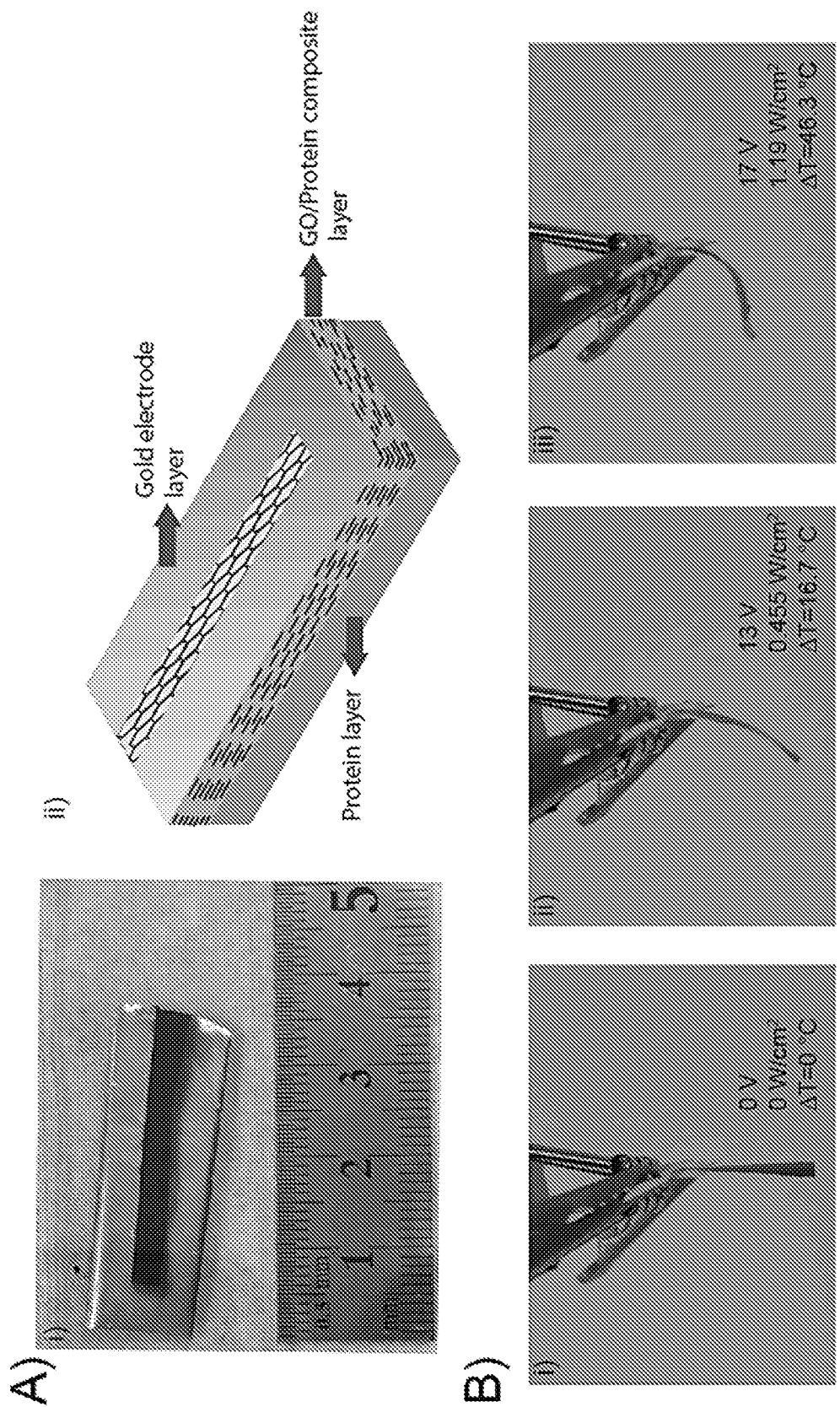
Figure 9:
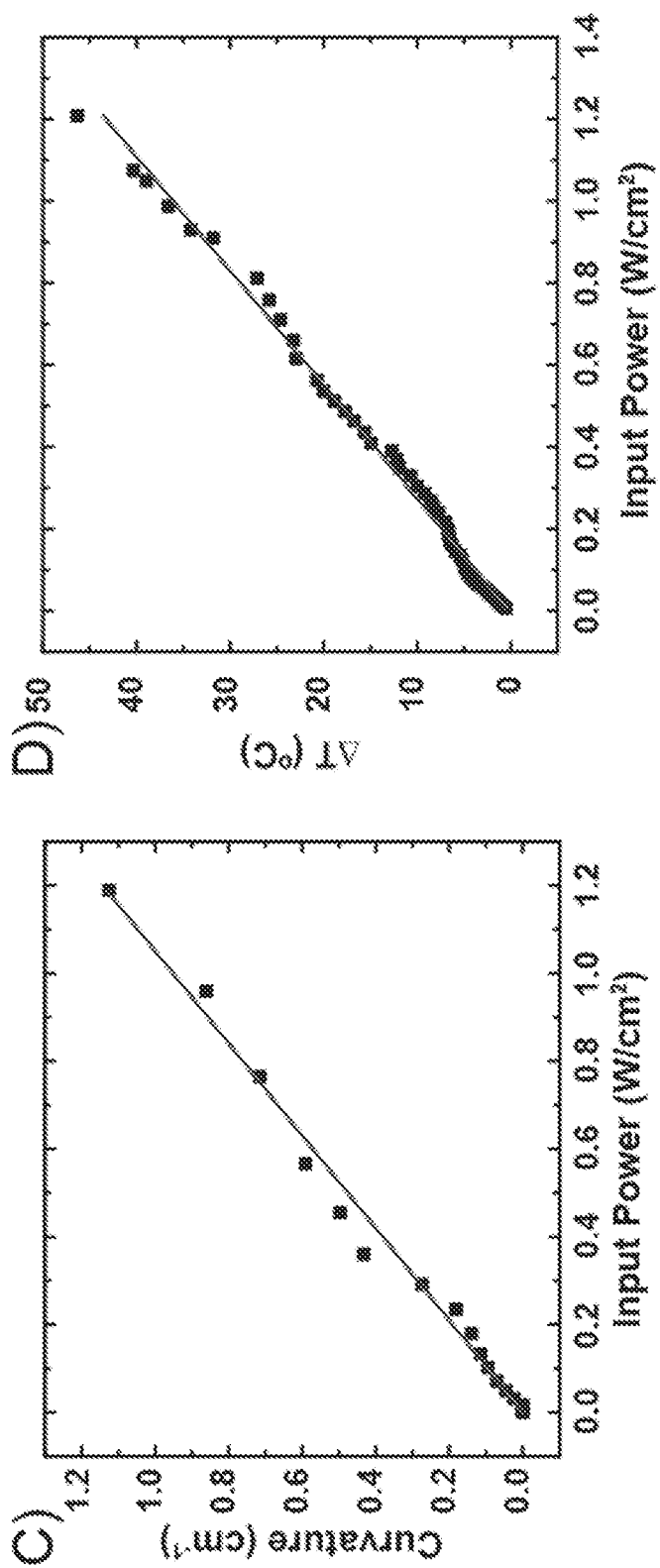

FIG. 9 shows A) i) image and ii) schematic illustration of thermal actuators. Images of the thermal actuator under different voltages. C) Curvature values as a function of the applied power. D) Relative change in temperature as a function of the applied power.

Figure 10:
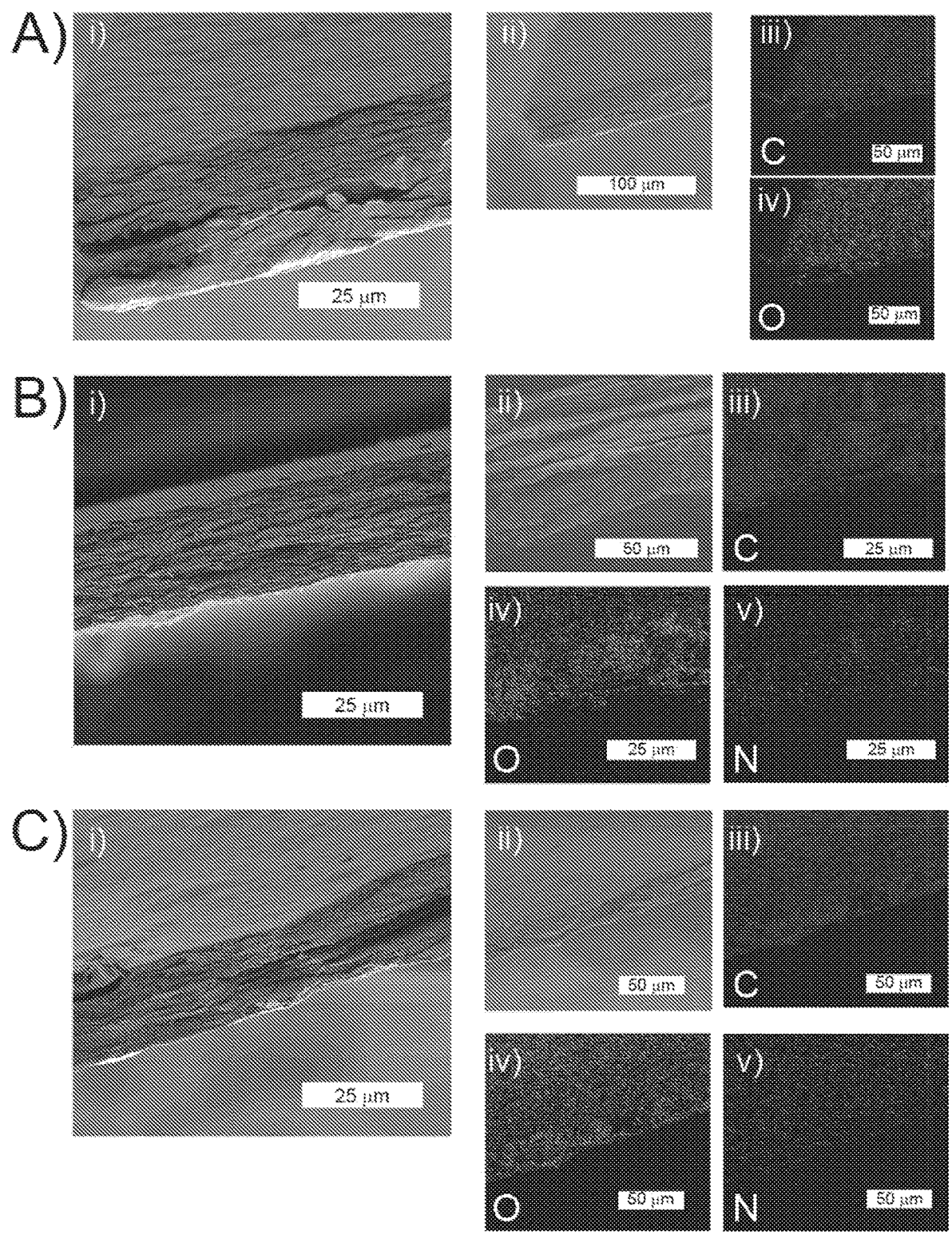

FIG. 10 shows A) i) cross-section scanning electron microscope (SEM), ii) Backscattered electron image, and energy dispersive X-ray spectroscopy (EDS) patterns of ii) carbon, iii) oxygen, iv) nitrogen for GO film. i) Cross-section scanning electron microscope (SEM), ii) Backscattered electron image, and energy dispersive X-ray spectroscopy (EDS) patterns of ii) carbon, iii) oxygen, iv) nitrogen for molecular composite consisting of GO and synthetic protein with B) 25 kDa and C) 42 kDa molecular weight.

Figure 11:
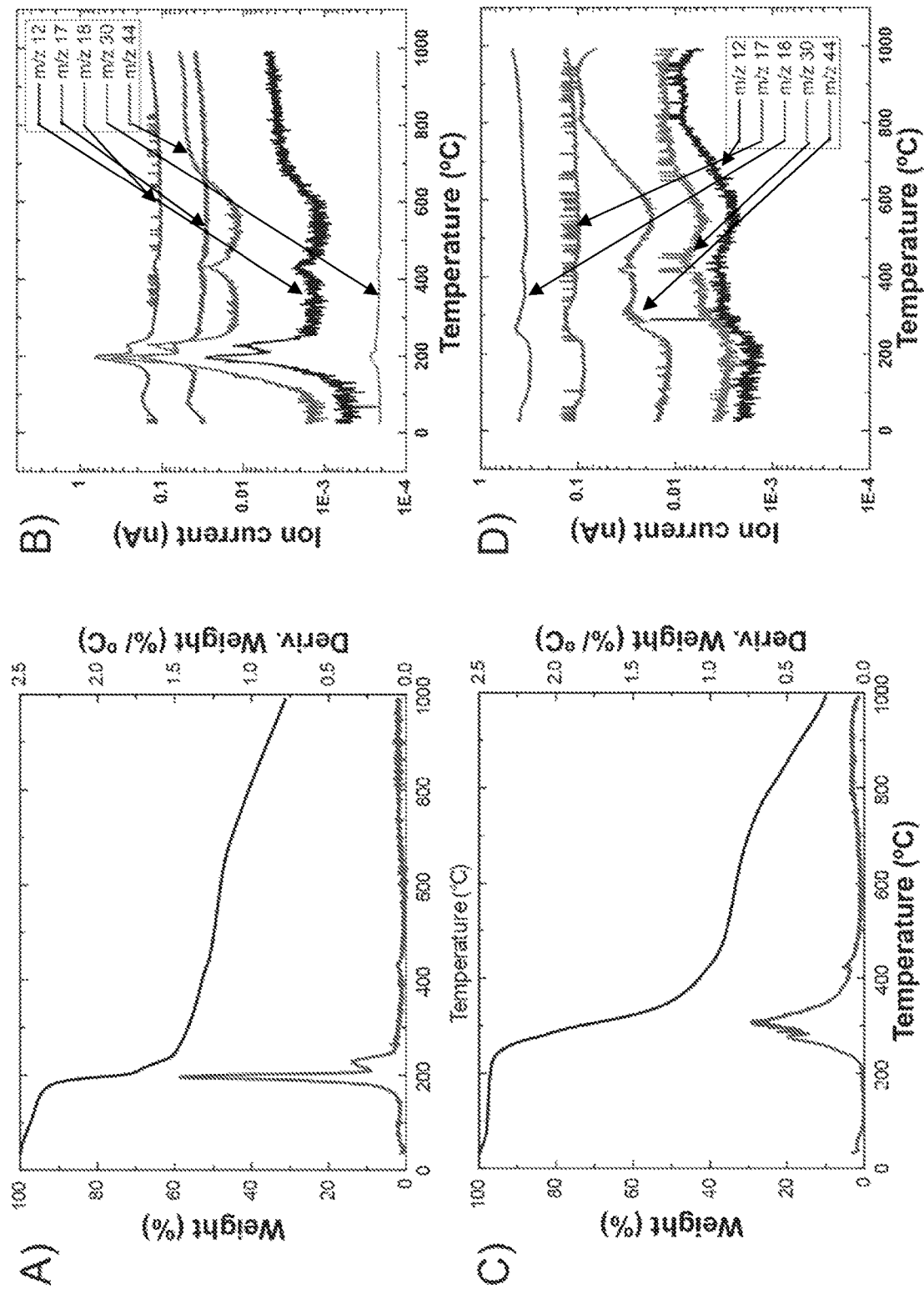
Figure 11:
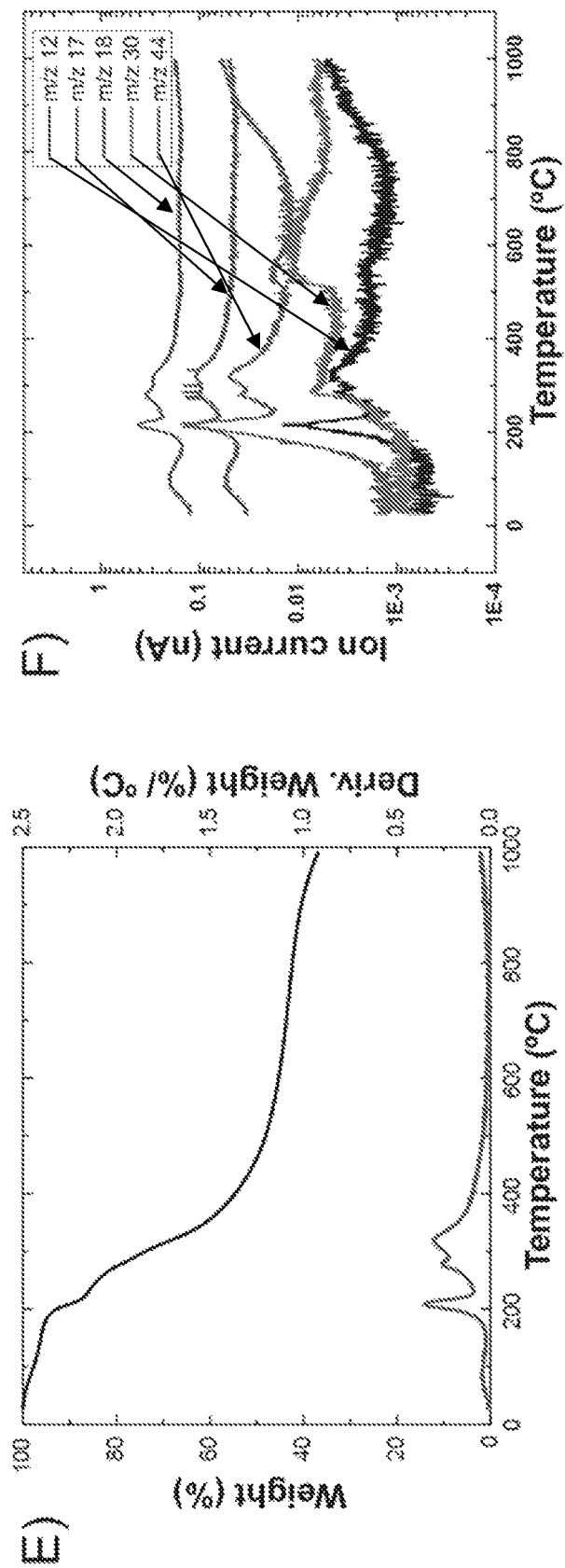
Figure 11:
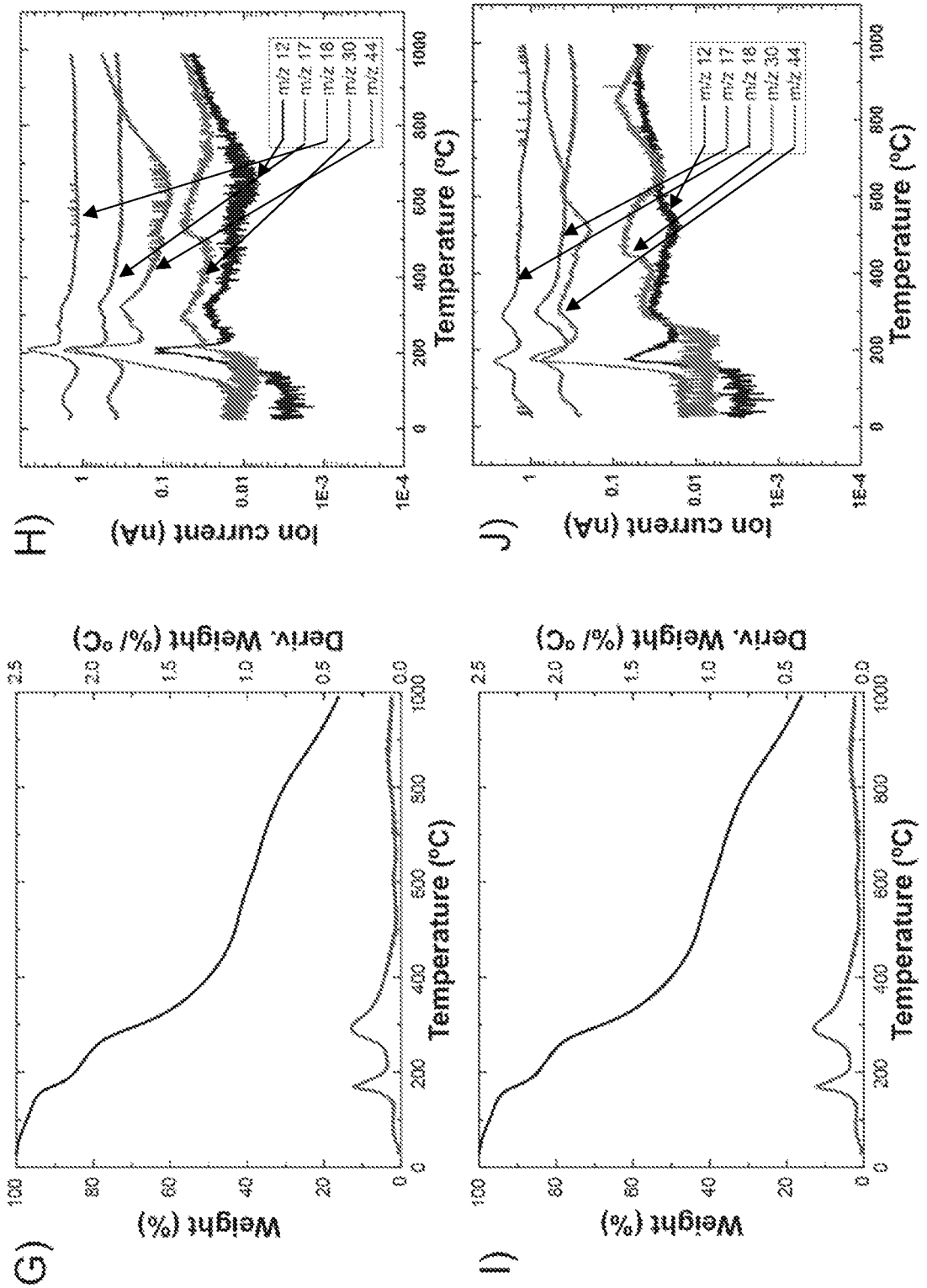

FIG. 11 shows thermogravimetric analysis (TGA) data with wt % (black) and derivative of wt % (red) for A) GO, C) synthetic protein (TR42), and molecular composites consisting of E) GO/TR15, G) GO/TR25 and I) GO/TR42. Mass spectroscopy data acquired during TGA analysis for B) GO, D) synthetic protein (TR42), and molecular composites consisting of F) GO/TR15, H) GO/TR25 and J) GO/TR42. (m/z 12, 17, 18, 30, and 44 represents (C), (OH), ($H_2O$), (NO), and (CO) compositions, respectively).

Figure 12:
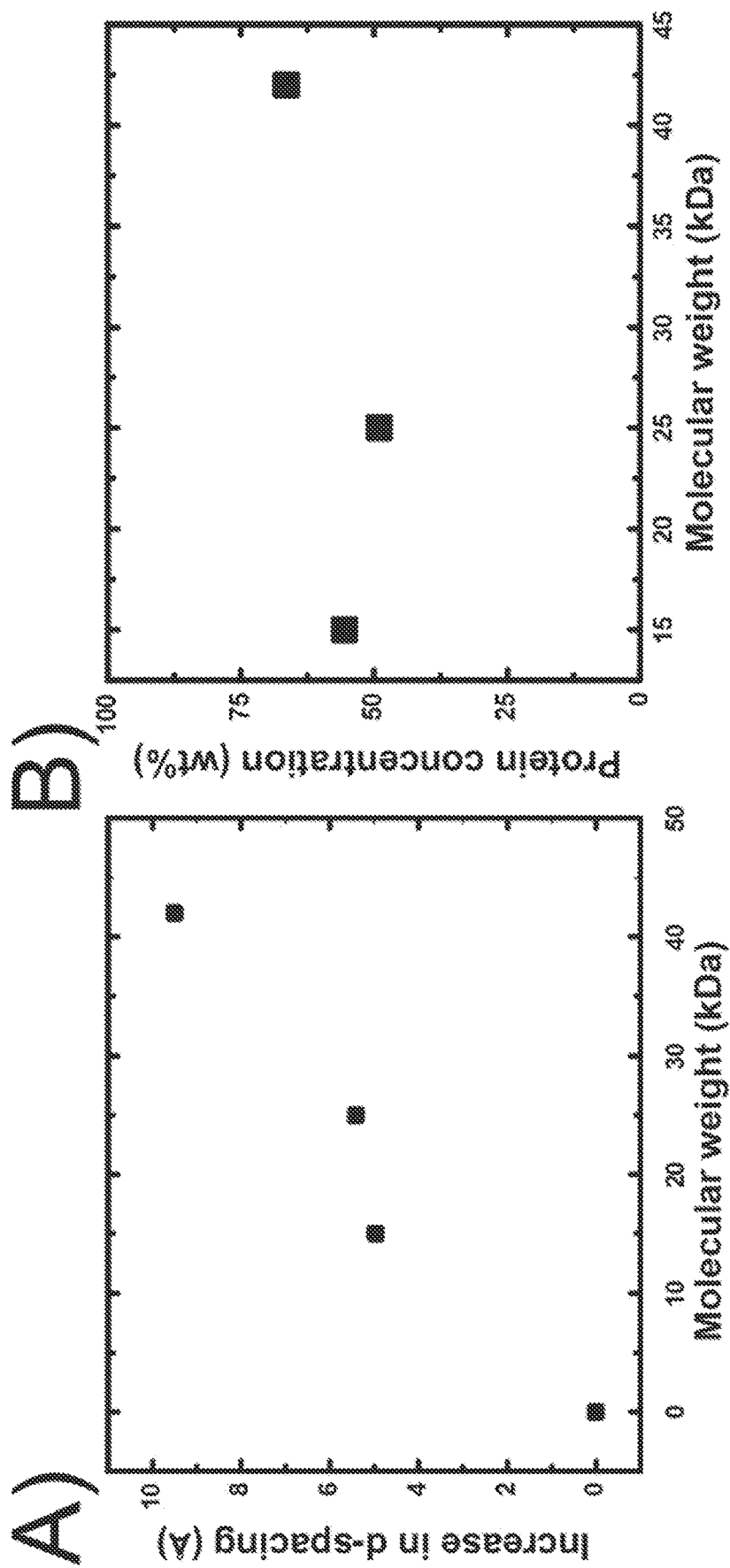

FIG. 12 shows increase in interlayer distance (d-spacing) between GO sheets for molecular composites with respect to molecular weight of the synthetic proteins. Protein concentration in molecular composites as a function of the molecular weight of the synthetic proteins.

Figure 13:
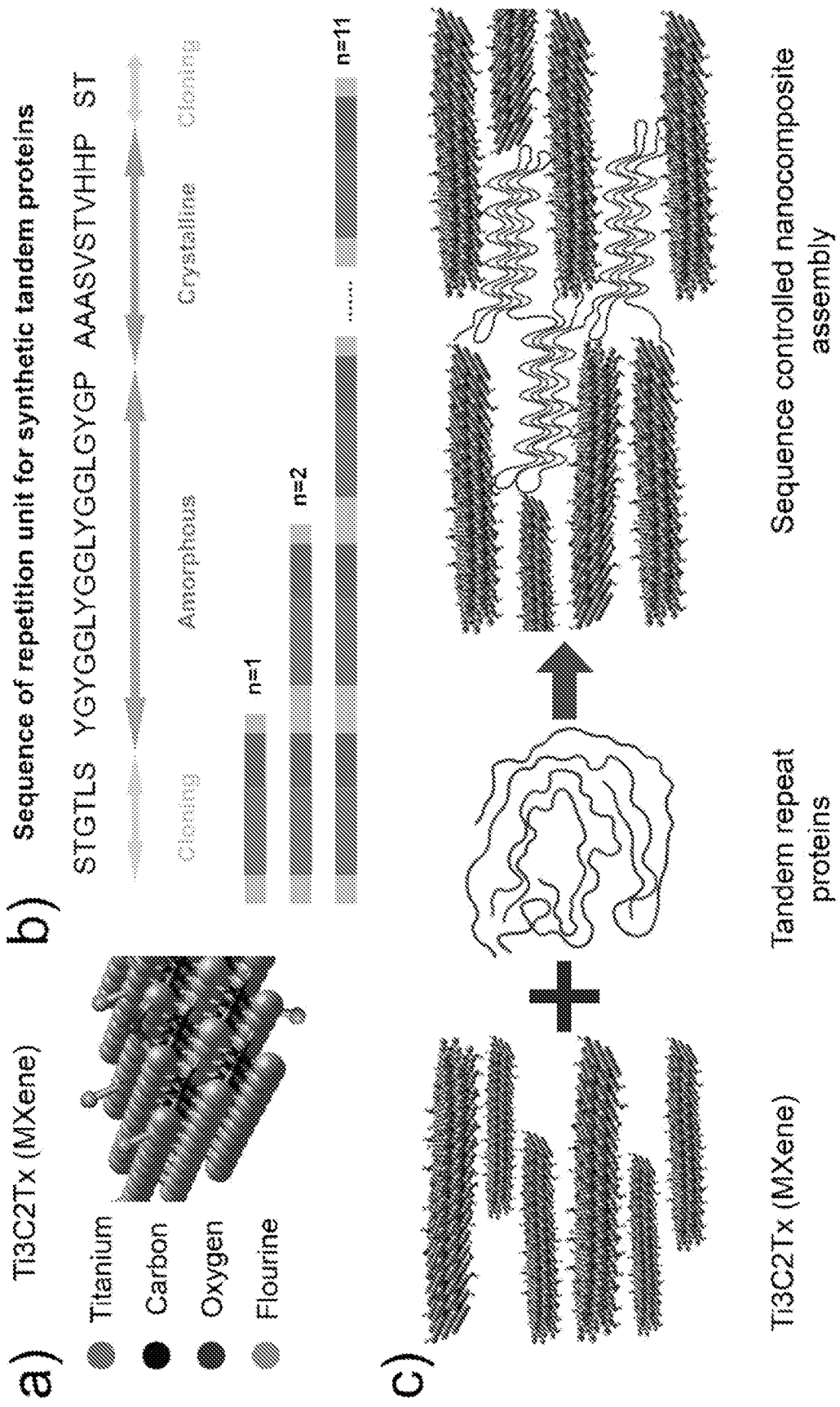
Figure 13:
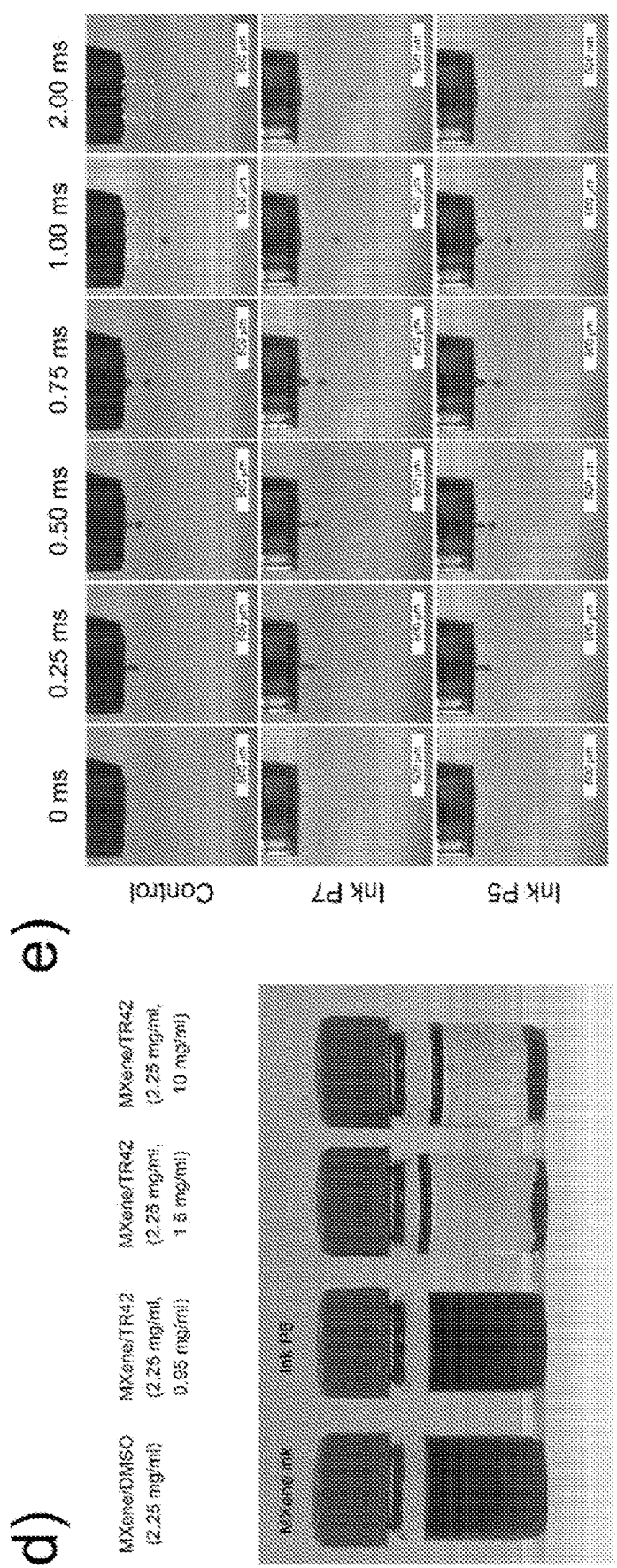

FIG. 13 shows schematic illustration of two-dimensional titanium carbide (MXene), b) repeating amino acid sequence of proteins and tandem repetition process. c) Schematic representation of protein mediated assembly of MXene sheets. d) Images of pristine, and protein based MXene/DMSO dispersions with various protein concentrations. e) Images of droplet jetting sequence of various ink formulations acquired from stroboscopic camera of inkjet printer.

Figure 14:
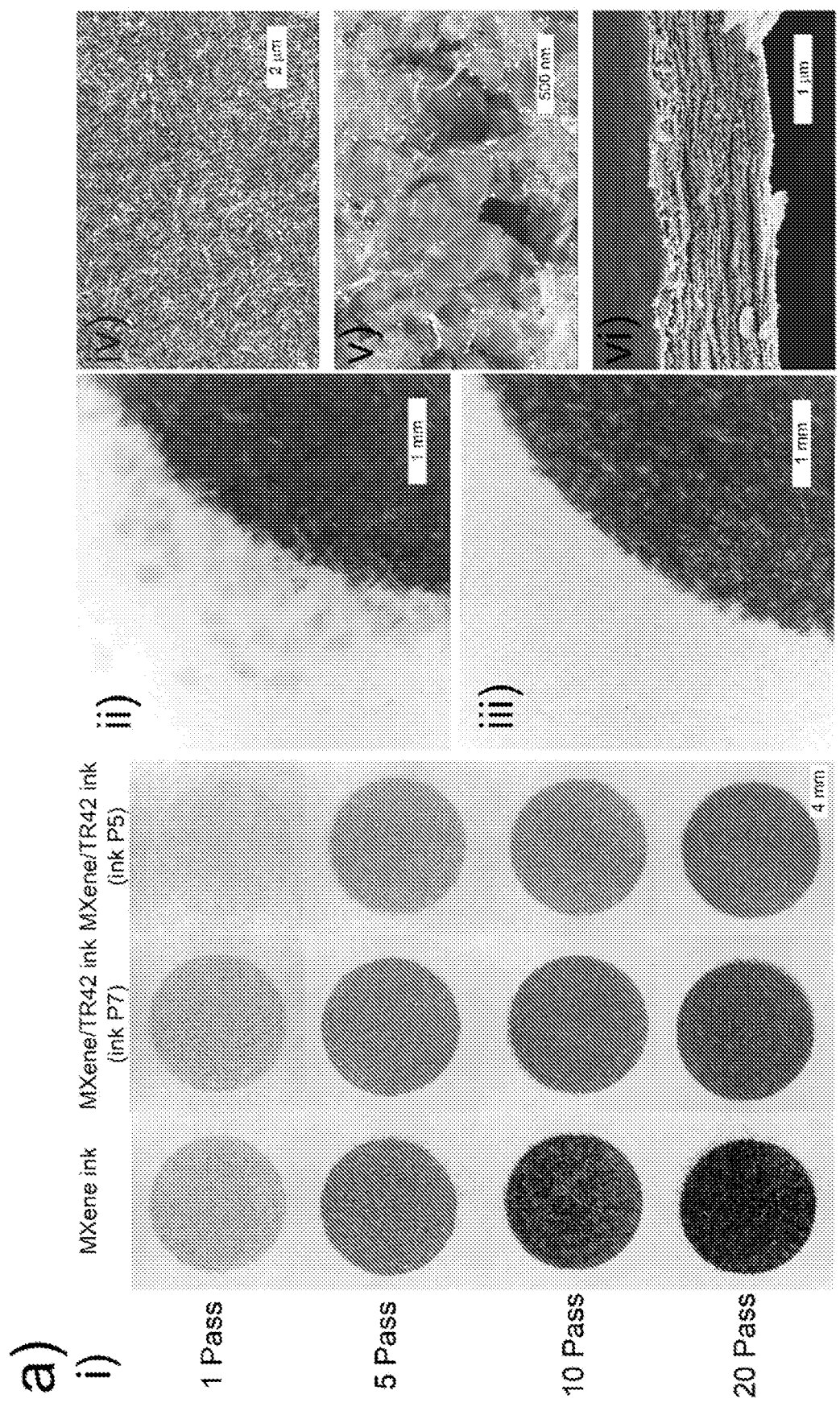
Figure 14:
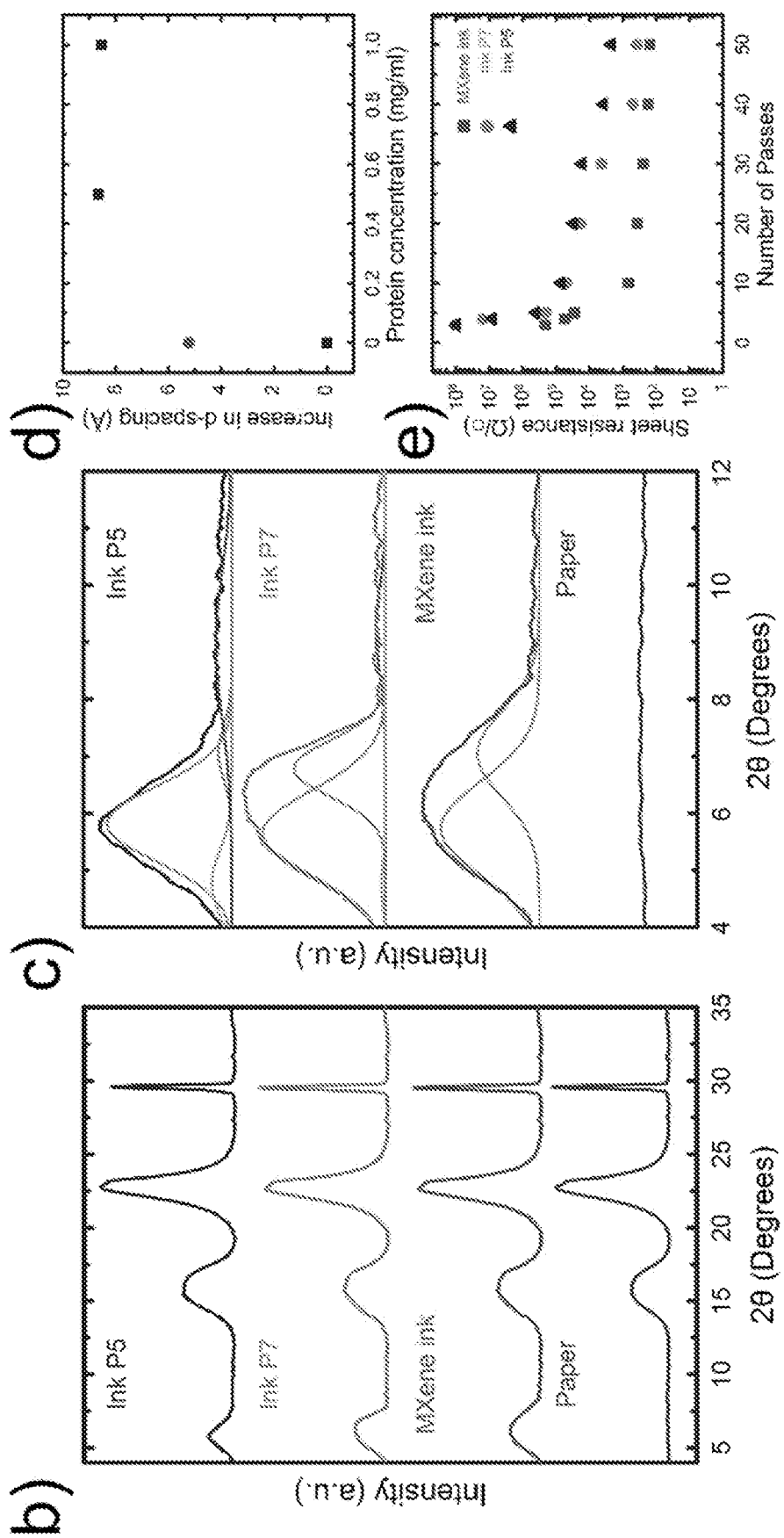

FIG. 14 shows a) i) optical images of circles printed on paper using various ink solutions during printing passes/cycles. Higher magnification images of circles printed on paper substrates using ii) pristine MXene ink, and iii) ink P5. iv) Low magnification, and v) high magnification SEM images of circles printed on paper using ink P5. vi) Cross-section SEM image of circles printed on paper using ink P5. b) X-ray diffraction (XRD) spectra of circles printed on paper using various ink formulations. c) XRD spectra of circles printed on paper using various ink formulations focused on MXene (002) plane. d) d-spacing between MXene layers calculated from XRD spectra (red data point represents interlayer spacing originating from DMSO intercalation). e) Sheet resistance values of circles printed on paper using various ink formulations as a function of printing passes/cycles.

Figure 15:
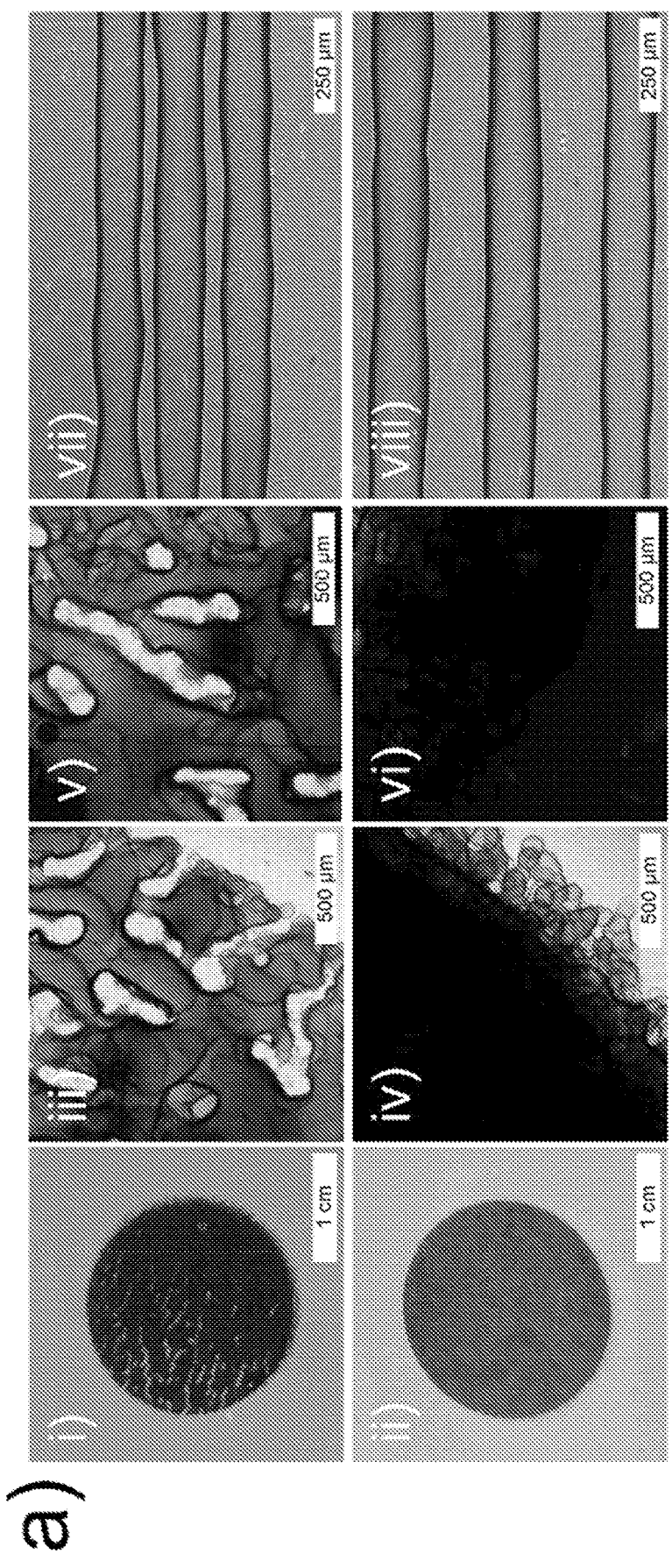
Figure 15:
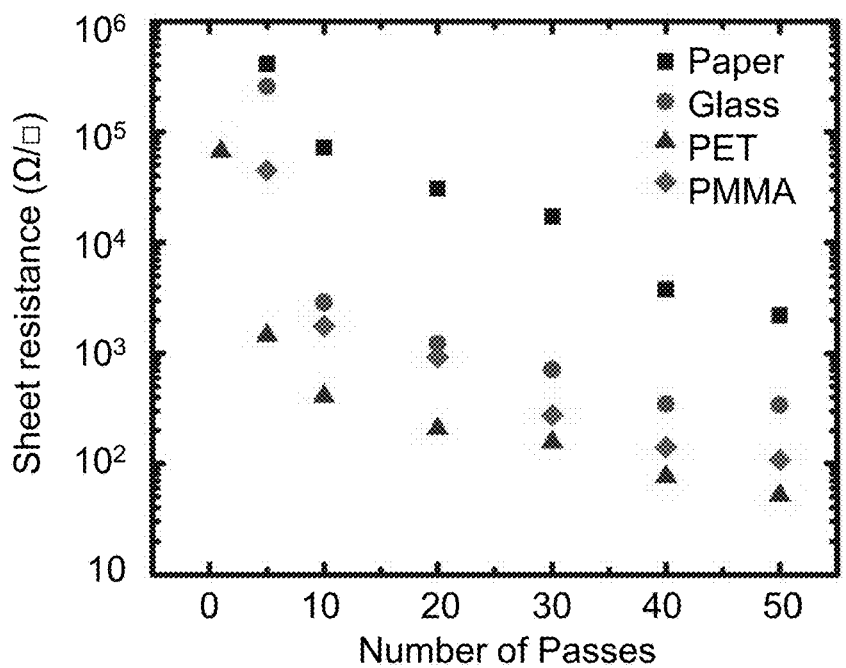
Figure 15:
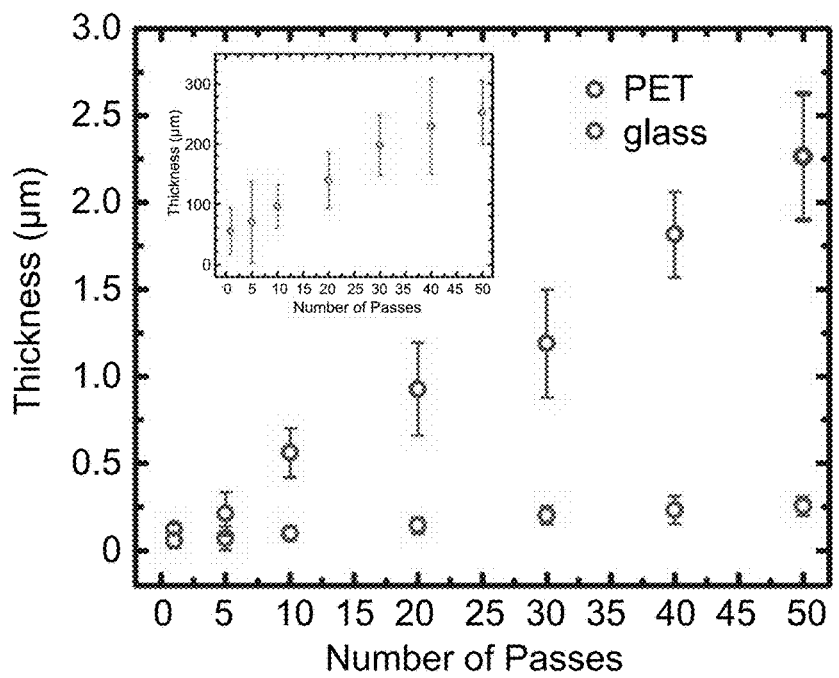

FIG. 15 shows a) Low magnification optical images of circles printed on PET substrates using i) pristine MXene ink and ii) P5 ink (30 passes/cycles). High magnification optical images of the edge of circles printed on PET substrates using iii) pristine MXene ink and iv) P5 ink (30 passes/cycles). High magnification optical images of the center of circles printed on PET substrates using v) pristine MXene ink and vi) P5 ink (30 passes/cycles). High magnification optical image of conductive lines (width: 120 µm, length: 2 cm) printed on PET using ink P5 with interline spacing of vii) 40 µm and viii) 150 b) Sheet resistance values of circles printed on various substrates using ink P5 as a function of printing passes/cycles. c) Average thickness of circles printed on glass and PET as a function of printing passes/cycles.

Figure 16:
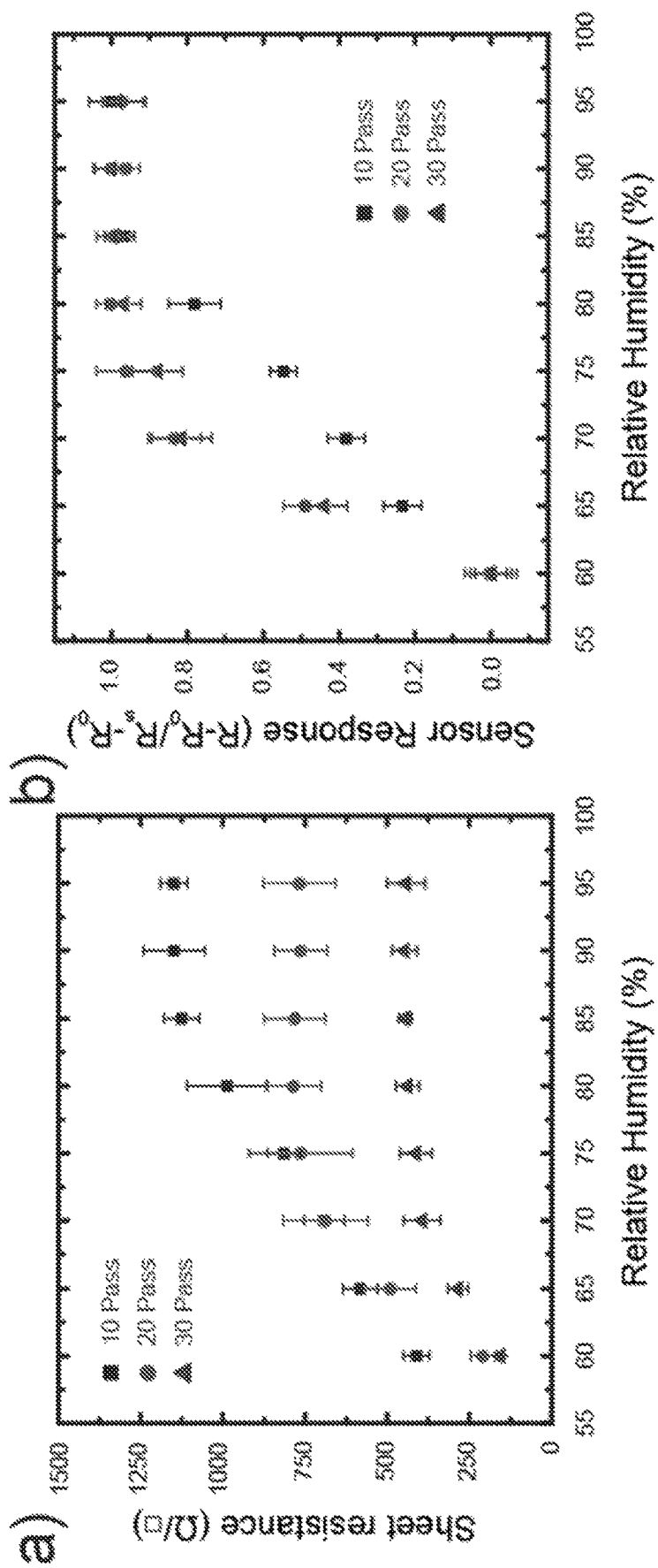
Figure 16:
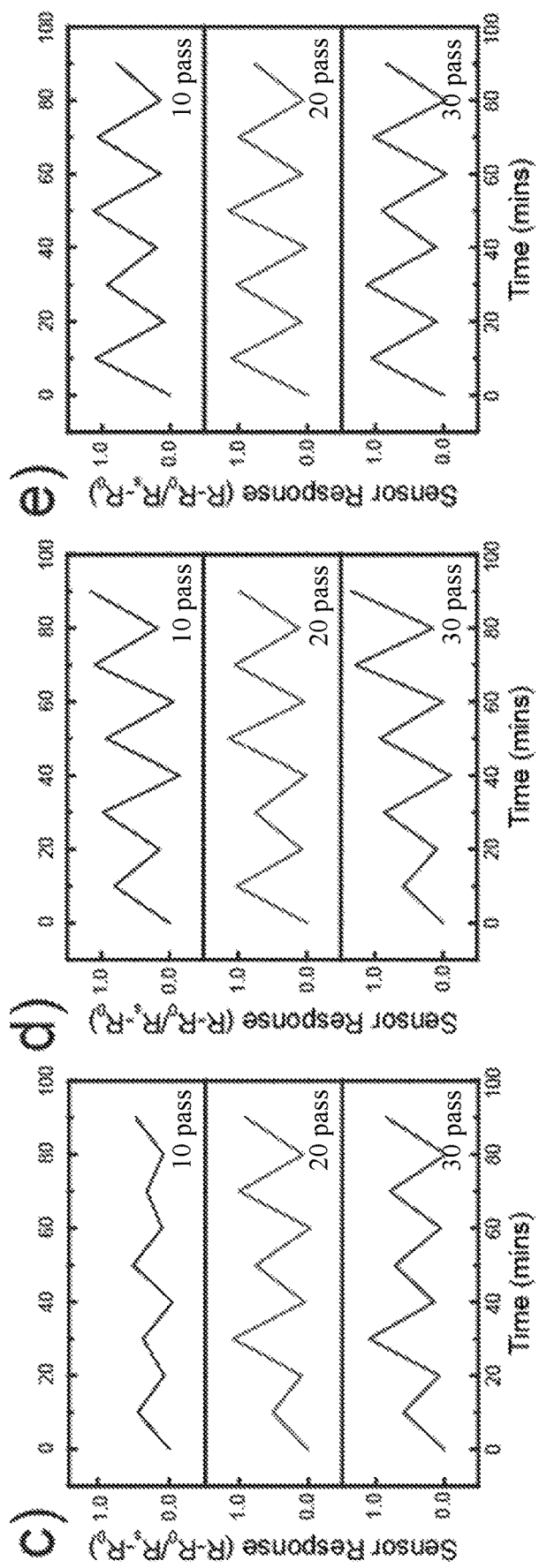

FIG. 16 shows a) sheet resistance values of conductive lines with various thickness printed on PET using ink P5 as a function of relative humidity. b) Sensor response of conductive lines with various thickness printed on PET using ink P5 as a function of relative humidity. Sensor response of conductive lines with various thickness printed on PET using ink P5 during humidity cycles alternating between c) 60% and 70%, d) 60% and 80%, e) 60% and 90% relative humidity.

Figure 17:
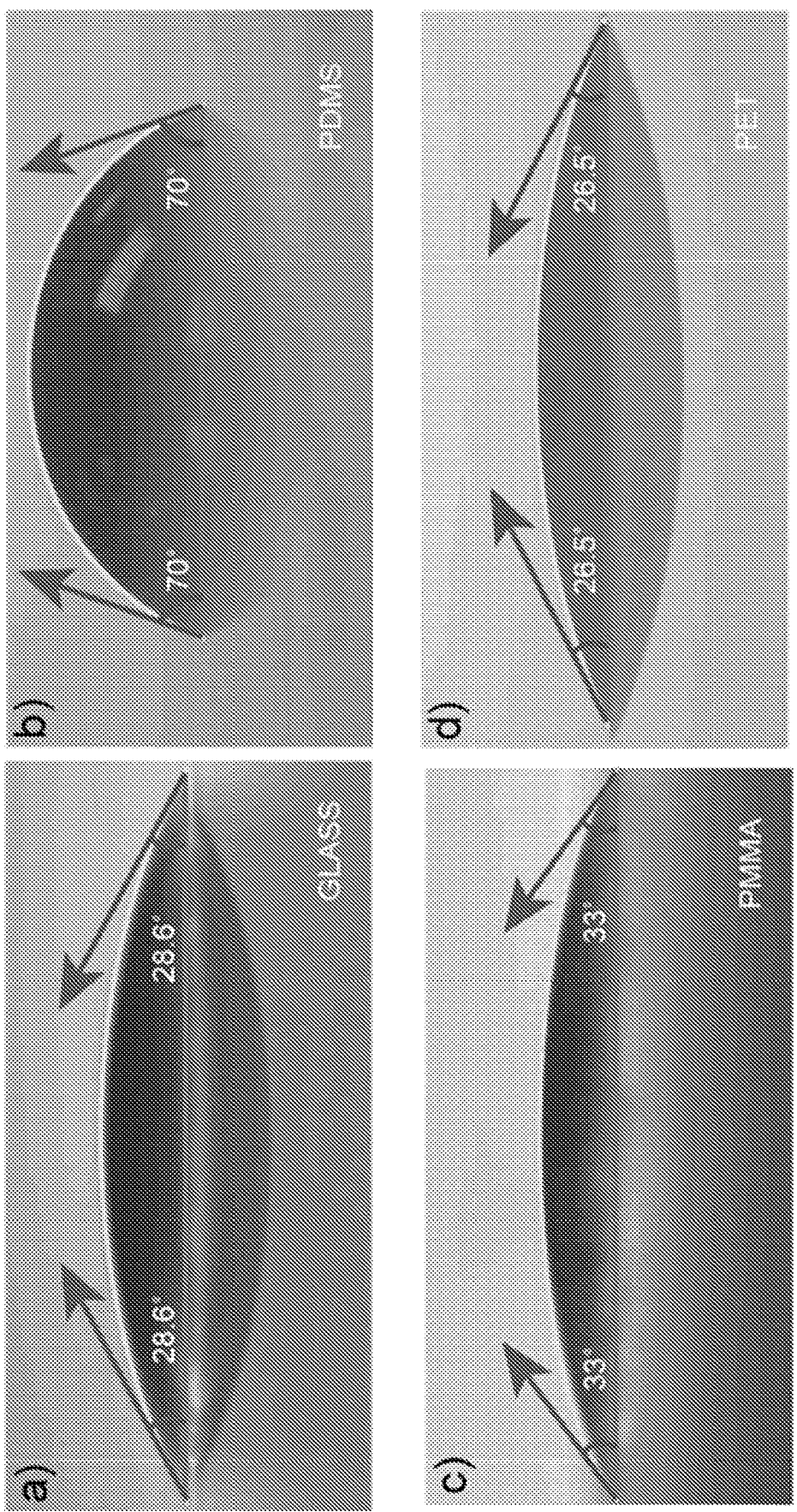
Figure 17:
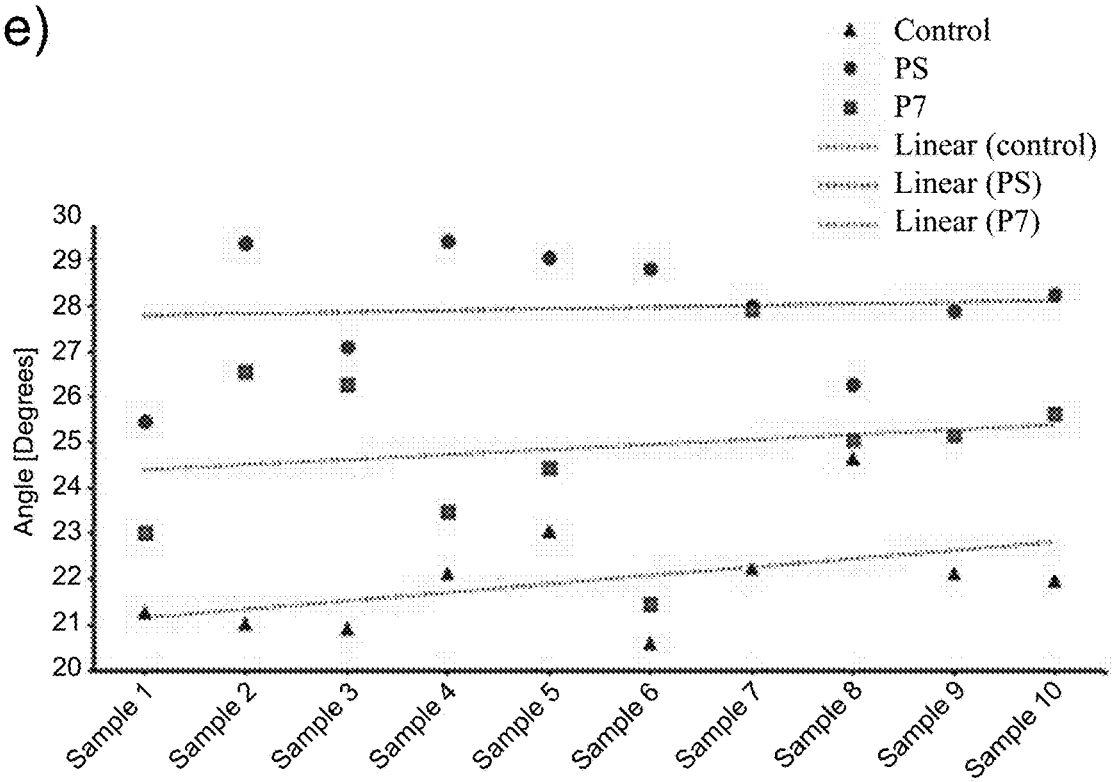
Figure 17:
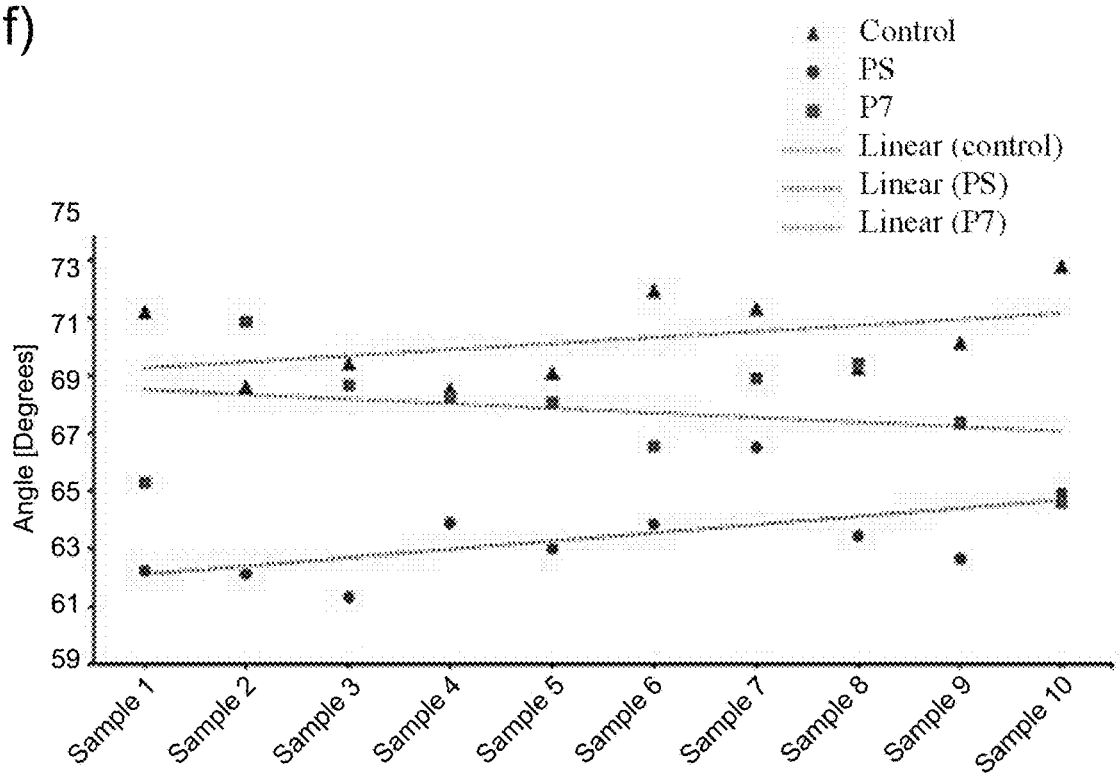
Figure 17:
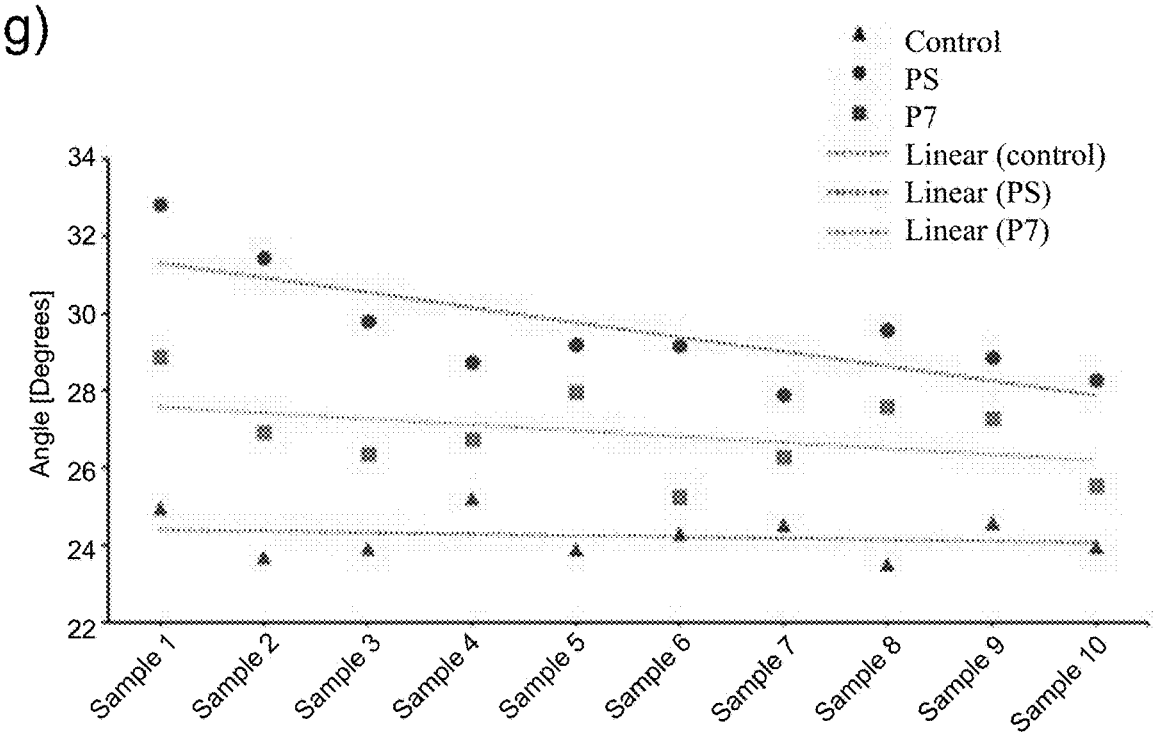
Figure 17:
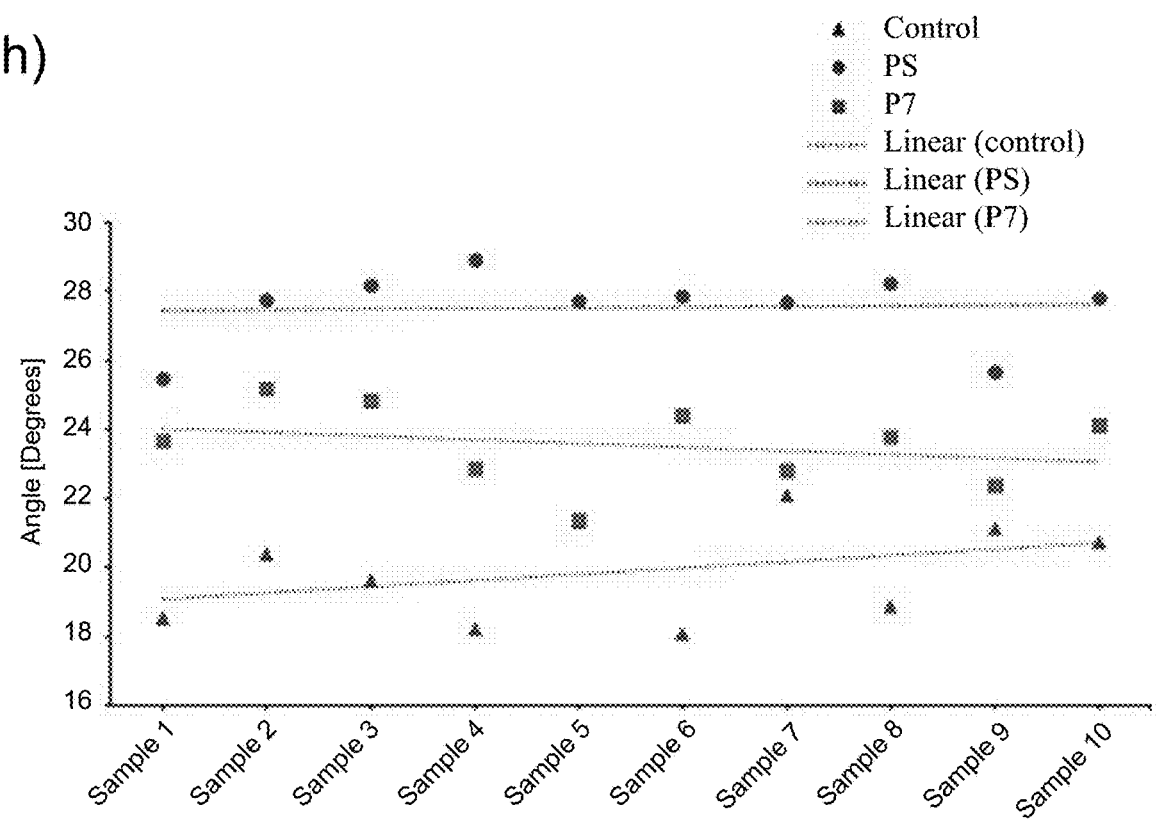

FIG. 17 shows an ink P5 drop is deposited on: a) fused silica glass, b) cured PDMS film, c) PMMA sheet, and d) PET film. Contact angle values calculated using image processing tools (Fiji software) for various ink formulations printed on fused silica glass, PDMS film, PMMA sheet and PET film.

Figure 18:
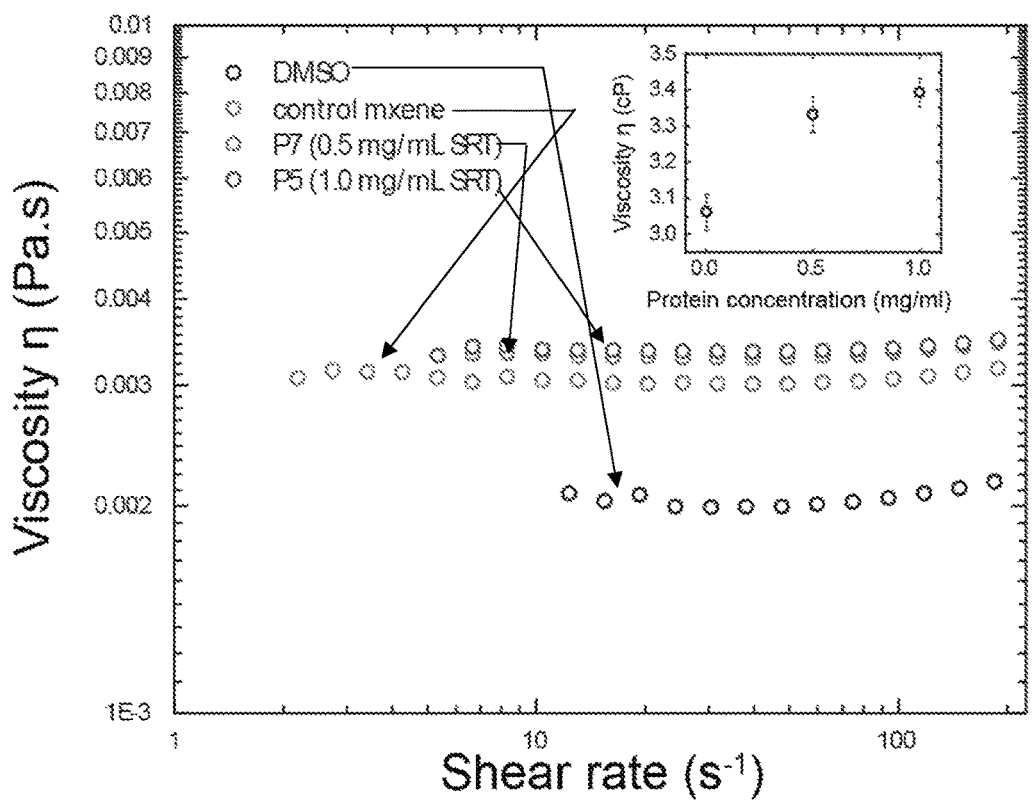

FIG. 18 shows a change in dynamic viscosity (ii) measured for MXene inks (Control/pristine, ink P7 and ink P5). (Inset-Viscosity is provided as a function of protein concentration).

Figure 19:
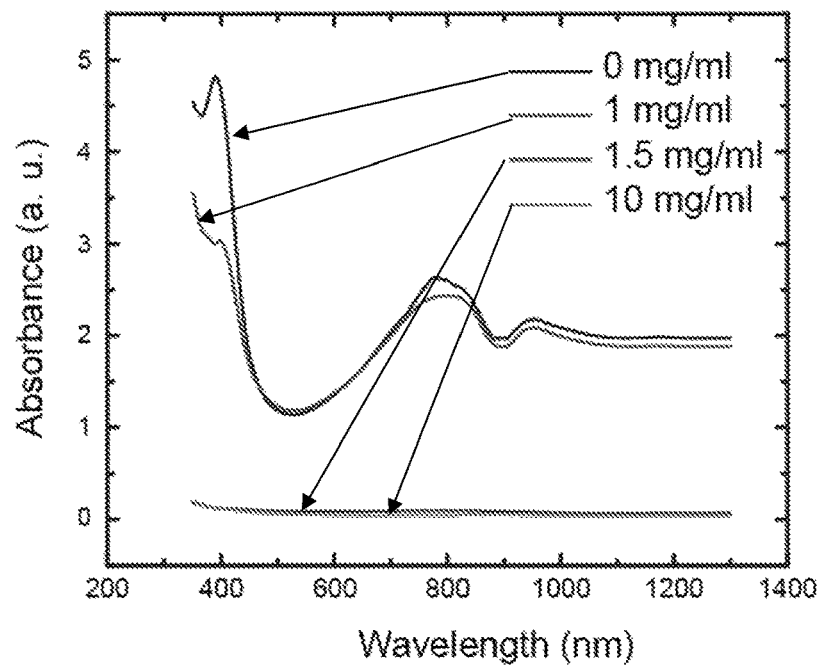

FIG. 19 shows an UV/NIR absorbance spectrum of DMSO based MXene solutions with various tandem protein (TR42) concentration.

Figure 20:
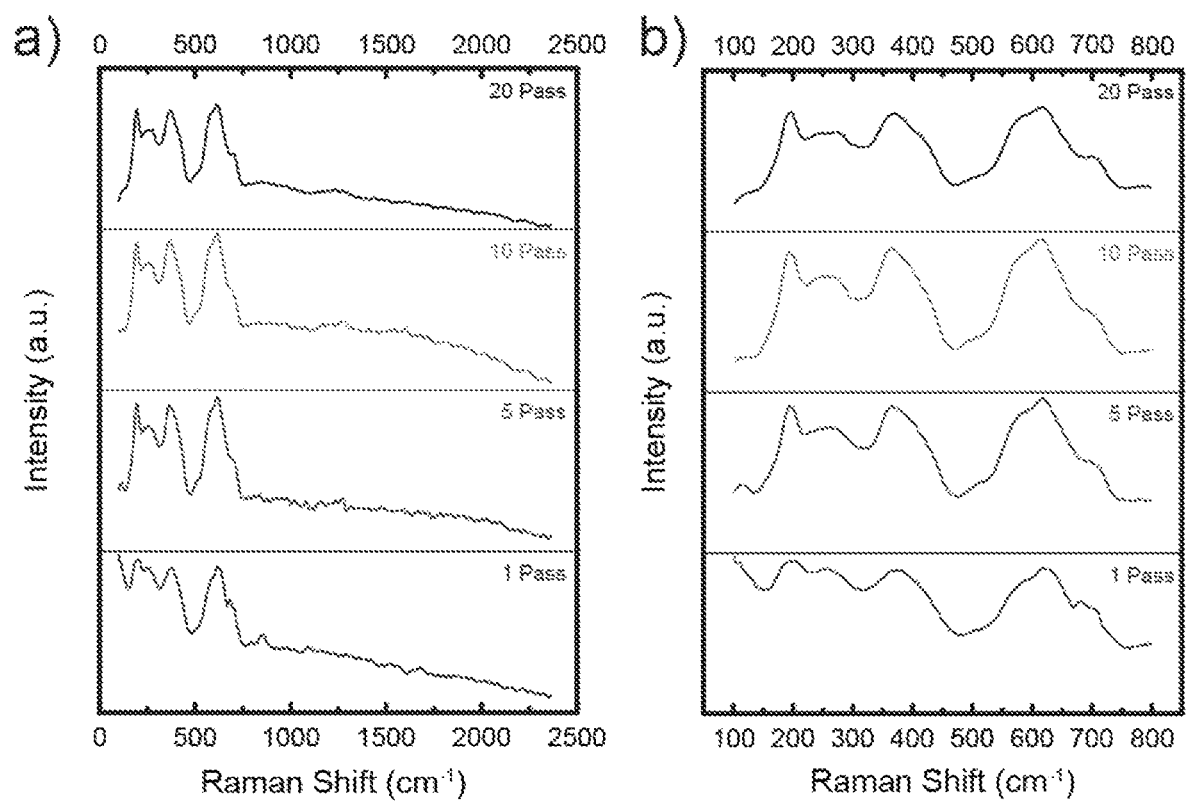

FIG. 20 shows a) Raman spectra of MXene lines printed on PET with increasing numbers of passes/cycles. b) Raman spectra of MXene lines printed on PET with increasing numbers of passes/cycles focused on Raman features of MXene sheets.

Figure 21:
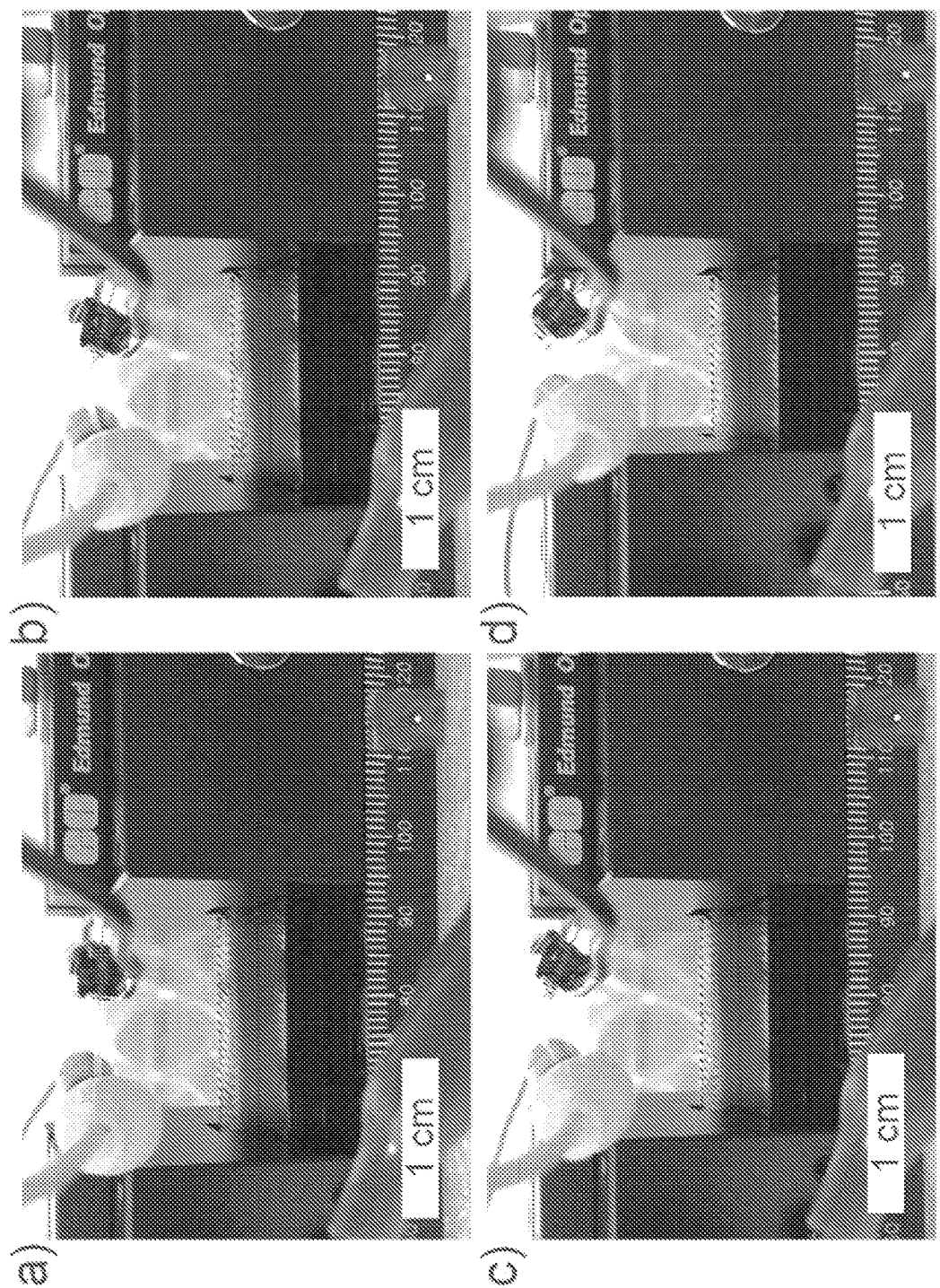
Figure 21:
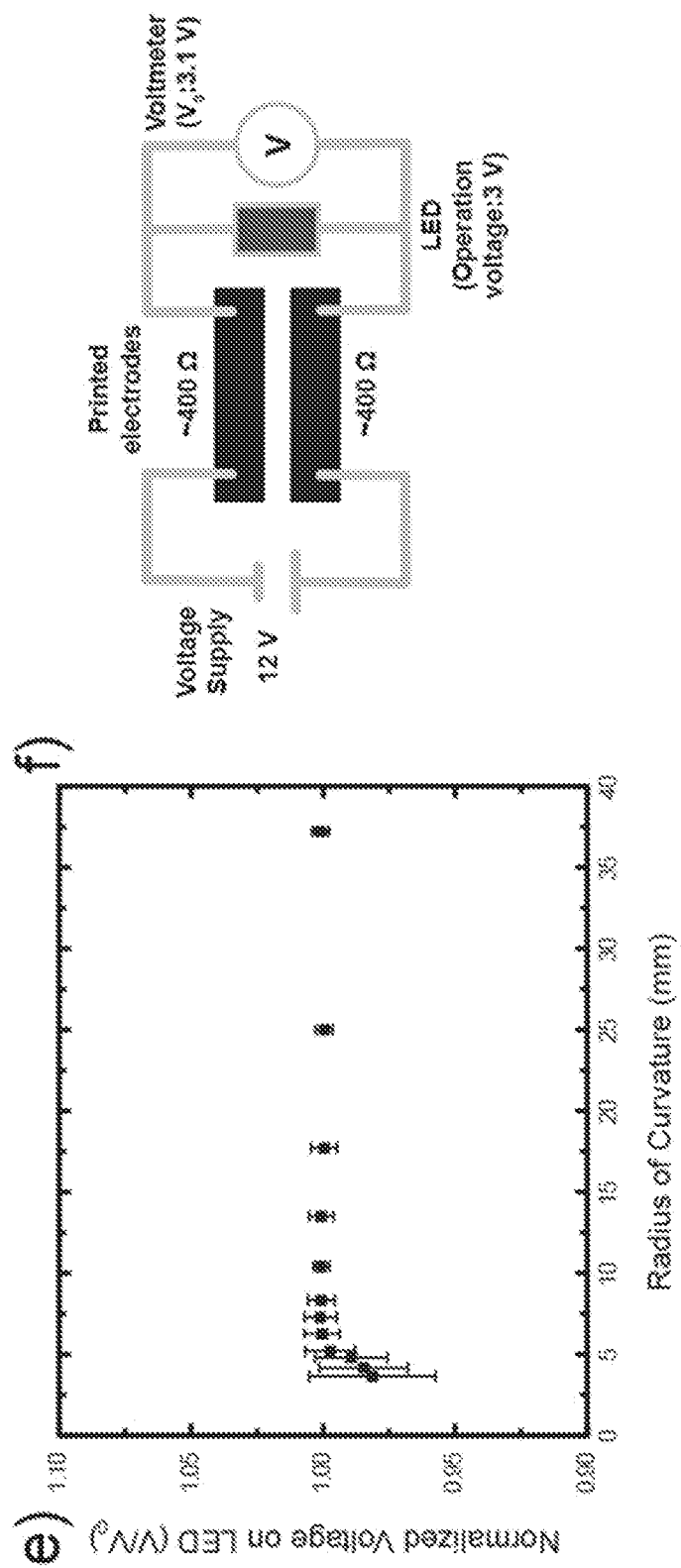

FIG. 21 shows an assessment of conductivity performance of MXene lines printed on PET using ink P5 under bending deformation. Images representing different bending deformation of printed LED circuit under various radius of curvature including (a) 37.5 mm, b) 25 mm, c) 10 mm, d) 5 mm). e) The change in voltage across LED as function of bending radius. Schematic illustration of flexible LED circuit.

DETAILED DESCRIPTION

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all polynucleotide and amino acid sequences described herein. Each RNA sequence includes its DNA equivalent, and each DNA sequence includes its RNA equivalent. Complementary and anti-parallel polynucleotide sequences are included. Every polypeptide disclosed herein includes every polynucleotide sequence that encodes the polypeptides.

The present disclosure provides compositions and methods, aspects of which relate to novel 2D composite materials and methods of making the 2D composition materials.

In none aspect the disclosure relates generally to methods of making the 2D composition materials via vacuum deposition techniques, including but not limited to vacuum assisted solution assembly (VASA), as further described below. Thus, in embodiments, the disclosure comprises using vacuum suction to evacuate a solution to deposit and/or assemble the 2D composition. In this approach, any suitable porous membrane can be used, examples of which will be apparent to those skilled in the art when given the benefit of this disclosure, and are described further below, and in the Figures and Examples of this disclosure.

In another embodiment, the 2D compositions are formed by printing. For example, conventional inkjet printing devices and methods are adapted for forming the 2D compositions as further described below, and in the Figures and Examples of this disclosure. In particular, the present disclosure demonstrates inkjet printing of two-dimensional titanium carbide (MXene) that have unexpected properties, and are highly versatile. In non-limiting embodiments, MXene layers exfoliated in Dimethyl sulfoxide (DMSO) solution provide a preferred basis for generating printable inks once supported with tandem repeat protein binders, non-limiting examples of which are provided below. The resulting ink formulations can be effectively printed on many substrates including paper, glass, polyethylene terephthalate (PET), and Poly(Methyl Methacrylate) (PMMA) to generate electrode patterns with high electrical conductivity. The electrodes printed on flexible PET substrates remains intact and maintain their electrical properties under bending deformation. In addition, the electrical properties of patterned electrodes can be modulated reversibly using changes in humidity, which expands the spectrum of applications of these 2D inks.

In particular embodiments, the disclosure includes compositions comprising or consisting of the 2D composite materials described herein, and includes methods for making the compositions, and methods of using the compositions. Articles of manufacture that contain the 2D composite materials are also encompassed in this disclosure. In non-limiting implementations the disclosure provides compositions of matter suitable for use in a diversity of next generation electronic, optical, and mechanical devices and materials, and in non-limiting embodiments are used in any of photovoltaics, semiconductors, and electrodes. The disclosure provides demonstrations of atomistically precise control of interlayer distances of 2D composite materials using structural protein based materials described further below, in layered composites that contain 2D inorganic materials, non-limiting demonstrations of which are provided using graphene oxide and two-dimensional titanium carbide (MXene), with multiple alternatives available and discussed below.

In general, the 2D composite materials of this disclosure have fully tunable dimensions, including but not necessarily limited to length and thickness. In certain examples a single organic layer of a 2D composite exhibits a thickness of from 0.5 nm-10.0 nm, inclusive and including all numbers to the second decimal point there between. The thickness can be varied by, for example, selecting an organic material (i.e., a protein as more fully described below) with a desired molecular weight, where generally the higher molecular weight the greater the thickness. In embodiments, the organic layer of a 2D composite exhibits a thickness of from 0.5 nm-1.0 nm. There is no particular limit to the number of layers a 2D composite of this disclosure can have.

In one embodiment, a 2D composite material comprises only 2 layers, i.e., one organic (protein) layer, and one inorganic 2D layer. In certain aspects the inorganic layer and the organic layer each have a thickness of about ~0.5 nm, thus placing a smallest thickness for a 2D composite at about 1 nm. In an embodiment the organic layer comprises or consists of a thickness of 0.5 nm-1 nm. In embodiments, either or both layers of a 2D composite consisting of only two layers may have a total thickness of about 2 nm. In embodiments, a 2D composite comprises between 2 and $10^9$ layers. One non-limiting embodiment of the disclosure is illustrated by the SEM image in FIG. 10, which depicts a ~20 micron thick cross section, which corresponds to approximately 10,000 (=$10^4$ layers). In embodiments, a 2D layer comprises heterostructures or compounds.

The area that any particular 2D composite of this disclosure is also not particularly limited, and in certain embodiments is governed only by the capability to produce the 2D inorganic layer. In embodiments, the layer thickness of printed structures can be controlled by controlling the number of layers as well as the distance between adjacent droplets during printing.

In embodiments, graphene layers can be produced in layers, or films or the like, in large areas of up to and exceeding >$1m^2$. It is known in the art that such surfaces are not necessarily single layers, but are assembled from so-called "flakes" that can generally range from 10 nm to 10 microns in length and width, and may be arranged contiguously with one another. Individual flakes can be made from 10 nm to 10 microns in width using for example, exfoliation mechanically or in solution, or vacuum deposition techniques that are well known in the art. The organic layers discussed below can be assembled on top and iteratively on 2D inorganic layers using a variety of approaches. The layers of the 2D composites can be created and assembled using a variety of approaches known to those skilled in the art, given the benefit of this disclosure. In certain embodiments, the disclosure comprises fabricating a sheet comprising a 2D molecular composite and organic layer (i.e., a protein layer) is introduced by solution casting, or by printing as described below.

In certain embodiments, the protein may diffuse into the 2D layers or, for example, adhere to the edges of 2D-flakes to increase inter layer distance. One approach as further described herein comprises vacuum assisted solution assembly (VASA). Generally, such approaches involve use of vacuum suction to evacuate the solution, and any suitable porous membrane, including but not limited to isotropic ceramic membranes formed from, for example, self-organized nanoporous alumina (also known as Anodic Aluminum Oxide or AAO). Non-limiting examples of this approach are described below.

The organic materials comprise in part repetitive proteins that are used to provide precise control of molecular morphology at nanoscale. This approach make use of several advantages of proteins over conventional polymers: (i) protein chain length, sequence, and stereochemistry can be easily controlled to achieve morphology control; (ii) the molecular structure of proteins is well-defined, which is an useful for controlling physical responses; (iii) proteins provide a variety of functional chemistries for conjugation of 2D layered systems, and (iv) proteins can be designed to exhibit a variety of phase transition (e.g. helix to coil transition to tune interlayer distances of 2D materials in real time). Thus, in various embodiments the present disclosure provides for the synthesis and fabrication of 2D-molecular composites comprising layers of crystalline inorganic materials and layers of semi-crystalline organic materials. In embodiments the crystalline inorganic materials can comprise or consist of a single layer of atoms. In embodiments, the layers of semi-crystalline organic material can comprise or consist of self-assembling repetitive proteins as described further below.

In certain implementations the 2D composite materials of this disclosure are provided in essentially planar sheets, wafers, and the like, without being integrated and/or formed into any particular 3D structure or device. In other embodiments the 2D composite materials can be integrated into a wide variety of 3D shapes, and articles of manufacture. In this regard, the disclosure demonstrates the ability to use the organic layer (i.e., protein) interfaces in contact with 2D materials to control interfacial chemistry, electrical contact resistance, and thermal boundary resistance, which are all nanoscale characteristics that are important to the operation of a variety of flexible 2D devices that can be made from or otherwise incorporate composites of this disclosure. Examples of such articles include but are not necessarily limited to actuators, including so-called "soft" actuators which have a variety of applications in medicine, health care, wearable devices, manufacturing, and robotics, and more generally into any of a wide variety of textiles. With respect to actuators, in general it is considered that soft actuators are made of soft or flexible material, and are thus distinct from conventional actuators which are typically rigid and are limited in degrees of freedom.

In embodiments, one or more soft actuators of this disclosure are used as artificial muscles, cell scaffolds, micromanipulators (such as molecular tweezers), robots, lenses, smart transforming sheets, in drug delivery compositions and devices, and in sensors, for example sensors that can detect thermal, biological, chemical stimuli, and/or combinations thereof. In embodiments, the same applies to printed layers.

In general, an "actuator" as used herein is an article that moves, i.e., flexes or otherwise changes its shape, in response to a stimulus. Thus, an actuator can be a component of a machine that requires movement, wherein the actuator supplies the movement, and/or contributes to the movement of another component. It is generally considered that when a stimulus is received, the actuator responds by converting energy into mechanical motion. The stimulus can comprise heat, a magnetic field, mechanical and/or pneumatic pressure, an electric field/current, a light source, or a chemical signal. In one embodiment, an actuator of this disclosure converts thermal energy into mechanical movement. In embodiments, an actuator of this disclosure responds to a control signal to convert an energy source into movement. In embodiments the movement can comprise, for example, a change in shape, such as forming a curvature in a 2D composite of this disclosure.

In embodiments, at least one inorganic layer of a 2D composite of this disclosure comprises a 2D-allotrope, a 2D-compound, or any combination thereof. The elemental (allotrope) 2D materials are typically identified by an -ene suffix, whereas the compounds are typically identified by -ane or -ide suffixes. Layered combinations of different 2D materials of this disclosure may comprise van der Waals heterostructures.

In non-limiting embodiments the allotropes are selected from Graphene, Graphyne, Borophene, Germanene, Silicene, Stanene, Phosphorene, Molybdenite, palladium, rhodium, and combinations thereof. In non-limiting embodiments the 2D-compounds are selected from Graphane Oxide (GO), Hexagonal boron nitride, Germanane compounds, and Mxenes. In embodiments the 2D compositions comprise transition metal di-chalcogenides (e.g., Molybdenum disulfide, Tungsten diselenide, Hafnium Disulphide). In general, transition di-chalcogenides are atomically thin semiconductors of the type $MX_2$, with M a transition metal atom and X a chalcogen atom (S, Se, or Te.). One layer of M atoms is sandwiched between two layers of X atoms. For example, a $MoS_2$ monolayer has a thickness of about 6.5 Å.

It is generally considered that bulk physical properties of the molecular composites of this disclosure can be altered using structural change originating from a systematic increase in the molecular weight of the organic layer, which may be comprised of semi-crystalline organic material, such as any of the proteins described herein. With respect to the semi-crystalline organic materials, i.e., self-assembling repetitive proteins, the disclosure includes methods for making such proteins and incorporating them into the 2D composite materials described herein. In certain aspects the semi-crystalline organic materials comprise amino acid sequences that may be at least in part are based on naturally occurring proteins, but can be modified such that the polypeptides have distinct properties relative to their naturally occurring counterparts. The disclosure includes 2D composite compositions wherein the semi-crystalline organic materials comprise homogenous polypeptide populations, meaning all the polypeptides in the composition share the same primary amino acid sequence, and also includes heterogeneous polypeptide populations, meaning the compositions comprise combinations of distinct polypeptides with different primary amino acid sequences. Additional description of the organic materials used in the 2D composites is provided below.

In embodiments, the polypeptides used in the semi-crystalline organic material portion of 2D materials provided by this disclosure differ from their natural counterparts by at least one property, such as having a distinct primary amino acid sequence, and/or a distinct modulus value. In embodiments, the modulus value that differs from a naturally occurring counterpart is a tensile modulus, an elastic modulus, a bulk modulus, or a shear modulus. In embodiments, polypeptides used in a semi-crystalline organic material component of a 2D material of this disclosure are made such that they comprise ordered and disordered domains which contribute favorably to their mechanical properties. In embodiments, one or more semi-crystalline organic material component of a 2D composite of this disclosure is identified and/or generated via production and screening of random protein libraries having member polypeptides that are modifications of naturally occurring proteins. By screening such libraries, those polypeptides with desirable properties that are related to the size and distribution of their crystalline and amorphous regions can be generated, identified, modified further if desired, and produced recombinantly. In embodiments, modifying the proteins, such as to produce a library for screening, comprises varying length of amino acid content in beta-sheet crystalline/ordered regions, or varying the length of Gly-rich amorphous region (e.g. segmented copolymer morphology depends on volume fractions), or varying the size of the repeating unit (amorphous+crystalline, "n") to modulate the molecular weight of the protein, or combinations thereof. In embodiments, the modifications comprise altering a crystal-forming polypeptide sequence (also referred to herein as the crystallite-forming subsequence or crystalline sequence or crystal domain) so that the wild-type amino acid is replaced with A, S, T, V, L, or P.

In embodiments, screening polypeptides comprises expressing the polypeptides recombinantly in a prokaryotic expression system, such as *E. coli*, selecting separate cultures each expressing distinct polypeptides, placing a plurality of samples of the cultures in separate sample test chambers, and subjecting the samples to a means of identifying protein structure in the samples, such as by chromatography, calorimetry, mass spectroscopy, IR or Raman spectroscopy, microscopy and X-Ray Diffraction (XRD), to obtain information on the protein structure, such as backbone and h-bond directions. It will be recognized that this approach is readily adaptable to high-throughput techniques. Once the protein information is obtained and analyzed, the stock clones can be grown, and the proteins likely to have desirable properties can be produced recombinantly and used for including in a 2D composite material of this disclosure. Thus in one approach, the present disclosure comprises providing a template protein, generating a plurality of modified versions of the template protein, screening the plurality of modified polypeptides for crystalline and amorphous regions, selecting modified polypeptides with crystalline and amorphous sequences that are likely to impart desirable mechanical properties to the polypeptides, producing the selected polypeptides recombinantly, and incorporating the polypeptides into a 2D composite material of this disclosure.

Also included in this disclosure are all amino acid sequences provided herewith, all polynucleotide sequences encoding the amino acid sequences, expression vectors encoding the polypeptide sequences, cells comprising the expression vectors, cells and cell cultures comprising the proteins expressed by the expression vectors, and cell media containing or separated from such cell cultures, to the extent they are used in making and/or using the 2D composite materials.

In certain approaches the disclosure includes a database comprising at least one of the crystal-domain amino acid sequences (also referred to herein as crystallite-forming subsequences), and/or at least one of the amorphous-domain amino acid sequences (also referred to herein as amorphous subsequences), provided herein. Amino acid sequences capable of forming crystal domains and amorphous domains are provided. Those skilled in the art will recognize that the crystallite and amorphous sequences can be selected from the database for use in the 2D composite materials of this disclosure. In this regard, the database may be searchable, and may be configured to be searchable based on an input query, such as a query designed to identify and/or generate amino acid sequences that are capable of forming crystal-domains, amorphous-domains, and combinations thereof, and for other attributes, including but not necessarily limited to 2D morphology, length, thickness and other parameters that are used to create and/or tune the 2D composites of this disclosure. The database can be configured to be searchable for one or more amino acid sequences for incorporating into a polypeptide or a population of polypeptides based on inputting any desirable properties, including but not necessarily limited to the physical length of the domains that are capable of forming. The database may be a component of a system in which the database is stored on a storage device in communication with a processor. The storage device can comprise any suitable storage medium, including but not necessarily limited to digital files, and may provide access to cloud-based files, etc. The system can include a computer program comprising an algorithm to facilitate database searching. The computer program may be configured to identify, retrieve and/or generate one or more polypeptide sequences that comprise a motif pattern of, for example, $(ca)_n$, $(ac)_n$, $a(ca)_n$, or $(ca)_n c$, wherein c is a crystal-forming domain block and a is an amorphous domain block, and n is the tandem-repeat number, and is an integer from 1 to 100, inclusive, and including all ranges of integers there between, and can be configured to generate polypeptides with any desirable dimensions, or other properties, such as electrical conductance, electrical resistance, etc.

In another approach the disclosure includes a method of making a synthetic or recombinant polypeptide for use in a 2D composite of this disclosure. A synthetic polypeptide is made without cell based translation systems. A recombinant polypeptide is made using cell based translation systems. The polypeptide contains segments capable of forming at least a first crystal-forming domain block and at least a first amorphous domain block. The method comprises selecting an amino acid sequence that is capable of forming the first crystal domain block, wherein the crystal domain block is from about 2 nm to about 5 nm long and comprises from 10 to 30 amino acids, and selecting an amino acid sequence that is capable of forming a first amorphous domain block, wherein the first amorphous domain block can comprise from 10 to 60 amino acids, and forming the synthetic polypeptide by incorporating the amino acid sequence that is capable of forming the first crystal-forming domain block and the sequence that is capable of forming the second amorphous domain block into the synthetic or recombinant polypeptide. Embodiments further comprise incorporating at least a second crystal-forming domain block, or at least a second amorphous domain block, or a combination thereof, into the single polypeptide. In certain approaches the method includes incorporating into the polypeptide: i) the first and second crystal-forming domain blocks each comprising the same amino acid sequence as each other; or ii) the first and second crystal-forming domain blocks each comprising distinct amino acid sequences from each other; or iii) the first and second amorphous domain blocks each comprising the same amino acid sequence as each other; or iv) the first and second amorphous domain blocks each comprising distinct amino acid sequences from each other. Those skilled in the art will recognize that additional domain blocks can be included according to the aforementioned $(ca)_n$, $(ac)_n$, $a(ca)_n$, or $(ca)_n c$ configuration. Blocks may also be referred to as subsequences.

In embodiments, selecting the amino acid sequence that is capable of forming the first crystallite-forming subsequence, and/or selecting the amino acid sequence that is capable of forming the first amorphous subsequence, or a combination thereof, comprises selecting an amino acid sequence from a database of amino acid sequences that comprise at least one sequence that comprises or consists of a sequence selected from the sequences in Table 5 and/or Table 6, and includes selecting sequences wherein between 1 and 4 amino acids in those sequences are altered, or wherein those sequences include an insertion or a deletion.

In non-limiting embodiments, the proteins of this disclosure are processed to form a layer of a 2D composite material of this disclosure, and may therefore be generally planar, but other geometries are not necessarily excluded from the disclosure. In various embodiments, the organic component of a 2D composite material can comprise additives, such as a plasticizer. In embodiments, the disclosure includes forming powder comprising or consisting of a polypeptide by dissolving the polypeptide in a polar solvent and casting via the evaporation of the polar solvent using vacuum based methods, or by printing.

Some non-limiting embodiments of the present disclosure are illustrated using an anatomical feature of squid that is referred to in the art as Squid Ring Teeth (SRT), and a wide variety of derivatives thereof. However, it will be recognized by those skilled in the art that any other naturally occurring protein that has desirable properties such that they are candidates for analysis and modification according to this disclosure can also be used. Such proteins include but are not necessarily limited to silks and other boil-elastomers.

As discussed above, organic layers of the 2D composites of this disclosure can include polypeptides comprising at least two repeats of crystallite-forming subsequences and an amorphous subsequence. The amorphous subsequence is located between the crystallite-forming subsequences. The polypeptide can comprise a plurality of alternating crystallite-forming subsequences and amorphous subsequences. The polypeptide can also comprise other sequences—such as sequences derived from cloning. The sequences derived from cloning may be present as repeats. Although the amorphous subsequences are intervening between crystallite-forming subsequences, they do not necessarily need to be between two crystallite-forming subsequences. For example, an amorphous subsequence can flank a crystallite-forming subsequence at one end (C or N terminal) only. The length and makeup of crystallite-forming subsequences is such that it can provide hydrogen bonding with another crystallite-forming subsequence within the same polypeptide to result in ordered structures (such as beta sheet structures). The beta sheet structures can be stacked. The intervening amorphous subsequences provide flexibility between the crystallite-forming subsequences in the form of turns so that crystallite forming subsequences can be in close proximity with each other so as to be able to form hydrogen bonds—resulting in ordered structures. The resultant polypeptide can have semi-crystalline properties.

The amorphous subsequence allows the formation of a network of hydrogen bonds—within the same amorphous subsequence or with different amorphous subsequences. The ordered stacked beta sheet formations of the crystallite-forming subsequences and the network of hydrogen bonding of the amorphous subsequences provides for a supramolecular structure of the organic component of the 2D composite materials. The supramolecular polypeptides exhibit self-healing properties. These molecules can recover their structural and functional properties following disruption. This is attributable, at least in part, to the network of hydrogen bonding of the amorphous subsequences.

The crystallite-forming and amorphous subsequences contribute to the mechanical properties of the 2D composite. For example, a crystalline index of the polypeptide layer can be from 0 to 60%. For example, the crystalline index of the polypeptide can be from 1 to 60% (including all percentage values there between). In one embodiment, the crystalline index is from 30 to 50%. It will be recognized that the crystalline index is related to the sequence as well as the physical or chemical process.

The crystallite-forming subsequence in the organic layer can be from about 2 nm to about 5 nm. This roughly corresponds to 10 to 30 amino acids. Thus, the crystallite-forming subsequence can have from 10 to 30 amino acids. For example, the crystallite-forming subsequence can have from 15 to 25 amino acids. Generally, amino acids that are known to be capable of participating in hydrogen bonding leading to ordered structures like beta sheet formation are preferred. Such amino acids include histidine, threonine, valine, alanine, serine and the like. Non-limiting examples of crystalline and amorphous segments of a segmented copolymer of this disclosure is presented in the Figures and Examples of this disclosure. For example, one non-limiting example of a crystallite-forming subsequence is shown in FIG. 3b, where the sequence is AA[XXXXXX]HH. The bracketed portion can comprise a variable AVSHT sequence. The variable sequence can be a series of Alanines, such as from one to six or more Alanines, followed by, for example, one or more Serine, Histidine or Thymine, followed by Histidines. The length of the bracketed portion is variable.

The amorphous subsequence can be a glycine-rich sequence. The amorphous subsequence can assume different conformations. For example, it can be present as a random coil, a helix, or as a psi chain. It can comprise from 10 to 60 amino acids. For example, it can comprises from 10 to 56 amino acids. In addition to contributing to mechanical and other properties of the polypeptide, the amorphous subsequence also serve to connect the crystallite-forming subsequences.

The organic layer of the 2D composite can have various arrangements of the crystallite-forming subsequences (c) and the amorphous subsequences (a). For example, the present disclosure provides organic layers with an amino acid sequence of the form $(ca)_n$, $(ac)_n$, $a(ca)_n$, or $(ca)_n c$, wherein c is a crystallite-forming subsequence and a is an amorphous subsequence, and n is the tandem-repeat number, is an integer from 1 to 100, inclusive, and including all ranges of integers there between. For example, it can have from 4 to 20 repeats (including all integer values therebetween). The crystallite-forming subsequence can be derived from a naturally occurring bio-elastomer, such as SRT, and the amorphous subsequence can be derived from a naturally occurring bio-elastomer protein. In embodiments, compositions comprising a polypeptide comprising a sequence of the form $(ca)_n$, $(ac)_n$, $a(ca)_n$, or $(ca)_n c$, where c is a crystallite-forming subsequence, a is an amorphous subsequence derived from a bio-elastomer protein, and n, the tandem-repeat number, is an integer from 1 to 100, inclusive, and including all ranges of integers there between. $(ca)_n$, $(ac)_n$, $a(ca)_n$, or $(ca)_n c$ can be similar or identical to a block (e.g. repeating units are same) or segmented (e.g. repeating units are different) polymer or co-polymer.

In one embodiment, the crystallite-forming subsequence c contains one or more amino acid substitutions in which the wild-type amino acid is replaced with one of the following amino acids: A, S, T, V, L, P. The disclosure includes combinations of such substitutions.

In one embodiment, the crystallite-forming subsequence and the amorphous subsequence are derived from SRT proteins from any of the following species: *Loligo vulgaris, Loligo pealei, Todarodes pacificus, Euprymna scolopes.*

In embodiments, the crystallite-forming subsequence c exhibits at least 50%, and up to 100% sequence identity, inclusive and including all integers and ranges there between, to a sequence identity to a sequence from Table 5, and/or the amorphous subsequence a exhibits at least 50% sequence identity, and up to 100% sequence inclusive and including all integers and ranges there between, identity to a sequence from Table 6 that contains Glycine rich sequences. Alternatively amorphous subsequences could be engineered synthetically based on amorphous known repeating structural domains such as beta-spiral $[GPGXX]_n$, linker $[GP(S,Y,G)]_n$ or 310-helix $[GGX]_n$, or any combinatorial combination of these unitys, where n, is an integer from 1 to 100, inclusive, and including all ranges of integers there between, and X is typically A, S, V, T, Y amino acids or any combinatorial combination of these amino acids.

In embodiments, one or more polypeptides of this disclosure for use in a 2D composite are formed into a powder, such as by dissolving the polypeptides in a polar solvent and casting via the evaporation of the polar solvent. In embodiments, polypeptide powder is formed or modified by heating to between 32° C. and 195° C. inclusive, and including all integers and ranges there between, and subjecting to a pressure treatment, such as a pressure treatment between 1 kPa and 1 GPa, inclusive and including all integers and ranges therebetween. In embodiments, a plasticizer is included in the process. Suitable plasticizer include, but are not limited to, water, glycerol, 1,4-Butanediol, Dibutyl tartrate, Dibutyl phthalate, Lactic acid, Octanoic acid, Plamitic acid, Sorbitol, Sucrose, and diacetyl tartaric acid ester of monodiglycerides (DATEM).

In embodiments, the disclosure includes processing an organic layer alone or as a component of a 2D composite of the disclosure by forming an adhesive, self-healing, or cohesive layer techniques. In embodiments, the disclosure comprises forming a film, fiber, ribbon, colloid, capsule, ribbon or tube made partially or fully from the organic layer, or the entire 2D composite materials.

In embodiments, a composition of this disclosure comprises or consists of or is an electronic conductor, or a semi-conductor.

Figure 1:
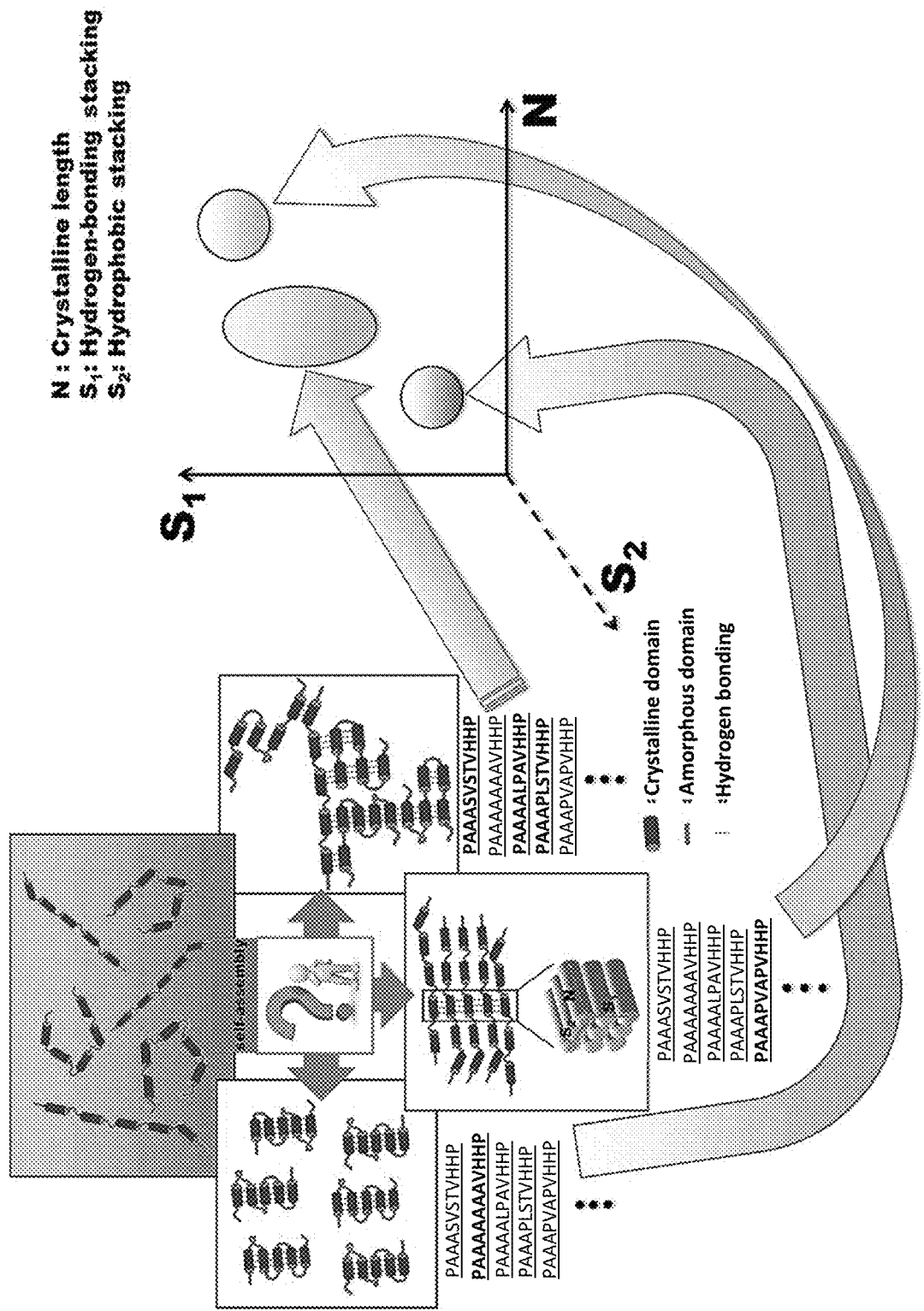
FIG. 1 shows mapping of protein sequences to ordered structures for structural proteins. Amino acid modifications in ordered domains will affect intermolecular and intramolecular stacking of β-sheet formation. The amino acid sequences shown are.

In illustrative and non-limiting embodiments, the disclosure provides synthetic peptide sequences built based on de novo design of thermoplastic SRT proteins. SRT proteins have amorphous and ordered domains. Based on preexisting SRT ordered templates, our approach to 2D composites takes advantage of new protein sequences, which directly correlate to crystal properties (FIG. 1). The approach is adaptable to other proteins and can be used accordingly by those skilled in the art, given the benefit of the present disclosure.

In certain aspects embodiments of this disclosure comprise 2D composite materials that comprise or consist of molecular sheets, and folding such sheets into, for example, fibers, which may be similar to fiber optic wires.

In embodiments, the disclosure provides printing-based approaches. In this regard, the significance of printing technologies for development and fabrication of novel electronic, photonic, and energy storage devices is increasing rapidly with the expansion in the set of available materials for printing. Inkjet printing includes the positive aspects of printing techniques including compatibility with various substrates including flexible and soft surfaces, low operation temperatures, and the ability to generate large area patterns. In addition to these features shared by other printing techniques, inkjet printing offers additional advantages such as controlled material deposition, rapid multi-material processing, maskless and high resolution (~60 μm) digital patterning capability. Even though, the material spectrum for inkjet printing spans many polymers and nanomaterials, without intending to be constrained by any particular view, it is believed this is the first disclosure whereby printing is employed using 2D crystals.

In embodiments, the disclosure provides printing-based approaches. In this regard, the significance of printing technologies for development and fabrication of novel electronic, photonic, and energy storage devices is increasing rapidly with the expansion in the set of available materials for printing. Inkjet printing includes the positive aspects of printing techniques including compatibility with various substrates including flexible and soft surfaces, low operation temperatures, and the ability to generate large area patterns. In addition to these features shared by other printing techniques, inkjet printing offers additional advantages such as controlled material deposition, rapid multi-material processing, maskless and high resolution (~60 μm) digital patterning capability. Even though, the material spectrum for inkjet printing spans many polymers and nanomaterials, without intending to be constrained by any particular view, it is believed this is the first disclosure whereby printing is employed using 2D crystals. In connection with this, prior to the present disclosure, there were several key issues that remained unaddressed for developing functional inks of, for example, 2D inorganic materials that are suitable for inkjet printing, including but not necessarily limited to low viscosity of water based solvent systems, improper adhesion of crystals to substrate and formation of coffee ring effect during solvent evaporation. The low viscosity of water based solvents employed to stabilize, for example, exfoliated MXene sheets, can hinder the stability of jetting process leading to formation of satellite droplets and jetting deflection. Moreover, MXene sheets, and other 2D inorganic material sheets, can accumulate at the edges of the droplets (Coffee ring effect) during evaporation due to lack of interactions with the substrate. This lack of interaction can also lead to redispersion of deposited materials during printing cycles. Similar problems were addressed for other 2D crystals including molybdenum disulfide, and tungsten disulfide using a binder molecule, which can help increasing viscosity of the ink and facilitating specific interactions between MXene sheets and substrates. However, commonly used binder molecules synthesized through chemical routes cannot offer a versatile solution for establishing and controlling sheet-to-sheet and sheet-to-substrate interactions for MXenes. In contrast to chemical binders, the present disclosure includes use of proteins as an improved composition for use with 2D inorganic materials, including but not limited to Graphene, Graphyne, Borophene, Germanene, Silicene, Stanene, Phosphorene, Molybdenite, Graphane Oxide (GO), Hexagonal boron nitride, Germanane compounds, Methyl Oxides, Methyl Carbides, Methyl nitrides, transition metal oxides, and transition metal di-chalcogenides, and combinations of such compounds. In embodiments, the 2D inorganic material comprises or consist of few atoms thick layers of transition metal carbides, nitrides, or carbonitrides, sometimes referred to as MXenes. Such inorganic 2D compounds and proteins described herein can each form strong hydrogen bonding interactions. Accordingly, and again without intending to be bound by theory, it is considered that prior to the present disclosure the interaction and assembly dynamics of certain 2D inorganic compounds and proteins was unexplored.

In embodiments, compositions of this disclosure are made without use of a vacuum. In embodiments, a composition and/or method of the disclosure excludes formation of a so called "coffee ring" which is an effect of solvent drying as a function of ink viscosity and solute transport via motion of a solvent. Thus, in various embodiments the present disclosure comprises inks, wherein the inks comprise materials described herein that are capable of being layered, as well as layered materials comprising or consisting of the inks, methods of making the inks, methods of printing using the inks, and the printed materials and devices made entirely of the inks, or having the inks impregnated therein, or 3D articles coated with inks of this disclosure. In embodiments, a composition of this disclosure thus comprises a printable conductive ink. In embodiments, a composition of this disclosure comprises, consists of, or is printed on, coated or otherwise applied to a flexible electronic device, including but not necessarily limited to touch screens, electronic paper, sensors, radio frequency tags, photovoltaic cells, light-emitting diodes and electronic textiles. In embodiments, inks of this disclosure are made such that they do not produce unsatisfactory printing, such as incomplete printing or damage to the printing apparatus, such as by obstructing a printing nozzle. In embodiments, a composition of this disclosure is used in thermal, energy, optical, radio frequency, electronic and/or optoelectronic applications.

In an aspect, the disclosure provides a closed vessel containing the proteins and solvents and one or more conductive 2D-layered materials in a form that is suitable for printing. The vessel can be, for example, a disposable or reusable ink cartridge. Thus, the disclosure includes devices and systems for making compositions of this disclosure.

In an embodiment, the present disclosure thus provides a method for forming a composition of this disclosure which comprises the steps of combining one more proteins as described herein with one or more solvents, and one or more conductive 2D-layered materials, such as MXenes, and depositing the composition on a substrate in a desired pattern or print. In one aspect, the step of depositing the composition onto a substrate comprises using a printing technique, including but not limited to lithographic, extrusion-based, droplet-based (such as inkjet, micro-valve, acoustic, electrohydrodynamic printing) or laser-based techniques (such as laser-assisted printing, laser-induced forward transfer, matrix-assisted pulsed laser evaporation). In embodiments, the composition that is used in, for example, a printing technique, comprises a specific concentration of protein, or falls within a specific protein concentration range. In embodiments, the relative amounts of proteins, 2D inorganic materials, and solvents are determined using, for example, using the Ohnesorge number (Oh), which is known in the art as a dimensionless number that relates viscous forces to inertial and surface tension force. The formula for calculating the Oh number for compositions of matter is well known in the art. In embodiments, for inkjet compositions, important variables include viscosity $\eta$, scale length, such as nozzle diameter given as l, density $\rho$ and surface tension $\sigma$. A formula that can be used for determining relative amounts of components of the materials of this disclosure is: $Oh=\eta/\sqrt{(l \times \rho \times \sigma)}=Viscosity/\sqrt{(inertia \times surface\ tension)}$. In embodiments, such as inkjet printing liquids described herein, exhibit a Z range of 1<Z<20, where Z is the reciprocal of the Ohnersorge number.

A wide variety of substrates can be used with the compositions and methods of this disclosure. As described herein, the substrates can be flat, stiff, flexible, rough, smooth, or patterned. Examples of suitable substrate materials include cellulosic materials (e.g., paper, cardboard etc.—coated or uncoated, wood), polymer substrates (e.g., plastics, PET, and acrylic), glass, metals, silicon, quartz, or any other suitable substrate known in the art. In an embodiment, the substrate is paper. In another embodiment the substrate is a textile, and thus may comprise a fabric of any known type. Combinations of substrates may be used. In various embodiments, the present disclosure provides substrates onto which a composition of the disclosure has been deposited.

In embodiments the disclosure comprises one or more 2D layers, which are layers that comprise one or more polypeptides described herein, and one or more other compositions of matter, such as allotropes described herein. In one non-limiting embodiment, the additional composition of matter comprises a 2D transition metal selected from a carbide, carbonitrides and nitrides, metal oxides. It will be recognized that such 2D layers can be used to form, be printed on, or to coat a wide variety of 3D articles, as described further herein.

In embodiments, a composition of this disclosure comprises or is in communication with a sensor that, for example, may comprise any suitable component for detecting any signaling moiety or other type of signal. In embodiments, the sensor comprises a biological sensor. In embodiments, the sensor comprise an electronic sensor. In embodiments, a sensor comprises a transducer or detector element, which can include but is not limited to optical, piezoelectric, and electrochemical functions. In embodiments a composition of this disclosure is comprised by a biochip. In embodiments, a composition or article of manufacture of this disclosure is in communication with an electrical stimulation component. A composition, device or system of this disclosure can be connected to a computer and/or microprocessor such that the composition can be structurally altered in response to a signal. Systems comprising such computers and/or microprocessors in communication with a device and/or a composition of this disclosure are included within its scope. In embodiments, a device and/or system or composition of this disclosure is configured to be capable of WiFi or Bluetooth communication with another component that can, for example, control one or more properties of the composition, including but not limited to electrical conductance and/or an actuator function. In certain embodiments, the disclosure includes as a component of a device or system that is in communication with a composition of this disclosure a non-transitory computer readable storage media for use in performing an algorithm to control, for example, actuator or other functions. In certain embodiments a device and/or system of this disclosure comprises microprocessor, wherein the microprocessor is a component of an Arduino board, and wherein the device may further comprise a suitable Arduino WiFi shield. In embodiments, a device of this disclosure is provided as an implantable device, or is integrated into or coated onto a wearable garment or a wearable device.

The following specific examples are provided to illustrate the invention, but are not intended to be limiting in any way.

Example 1

SRT proteins from *Loligo vulgaris* were identified using a next generation sequencing approach and transcriptome assembly (FIG. 3a). A segmented block is selected for tandem repeat construction strategy (FIG. 3b). Randomized gene libraries based on the block segment were designed and implemented as a combinatorial plasmid library by PCR and ligation. FIG. 3c shows the amplification strategy for producing tandem repeats the desired length, N, of the library members (e.g., DNA and protein gels for N=13 are shown in FIG. 3d). A description of a combinatorial library of crystalline-region variants is given below for the polypeptide termed SynE3.

Example 2

Tunable mechanical properties are one of the key challenges for product development. Protein-based materials modified according to the present disclosure for including in 2D composite materials provide a solution to this problem due to the ease of molecular scale engineering. In fact, it is known that the toughness of semi-crystalline proteins increases with respect to number of β-sheets. Notably, fibrous proteins (e.g., silk and SRT proteins) contain hard and brittle crystalline domains and amorphous flexible regions. Each of these functional regions is assembled via hydrogen bonds and van der Waals forces. The backbones of these repeating units neatly align by forming a dense hydrogen bond network, resulting in two-dimensional β-sheets. Multiple β-sheets, in turn align in parallel to form a three dimensional stack of a few nanometers in size. Here, the hydrophobic forces play a major role by keeping the β-sheets together. Native SRT proteins already show considerable diversity (variable AVSTH-rich) in their crystal-forming sequences, and their physical properties vary significantly.

We designed new sequences based on three parameters:
(i) varying length of amino acid content in beta-sheet crystalline/ordered regions
(ii) varying the length of Gly-rich amorphous region (e.g. segmented copolymer morphology depends on volume fraction), and
(iii) varying the size of the repeating unit (amorphous+crystalline, "n") to modulate the molecular weight of the protein.

Thermoplastic processes, used in the plastic industry, are preferred because drying steps could be eliminated; thus reducing their process time. Utilization of extrusion and injection-molding technologies offer the advantages of low cost and versatile production systems. We demonstrated the thermal processing of high-strength recombinant SRT proteins via extrusion, injection molding and hot-press processing. Water is a plasticizer for the recombinant SRT protein. The extrusion process is performed with protein powder. Glass transition temperature for the recombinant protein is 32° C. when the sample is immersed in water (e.g., saturated water content of 24%). Extruded SRT shows an elastic modulus of ~0.4 GPa at room temperature but they are highly brittle and the decrease in the modulus is most likely due to cracks formed during the cooling process at RT. The DMA was repeated after hot-press cycles with increased dynamic elastic modulus to 2 GPa. Unique to SRT, the stiffness value is preserved in both wet and dry conditions even after multiple recycles of the protein. In contrast, other high modulus bioelastomers such as recombinant silk have drastic drops in their elastic moduli for wet conditions due to the swelling and relaxation of non-crystalline domains. The overall strength of intermolecular interactions and their relative intermolecular ordering in SRT give rise to a high-strength material. The shear modulus of a protein network can be calculated as G=νkT, with a contribution of kT per strand. Estimating 2 strands per molecule gives a strand density of ν=0.033–0.044 strands $nm^{-3}$, the shear modulus is calculated as G=νkT=1.55–2.06×$10^5$ Pa, which agrees with the experimental data. This result is significant for thermal processing of recombinant SRT proteins compared to silk, which is very hard (~2 GPa) above its glass transition temperature.

It has been shown that mechanical properties of semi-crystalline proteins changes with respect to size of β-sheets. Using the results of previous work for synthetic spider silk analogs as well as modeling, we can measure the mechanical and rheological properties of selected clones as a function of temperature (i.e., 20° C. to 250° C.) and humidity (i.e., 0-100%).

Example 3

In this example, we developed an alternative tandem-repeat DNA-assembly method to: (i) produce TR sequences of various lengths in a single reaction, (ii) offer better control over the resulting lengths, and (iii) allow pooled processing of unit-sequence libraries. In this approach, long TR products from a short sequence unit are produced by rolling-circle amplification (RCA). The RCA reaction is tuned to incorporate noncanonical nucleotides at random positions. These nucleotides block digestion by key restriction endonucleases; the resulting partial-digestion products can be separated by size and cloned into an expression vector for protein production. This method, which we call "protected digestion of rolling-circle amplicons" (PD-RCA), can be used to prepare a library of TR sequences with a controlled distribution of lengths in a single cloning step.

We applied PD-RCA and recombinant expression in E. coli to produce a panel of artificial SRT-based proteins that vary only in the repeat number, but not in the lengths or compositions of their crystalline and amorphous regions. We demonstrate that the toughness and flexibility of these synthetic SRT-mimics increase as a function of molecular weight while the elastic modulus and yield strength remain unchanged. These results suggest that artificial proteins produced by PD-RCA can help to illuminate the genetic basis of protein material behavior, and that SRT proteins provide a promising platform for the design of new materials with custom properties.

In this example, we used crystal-forming polypeptide sequence PAAASVSTVHHP (SEQ ID NO:29) and the amorphous polypeptide sequence YGYGGLYGGLYG-GLGY (FIG. 4A; SEQ ID NO:182). This unit is one of several possible consensus sequences derived by inspection of the alignments from squid species. We used this unit to construct three TR sequences that differ only by their repeat numbers, and hence by their total lengths. These sequences, with repeat numbers of 4, 7, and 11, are named Syn-n4, Syn-n7, and Syn-n11. Similar to native SRT proteins, these polypeptides comprise ordered crystalline and disordered amorphous domains, which contribute to their mechanical properties.

To construct this panel of TR sequences, we sought a convenient method to produce them simultaneously in a single cloning step (FIG. 4B). Rolling-circle amplification (RCA) generates high-molecular-weight TR products from short, circular DNA templates. We used a strategy similar to the incorporation of 5-methylcytosine (5mC) to facilitate the partial digestion of PCR amplicons, to allow the partial digestion of RCA products, yielding TR sequences of various lengths that could be size-selected and cloned (FIG. 6).

We reasoned that the ratio of 5mC to cytosine in the RCA reaction would control the length distribution of the resulting partial digests. Additionally, the mechanism of RCA precludes the formation of mixed TR products when applied to a pool of template sequences, allowing the construction of pooled libraries. We analyzed cloned TR genes by diagnostic digestion and Sanger sequencing, and then expressed and purified in E. coli by standard methods.

We utilized Fourier-transform infrared spectroscopy (FTIR), X-Ray Diffraction (XRD), and Dynamic Mechanical Analysis (DMA) to characterize the structures of the protein materials. Molecular sizes of synthetic sequences produced by our PD-RCA are listed in Table 1, and the corresponding protein SDS gels are shown in FIG. 5a. These three synthetic polypeptides have molecular weights varying between 15-40 kDa, similar to the polydispersed molecular weight distribution of native SRT complex (i.e., 15-55 kDa). The differences in chain length effect different mechanical responses as discussed below.

XRD and FTIR results revealed that these polypeptide chains contain ordered and amorphous domains. FIGS. 5c and 6 show the FTIR spectra for synthetic polypeptides. The amide I bands have been analyzed by using Fourier self-deconvolution and Gaussian fitting. FTIR peaks were assigned to secondary-structure elements. The relative areas of the single bands were used in the calculation of the fraction of the secondary structure features. A total of 11 bands were fitted to the deconvoluted spectra. The band centered at 1595 $cm^{-1}$ is assigned to the side chains of the protein (marked as sc). The absorption peak in this region is related to the aromatic ring in the side chains of tyrosine (Tyr) and histidine (His). Tyr and His are likely to contribute strongly to this band since their respective amino acid fractions are 15.3% and 4.9% for the synthetic polypeptides. A triplet of bands (marked as β) is fitted to the deconvoluted spectra between 1600 and 1637 $cm^{-1}$, which are assigned to β-sheets. Specifically, the band centered at 1613 $cm^{-1}$, 1626 $cm^{-1}$, and 1632 $cm^{-1}$ are assigned to intermolecular β-sheets formed by molecular aggregation, intermolecular β-sheets or stacking of antiparallel β-sheets in crystallized proteins, and the formation of intramolecular β-sheets respectively. A set of bands between the major β-sheet bands and the minor β-sheet band (1635-1700 $cm^{-1}$ range) are attributed to random coils, α-helices and turns secondary structures. The two bands centered at 1643 $cm^{-1}$ and 1650 $cm^{-1}$ are assigned to random coil conformations. The band centered at 1661 $cm^{-1}$ is assigned to α-helix secondary structures. These two secondary structural elements are attributed to the amorphous segments of the protein chains (Gly-rich) that connect the β-sheet crystals with each other. The three remaining bands centered at 1667, 1680 and 1693 $cm^{-1}$ are assigned to turn structures. The turn structure is attributed to the amorphous segments of the protein chains (Gly-rich) that allow the formation of intramolecular antiparallel β-sheets. Another small β-sheet band is observed at 1698 $cm^{-1}$, which is also observed in FTIR studies of silk fibroin. Although this band overlaps with the bands assigned to turn structures and is difficult to differentiate from them, it represents less than the 2% of the total amide I region. The fraction of secondary structure elements is determined by calculating the ratio of the fitted bands area to the total deconvoluted amide I band area. The secondary structure composition of synthetic polypeptides is summarized in Table 2.

Representative XRD spectra for three synthetic proteins are shown in FIG. 5d. The diffraction spectra for all three synthetic proteins are very similar. The crystallite size (i.e., ~3.9×2.2 nm) is estimated from XRD according to Scherrer equation. The Miller indices are assigned consistently with the native SRT from a related species (*Dosidicus gigas*). The major crystalline peaks can be observed at 2Θ=9.50°, 19.15° and 24.85° corresponding to lattice distances $d_{100}$=9.31 Å, $d_{200}$=4.63 Å and $d_{002}$=3.58 Å (FIG. 3e). Additionally, a weak diffraction peak is observed at 2Θ=36.73° with lattice distance $d_{240}$=2.44 Å accompanied with a broad peak. The intense peak at 2Θ=19.15° is attributed to the combination of (120) and (200) reflections and the peak at 2Θ=36.73° to the combination of (240) and (023) reflections. These lattice distances are 9.1 Å, 4.72 Å and 2×3.5 Å corresponding to the hydrogen-bond distance between two β-sheet chains, the distance between alternating β-sheet chains (i.e., unit cell dimension in the hydrogen-bond direction fitting two β-sheet chains) and the chain length of a single amino acid in an antiparallel β-sheet structure (with a two-residue repeat distance of 7.0 Å), respectively. According to the XRD results, β-sheet crystals can accommodate 11±2 amino acid residues along the backbone direction and 4.6±0.6 strands along the hydrogen bonding direction, which agrees well with the initial sequence design (i.e., 10 amino acid length between proline residues in crystalline segments). The β-sheet crystal structure is fitted into an orthorhombic unit cell referencing to other known β-sheet crystals such as silk. Although (0k0) diffraction peaks cannot be resolved in the current diffraction pattern, the unit cell dimension b (amino acid side chain direction) is calculated from the $d_{120}$, $d_{240}$ and $d_{023}$ spacing values. The unit cell parameters obtained by the diffraction data are a=9.31 Å (H-bond direction), b=11.06 Å (amino acid side chain direction) and c=7.16 Å (chain backbone direction). The crystalline segments of synthetic polypeptides are rich in Ala, Thr, Val, Ser and His amino acids, which increase the complexity in the inter-sheet stacking (especially when incorporating large side groups such as His). We calculated the crystallinity percentage of the synthetic polypeptides by fitting the crystalline and amorphous peaks in the Lorentz-corrected WAXS intensity data. The crystallinity index is calculated as the ratio of the deconvoluted crystalline area to the total area. The crystallinity index of these proteins is in between 43-45% as listed in Table 3. This is slightly higher than the FTIR results due to increased noise inherent to WAXS analysis.

We analyzed the mechanical response of all three synthetic polypeptide using DMA. Syn-n4 is brittle, and shows linear elastic behavior at low strains and then fracture. In contrast both syn-n7 and syn-n11 can be deformed to larger strains compared to syn-n4, and they exhibit irreversible plastic deformation. The drawability of the syn-n11 was significantly larger than other two samples. Quantitative stress-strain analysis was carried out where the DMA analysis was repeated at least three times for each sample. Young modulus (~0.7-0.8 GPa) for the synthetic polypeptides was estimated from the linear region of the stress-strain curve. Compared to elastic modulus of recombinant 18 kDa SRT protein from *Loligo vulgaris* (~1-2 GPa) this value is slightly lower. The lower modulus could be due to ambient water in the sample (~5%) or trace amounts of HFIP retained from casting (<%1). Although the elastic modulus and the yield strength for three samples are similar (i.e., ~14 MPa for syn-n4 and syn-n7 and slightly higher value of 18 MPa for syn-n11), their toughness (i.e., 0.14, 0.46, and 2.37 MJ/m³ respectively) and extensibility (i.e., 2, 4.5, and 15% respectively) increases as a function of polypeptide molecular weight.

Following the structure-property relationship for the yield stress of thermoplastics ($\sigma_y$=0.025.E), we estimate the yield strength of the synthetic proteins as 17.5 MPa, which agrees well with the experimental data of 14-18 MPa. The amorphous region of the synthetic protein has a loose network of chains that are tied together through secondary interactions (e.g., hydrogen bonds and van der Waals interactions). Therefore, we propose that the amorphous chains and reordering of β-sheets should dominate the fracture mechanism and the secondary bonds are broken upon tensile deformation. Deconvoluted FTIR spectrum shows that the crystallinity content of deformed syn-n11 samples doesn't change (Table 4), whereas individual β-sheet peaks vary (i.e., reorganization of crystalline domains), the turn content increases and α-helix content decreases. This agrees well with the observed macroscopic tensile behavior of an initial linear elastic regime followed by a large plateau regime at which the secondary bonds break.

We designed and characterized a new polypeptide sequence based on the native amino-acid content of semi-crystalline SRT proteins, and then generated tandem repeats of this sequence with a range of chain lengths using our PD-RCA approach. We demonstrate that toughness and extensibility of the synthetic polypeptides increase as a function of their molecular weights whereas the elastic modulus and yield strength remain unchanged.

From the description and data provided herein, polypeptides of varying size and composition of crystalline repeats can be produced. Such proteins can have considerable diversity (variable AVSTH-rich) in their crystal-forming sequences. Designing novel synthetic polypeptides with diverse semi-crystalline structure will help to elucidate repetition and composition rules for structural proteins. Similar to their natural and recombinant counterparts, synthetic SRT-mimics such as those described here can be processed to form any of a variety of three-dimensional shapes, including but not necessarily limited to ribbons, lithographic patterns, and nano-scale objects such as nanotube arrays. The ability to easily manufacture protein-based materials with tunable self-healing properties will find applications in a broad array of useful applications including textiles, cosmetics, and medicine.

An exemplary peptide sequence below is given to illustrate variations that can be made, for example, in crystalline domains. In particular, the following polypeptide (SynE3) was used as a basis for introducing variations in the crystalline region shown in italics:

MTYGYGGLYGGLYG-GLGYPAAASVSTVHHPYGYGGLYGGLYGGLGYPA AASVSTVHHPYGYGGLYGGLYG-GLGYPAAASVSTVHHPYGYGGLYGGLYG-GLGYPAAAS VSTVHHPYGYGGLYGGLYG-GLGYPAAASVSTVHHPYGYGGLYGGLYGGLGYP-AAASVST VHHPYGYGGLYGGLYG-GLGYPAAASVSTVHHPS (SEQ ID NO:299). We determined variations can be introduced in at least positions S23, V24, S25, T26 (where the numbering begins counting the first N-terminal Gas amino acid number 1). Combinations of these variations were identified such that over 150 distinct polypeptide sequences were generated. The variations changed the SynE3 amino acid to a Pro, Leu or Ala. We also produced sequences containing insertions and deletions.

Sequences of an additional three exemplary polypeptides are provided below. Underlined amino acids denote amorphous region; Italicized amino acids denote crystalline region and lower case amino acids denote cloning region. The polypeptides are labeled as syn-n4 containing 4 repeats, syn-n7 containing 7 repeats and syn-n11 containing 11 repeats.

Syn-n4 (15 kDa)
(SEQ ID NO: 300)
Mgtls<u>YGYGGLYGGLYGGLGYGP</u>AAA*SVSTVHH*Pstgtls<u>YGYGGLYG</u>

<u>GLYGGLGYGP</u>AAA*SVSTVHH*Pstgtls<u>YGYGGLYGGLYGGLGYGP</u>AAA

*SVSTVHH*Pstgtls<u>YGYGGLYGGLYGGLGYGP</u>AAA*SVSTVHH*Pstgtl s<u>YGYGGLYGGLYGGLGYGP</u>

Syn-n7 (25 kDa)
(SEQ ID NO: 301)
Mgtls<u>YGYGGLYGGLYGGLGYGP</u>AAA*SVSTVHH*Pstgtls<u>YGYGGLYG</u>

<u>GLYGGLGYGP</u>AAA*SVSTVHH*Pstgtls<u>YGYGGLYGGLYGGLGYGP</u>AAA

*SVSTVHH*Pstgtls<u>YGYGGLYGGLYGGLGYGP</u>AAA*SVSTVHH*Pstgtl s<u>YGYGGLYGGLYGGLGYGP</u>AAA*SVSTVHH*Pstgtls<u>YGYGGLYGGLYG</u>

<u>GLGYGP</u>AAA*SVSTVHH*Pstgtls<u>YGYGGLYGGLYGGLGYGP</u>AAA*SVST*

*VHH*Pstgtls<u>YGYGGLYGGLYGGLGYGP</u>

Syn-n11 (42 kDa)
(SEQ ID NO: 302)
Mgtls<u>YGYGGLYGGLYGGLGYGP</u>AAA*SVSTVHH*Pstgtls<u>YGYGGLYG</u>

<u>GLYGGLGYGP</u>AAA*SVSTVHH*Pstgtls<u>YGYGGLYGGLYGGLGYGP</u>AAA

*SVSTVHH*Pstgtls<u>YGYGGLYGGLYGGLGYGP</u>AAA*SVSTVHH*Pstgtl s<u>YGYGGLYGGLYGGLGYGP</u>AAA*SVSTVHH*Pstgtls<u>YGYGGLYGGLYG</u>

<u>GLGYGP</u>AAA*SVSTVHH*Pstgtls<u>YGYGGLYGGLYGGLGYGP</u>AAA*SVST*

*VHH*Pstgtls<u>YGYGGLYGGLYGGLGYGP</u>AAA*SVSTVHH*Pstgtls<u>YGY</u>

<u>GGLYGGLYGGLGYGP</u>AAA*SVSTVHH*Pstgtls<u>YGYGGLYGGLYGGLGY</u>

<u>GP</u>AAA*SVSTVHH*Pstgtls<u>YGYGGLYGGLYGGLGYGP</u>AAA*SVSTVHH*P stgtls<u>YGYGGLYGGLYGGLGYGP</u>AAA*SVSTVHH*Pstgtls<u>YGYGGLY</u>

<u>GGLYGGLGYGP</u>

Materials and Methods for the Foregoing Examples.

Construction of a Tandem-Repeat Template:

A 111-bp gene fragment (FIG. 2A) encoding an 18-amino-acid amorphous region and an 11-amino-acid crystalline region was synthesized by Genewiz, cloned into plasmid pCR-Blunt by standard methods, and verified by Sanger sequencing. The insert contains five restriction sites to enable the PD-RCA process described below: two ScaI sites, to allow the insert to be removed from its vector by digestion; a BbvCI site, to allow a phi29-polymerase priming site to be generated by the nicking enzyme nt.BbvCI; and, an Acc65I and an ApaI site, which can each be blocked through the incorporation of 5-methylcytosine in place of cytosine. A circular, nicked version of the insert sequence was prepared as a template for rolling circle amplification (RCA), as follows. The plasmid was digested with ScaI-HF and the resulting 105-bp fragment was isolated on a 1% agarose-TAE gel and purified with an Omega Bio-Tek E.Z.N.A gel extraction kit. The purified 105-bp fragment was then circularized with T4 ligase at room temperature, followed by 10 minutes at 65° C. to inactivate the ligase. 1 µL of the heat-inactivated ligation reaction was then nicked using nt.BbvCI to create a priming site for RCA. The nicking enzyme reaction was heat-inactivated for 20 minutes at 80° C.

Rolling-Circle Amplification:

1.5 µL of the heat-inactivated nicking reaction was used as the template in a 10-µL rolling-circle amplification reaction with 1×NEB phi29 polymerase buffer, 1 µg BSA, 1 mM dATP, 1 mM dGTP, 1 mM dTTP, 0.5 mM dCTP, 0.5 mM 5-methyl-dCTP, and 2.5 units NEB phi29 polymerase. The reaction was incubated at 30° C. for 24 hours, and then heat-inactivated for 10 minutes at 65° C.

Sizing and Cloning of Tandem-Repeat Products:

The heat-inactivated RCA reaction was sequentially digested with ApaI and Acc65I, yielding tandem repeats of various sizes due to the random protection of their recognition sites by 5-methylcytosine (FIG. 2B). Tandem-repeat fragments between 500 bp and 1500 bp were isolated from a 1% agarose-TAE gel and purified with an Omega Bio-Tek E.Z.N.A gel extraction kit. The purified fragments were cloned via the Acc65I and ApaI sites into the open-reading frame of an expression vector prepared by site-directed mutagenesis of pET14b. Colony PCR was used to screen for clones with inserts of the desired sizes; diagnostic digestion and Sanger sequencing confirmed the lengths and compositions of the clones after plasmid isolation.

Protein Expression of TR-Syn:

A single colony was inoculated and grown overnight in 5 mL of LB with ampicillin (100 µg/mL). The overnight culture were scaled up to 2 L (i.e., four 500 mL LB media) and was grown on a shaker at 210 rpm and 37° C. for 5 hours. When the cultures reached OD600 of 0.7-0.9, IPTG was added to the final concentration of 1 mM and shaking was continued at 37° C. for 4 hours. Then, the cells were pelleted at 12,000 rpm for 15 minutes and stored at −80° C. After thawing, cell pellets were resuspended in 300 mL of lysis buffer (50 mM Tris pH 7.4, 200 mM NaCl, 1 mM PMSF, and 2 mM EDTA), and lysed using a high-pressure homogenizer. The lysate was pelleted at 14,000 rpm for 1 hour at 4° C. The lysed pellet was washed twice with 100 mL of urea extraction buffer (100 mM Tris pH 7.4, 5 mM EDTA, 2 M Urea, 2% (v/v) Triton X-100), and then washed with 100 mL of washing buffer (100 mM Tris pH 7.4, 5 mM EDTA). Protein collection in washing step (urea extraction and final wash) was performed by centrifugation at 5000 rpm for 15 minutes. The resulting recombinant-protein pellet was dried with a lyophilizer (Labconco, FreeZone 6 plus) for 12 hours. The final yield of expressed protein was approximately 15 mg per liter of bacterial culture.

Protein Gel Preparation:

0.2 mg of SRT is dissolved in 1 mL of 5% acetic acid/2 M urea solution, and subjected to sodium dodecyl sulfate polyacrylamide gel electrophoresis (SDS-PAGE) for protein separation. In each lane 10-30 µg of synthetic proteins were used together with SDS gel loading buffer that have either 6.7 M urea without acetic acid or 3.4 M urea with 2% acetic acid final concentration. The protein gels were stained with Coomassie blue dye.

Sample Preparation:

Syn-n4, Syn-n7, or Syn-n11 protein was dissolved in 1,1,1,3,3,3-Hexafluoro-2-propanol (HFIP) to a concentration of 50 mg/mL in a sonication bath for 1 hour. The solution was then cast into polydimethylsiloxane (PDMS) dog-bone shaped molds to produce the desired geometry for mechanical testing and solvent was evaporated at room temperature under a fume hood overnight. Resulting films were 50 µm in thickness, 2 mm in width and approximately 15 mm in length.

XRD:

X-Ray Diffraction (Wide Angle X-ray Scattering, WAXS) data was collected in a Rigaku DMAX-Rapid II Microdiffractometer (wavelength λ=0.154 nm) using a Cu Kα source and a 30 µm collimator with 10 minute exposure at 50 kV and 40 mA. The scattering angle 2Θ was collected from 3° to 75°. 2D WAXS diffraction patterns were converted to a one-dimensional pattern by integration across all azimuthal angles (avoiding the beam stop). The crystallinity index is calculated as the ratio of the area of crystal peaks to the total area by fitting the Lorentz-corrected WAXS intensity data using Gaussian functions. The data is analyzed with MDI Jade X-ray diffraction software and peak fitting was performed in OriginPro 8.5 software.

ATR-FTIR (attenuated total reflectance Fourier transform infrared spectroscopy): Spectral data were collected (Thermo Scientific Nicolet 6700 FT-IR) under attenuated total reflection (diamond crystal) mode using Happ-Genzel apodization with 4 $cm^{-1}$ resolution from 400 to 4000 $cm^{-1}$. For each spectrum, 256 scans were co-added. Fourier self-deconvolution (FSD) and second derivative evaluation of the amide I band (1580-1706 $cm^{-1}$) were performed using the OMNIC software (Thermo Scientific, v7.3). Second derivatives were obtained from the original amide I spectra and a nine-point Savitsky-Golay smoothing filer of polynomial degree 5 was applied. FSD was performed with Lorentzian line shape with 25 $cm^{-1}$ bandwidth and an enhancement factor of 2. Curve fitting was performed. Individual bands were fitted to the deconvoluted spectra and were assigned to secondary structural components. The number and position of the fitted bands were obtained from the second derivative spectra, where the minima in the second derivative spectra corresponded to the fitted band maxima in the deconvoluted spectra. Gaussian curve fitting was performed in OriginPro 8.5 software by using a nonlinear least-squares method. First, the initial band positions (taken from the second derivatives) were fixed and the width and height were left as free parameters. Then, the band positions were allowed to change within a $\pm 1$ $cm^{-1}$ range using the built-in Levenberg-Marquardt algorithm. The relative areas of the single bands were used in the secondary-structure composition calculations.

Mechanical Testing:

Mechanical analysis was performed with a TA 800Q DMA instrument with film-tension clamps. Stress-strain curves were obtained at a constant strain rate of 1% per minute and a preload of 0.01 N.

RNA Isolation Protocol:

Suction cups were defrosted and RNALater solution was decanted. Any remaining SRT in the suction cups was removed to reduce protein contamination. The tissues samples were homogenized by slicing them into smaller pieces with a clean razor inside a biological hood and resuspended in RNAlater solution. The homogenized tissue was disrupted by adding 600 µL of RLT Plus lysis buffer (Qiagen), and kept in room temperature for 2 min (or until the solution color turned yellow) in eppendorf tubes. The solution was centrifuged for 3 min at high speed. For the DNA elimination, the lysate supernatant from last step was transferred to a DNA Eliminator spin column (Qiagen, RNAeasy Mini Kit), and centrifuged for 30 s at 10 000 rpm. 600 µL of 70% ethanol solution was added to the flow through and mixed well by pipetting without centrifugation. For RNA filtering, the solution was transferred to a RNAeasy spin column (Qiagen, RNAeasy Mini Kit) and centrifuged for 15 s at 1000 rpm. Three wash buffer steps were performed according to the Mini Kit user manual. Finally, RNA extraction was completed by adding 50 µL of RNase-free water directly to the spin column membrane, and by collecting the solution via centrifugation for 1 minute at 10 000 rpm. The solution was stored in the fridge for sequencing.

Dataset:

Details of the mRNA separation and conversion to cDNA can be found in our earlier publication (Pena-Francesch A, et al. (2014) Materials Fabrication from Native and Recombinant Thermoplastic Squid Proteins. *Advanced Functional Materials* 24(47):7401-7409) The isolated RNA was sequenced on an Illumina Hiseq instrument. European common squid (*Loligo vulgaris*) dataset contained 10,160,143 paired-end reads of 250 bp. *Loligo pealei*, *Todarodes pacificus*, and *Euprymna scolopes* datasets contained on average 12 million (i.e., 19207485, 10035062,7652668 respectively) paired-end reads of 150 bp.

Bioinformatics Analyses:

We used Trimmomatic (Bolger A M, Lohse M, & Usadel B (2014) Trimmomatic: a flexible trimmer for Illumina sequence data. *Bioinformatics:btu*170) for the quality control. Adaptor sequences and polyAs were removed from reads. Sliding-window trimming was performed, cutting once the average quality within a window size of 4 base pairs falls below 25. Very short reads of <36 base pairs were removed.

Transcript Assembly:

The quality controlled data sets were assembled using Trinity (Grabherr M G, et al. (2011) Full-length transcriptome assembly from RNA-Seq data without a reference genome. *Nature biotechnology* 29(7):644-652) with strand specific RNA sequencing library specification. Trinity assembly produced 33180, 42937, 48555, and 63562 transcripts from *Loligo vulgaris, Loligo pealei, Todarodes pacificus*, and *Euprymna scolopes* datasets respectively.

Blast Search and Short Read Mapping:

ORFs were extracted from trinity-assembled transcripts using transdecoder. Peptide sequences from the protein of interest were sequenced using mass-spectrometry (LC-MS/MS). From this, peptides with a confidence score of >50 were searched against transdecoder identified ORFs using tblastn. The blast hits that had alignments with >90% of the length of the peptide and with >=80% sequence identity were identified as the best hits. These best-hit transcripts were again searched for beta sheets (e.g, ASHVT-rich) using tblastn. The identified transcripts that had both peptide and beta-sheet sequence matches were extracted. From this set, we have chosen as candidate transcripts the sequences that have high glycine content and have polypeptide pattern P?*P (eg: PAAASVSTVHHP (SEQ ID NO:305) in the length range of 7 to 26. However, since most of the assembled transcripts were not long enough to contain the complete coding sequences, further steps were necessary to identify and refine these. Our iterative process consisted of aligning the reads to each of the candidate transcripts using bwa-mem algorithm then extending the transcript according to the consensus sequences of the nucleotides extending past the end of the alignment. The resulting extended alignment was then again used as candidate in an identical subsequent step. This process of alignment, consensus call and extension was repeated until a stop codon was encountered that indicated that coding sequence of the transcript has been terminated. The process can be thought of as a supervised assembly method were we relied on automated processes to produce candidate extensions but have had to resort to manually curating the results. The manual curation was necessary because the automated transcript assemblies were not sufficiently sensitive and required fine tuning the results. The resulting candidate transcripts were aligned using Clustalw.

TABLE 1

Synthetically produced polypeptides and corresponding sizes based on mass spectroscopy analysis

| Sample | Designed Tandem Repeat (n) | Mass Spec Protein Size (kDa) |
|---|---|---|
| Syn-n4 | 4 | 15.6 |
| Syn-n7 | 7 | 25.7 |
| Syn-n11 | 11 | 40.5 |

TABLE 2

FTIR analysis of synthetic polypeptides

| | Syn-n4 | Syn-n7 | Syn-n11 |
|---|---|---|---|
| β-sheet | 41.6 ± 0.1% | 40.7 ± 1.3% | 41.8 ± 1.2% |
| Random Coil | 31.5 ± 1.2% | 33.1 ± 3.1% | 32.1 ± 3.3% |
| α-helix | 11.8 ± 0.6% | 11.7 ± 1.7% | 11.5 ± 0.4% |
| turns | 15.1 ± 0.5% | 14.6 ± 0.1% | 14.5 ± 2.5% |

TABLE 3

Percent of crystallinity of synthetic polypeptides from XRD analysis and their comparison to FTIR.

| Sample | C.I. (XRD) | C.I. (FTIR) |
|---|---|---|
| Syn-n4 | 45% | 41.6 ± 0.1% |
| Syn-n7 | 43% | 40.7 ± 1.3% |
| Syn-n11 | 45% | 41.8 ± 1.2% |

TABLE 4

FTIR analysis of Amide-I band for pristine and stretched syn-n11 samples.

| Syn-n11 | Pristine | Stretched |
|---|---|---|
| β-sheet | 41.8 ± 1.2% | 43.0 ± 2.1% |
| random coil | 32.1 ± 3.3% | 30.6 ± 1.1% |
| α-helix | 11.5 ± 0.4% | 6.4 ± 0.5% |
| turns | 14.5 ± 2.5% | 19.9 ± 0.7% |

TABLE 5

| Sequence | |
|---|---|
| YYRKSVSTVSHGAHY | (SEQ ID NO: 1) |
| VSSSVSHVSHGAHY | (SEQ ID NO: 2) |
| AATAVSHTTHGIHH | (SEQ ID NO: 3) |
| AATTAVTHH | (SEQ ID NO: 4) |
| HVGTSVHSVSHGA | (SEQ ID NO: 5) |
| HVGTSVHSVSHGV | (SEQ ID NO: 6) |
| VTSAVHTVS | (SEQ ID NO: 7) |
| AATTAVTQTHH | (SEQ ID NO: 8) |
| AATTAVTHH | (SEQ ID NO: 9) |
| AATAVSHTTHHA | (SEQ ID NO: 10) |
| AVSTVSHGLGYGLHH | (SEQ ID NO: 11) |
| RSVSHTTHSA | (SEQ ID NO: 12) |
| YYRRSFSTVSHGAHY | (SEQ ID NO: 13) |
| VSSVRTVSHGLHH | (SEQ ID NO: 14) |
| AATAVSHTTHH | (SEQ ID NO: 15) |
| VGAAVSTVHH | (SEQ ID NO: 16) |
| AATAVSHNSS | (SEQ ID NO: 17) |
| YIGRSVSTVSHGSHY | (SEQ ID NO: 18) |
| MSSSVSHVSHTAHS | (SEQ ID NO: 19) |
| VVSHVTHTI | (SEQ ID NO: 20) |
| VGASVSTVSHGIGH | (SEQ ID NO: 21) |
| VGQSVSTVSHGVHA | (SEQ ID NO: 22) |
| TGSSISTVSHGV | (SEQ ID NO: 23) |
| VGAAVSTVHH | (SEQ ID NO: 24) |
| AATAVSHTTHH | (SEQ ID NO: 25) |
| GAAAYSHTVHH | (SEQ ID NO: 26) |
| AATTYRQTTHH | (SEQ ID NO: 27) |
| AATAVSHTTHHA | (SEQ ID NO: 28) |
| AAASVSTVHH | (SEQ ID NO: 29) |
| AATAVSHTTHHA | (SEQ ID NO: 30) |
| AVSTVSHGLGYGLHH | (SEQ ID NO: 31) |
| ATAVSHTTHHA | (SEQ ID NO: 32) |
| YIGRSVSTVSHGSHY | (SEQ ID NO: 33) |
| MSSSVSHVSHTAHS | (SEQ ID NO: 34) |

TABLE 5-continued

VVSHVTHTI (SEQ ID NO: 35)

TGASVNTVSHGISHA (SEQ ID NO: 36)

ASTSVSHTTHSV (SEQ ID NO: 37)

VGASVSTVSHGIGH (SEQ ID NO: 38)

HTVSHVSHG (SEQ ID NO: 39)

VAHHGTISRRYAI (SEQ ID NO: 40)

VTHYSHVSHDVHQ (SEQ ID NO: 41)

AVGHTTVTHAV (SEQ ID NO: 42)

AATSVKTVSHGFH (SEQ ID NO: 43)

VGSTISHTTHGVHH (SEQ ID NO: 44)

AATSVSHTTHGVHH (SEQ ID NO: 45)

AASSVTHTTHGVAH (SEQ ID NO: 46)

GLLGAAATTYKHTTHHA (SEQ ID NO: 47)

AATTYSHTAHHA (SEQ ID NO: 48)

AAASTVSTVHH (SEQ ID NO: 49)

AATYSHTTHHA (SEQ ID NO: 50)

AAASVSTAHH (SEQ ID NO: 51)

AATSYSHALHH (SEQ ID NO: 52)

GLLGAAATTYKHTTHHA (SEQ ID NO: 53)

AATTYSHTAHHA (SEQ ID NO: 54)

AAASTVSTVHH (SEQ ID NO: 55)

AATYSHTTHHA (SEQ ID NO: 56)

AAAASVSTVHH (SEQ ID NO: 57)

AATSFSHTAHHA (SEQ ID NO: 58)

AAASTVSTVHH (SEQ ID NO: 59)

AATYSHTTHHA (SEQ ID NO: 60)

SVATRRVVY (SEQ ID NO: 61)

AVSHVTHTI (SEQ ID NO: 62)

AATSVSHTTHSV (SEQ ID NO: 63)

VGASVSTVSHGVHA (SEQ ID NO: 64)

VIHGGATLSTVSHGV (SEQ ID NO: 65)

TGTSVSTVSHGV (SEQ ID NO: 66)

HSVSTVSHGA (SEQ ID NO: 67)

AGSSISTVSHGVHA (SEQ ID NO: 68)

TGSSISTVSHGVHS (SEQ ID NO: 69)

HIGTSVSSVSHGA (SEQ ID NO: 70)

HVGTSVHSVSHGV (SEQ ID NO: 71)

HASTTTHSIGL (SEQ ID NO: 72)

HSVSHVSHG (SEQ ID NO: 73)

VAHHGTISRRYAI (SEQ ID NO: 74)

HSVSHVSHG (SEQ ID NO: 75)

VAHHGTISRRYAI (SEQ ID NO: 76)

SHGVSHTAGYSSHY (SEQ ID NO: 77)

GHAVTHTVHH (SEQ ID NO: 78)

SAGGTTVSHSTHGV (SEQ ID NO: 79)

AVSHVTHTIHA (SEQ ID NO: 80)

HAVSTVAHGIH (SEQ ID NO: 81)

AATSVSHTTHSV (SEQ ID NO: 82)

AVRHTTVTHAV (SEQ ID NO: 83)

AATSVKTVSHGYH (SEQ ID NO: 84)

VGSTSVSHTTHGVHH (SEQ ID NO: 85)

AATTVSHTTHGAHH (SEQ ID NO: 86)

AASSVTHTTHGVAH (SEQ ID NO: 87)

TABLE 5-continued

SSYYGRSASTVSHGTHY (SEQ ID NO: 88)

TSVSQVSHTAHS (SEQ ID NO: 89)

VRYHGYSIGH (SEQ ID NO: 90)

AVSHVTHTIHA (SEQ ID NO: 91)

AATSVSHTTHSV (SEQ ID NO: 92)

VGASVSTVSHGVHA (SEQ ID NO: 93)

TGTSVSTVSHGV (SEQ ID NO: 94)

TGASVSTVSHGL (SEQ ID NO: 95)

AGSSISTVSHGVHA (SEQ ID NO: 96)

ATASVSHTTHGVHH (SEQ ID NO: 97)

AATTVSHSTHAV (SEQ ID NO: 98)

AATTVSHSTHAV (SEQ ID NO: 99)

GATTYSHTTHAV (SEQ ID NO: 100)

AVSHVTHTI (SEQ ID NO: 101)

AATSVSHTTHSV (SEQ ID NO: 102)

VIHGGATLSTVSHGV (SEQ ID NO: 103)

AGSSISTVSHGVHA (SEQ ID NO: 104)

GHAVTHTVHH (SEQ ID NO: 105)

SAGGTTVSHSTHGV (SEQ ID NO: 106)

AVRHTTVTHAV (SEQ ID NO: 107)

AATSVKTVSHGYH (SEQ ID NO: 108)

VGSTSVSHTTHGVHH (SEQ ID NO: 109)

GAAFHY (SEQ ID NO: 110)

AATTVSHTTHGAHH (SEQ ID NO: 111)

AASSVTHTTHGVAH (SEQ ID NO: 112)

AAVSHTTHHA (SEQ ID NO: 113)

AATAVSHTTHH (SEQ ID NO: 114)

TABLE 5-continued

VGAAVSTVHH (SEQ ID NO: 115)

VGGAVSTVHH (SEQ ID NO: 116)

GVAAYSHSVHH (SEQ ID NO: 117)

VSSVSTVSHGLHH (SEQ ID NO: 118)

VGAAVSTVHH (SEQ ID NO: 119)

VGGAVSTVHH (SEQ ID NO: 120)

GVAAYSHSVHH (SEQ ID NO: 121)

VASSVSHTTHGVHH (SEQ ID NO: 122)

AATTVSRTTHHA (SEQ ID NO: 123)

AATAVSHVTHHA (SEQ ID NO: 124)

AATSVSRTTHHA (SEQ ID NO: 125)

ATAAVSHTTHHA (SEQ ID NO: 126)

AATAVSHTTHHA (SEQ ID NO: 127)

AATAVSHTTHHA (SEQ ID NO: 128)

AATTVSRTTHHA (SEQ ID NO: 129)

AAAVSHVTHHA (SEQ ID NO: 130)

AATSVSHTTHHA (SEQ ID NO: 131)

AATAVSHTTHHA (SEQ ID NO: 132)

AATAVSHTTHHA (SEQ ID NO: 133)

AATSVSRTTHHA (SEQ ID NO: 134)

ATAAVSHTTHHA (SEQ ID NO: 135)

AATAVSHTTHHA (SEQ ID NO: 136)

AATAVSHVTHHA (SEQ ID NO: 137)

HTVSHVSHG (SEQ ID NO: 138)

VAHHSVVSRRYAI (SEQ ID NO: 139)

AATSVSHTTHHA (SEQ ID NO: 140)

TABLE 5-continued

AATAVSHTTHHA (SEQ ID NO: 141)

AATAVSHTTHHA (SEQ ID NO: 142)

AATAVSHTTHHA (SEQ ID NO: 143)

AAAVSHVTHHA (SEQ ID NO: 144)

AATAVHTTHHA (SEQ ID NO: 145)

VGAAVSHVTHHA (SEQ ID NO: 146)

VATSVSRTTHHA (SEQ ID NO: 147)

AATAVSHTTHHA (SEQ ID NO: 148)

SATAVSHTSH (SEQ ID NO: 149)

ASSAVSHTSHH (SEQ ID NO: 150)

VATVTSQTSHHV (SEQ ID NO: 151)

AASAVSTSTH (SEQ ID NO: 152)

VATSVSRTTHHA (SEQ ID NO: 153)

AATAVSHVTHHA (SEQ ID NO: 154)

VAHHSVVSRRYAI (SEQ ID NO: 155)

HAVGAVSTLHH (SEQ ID NO: 156)

HSVAVGVHH (SEQ ID NO: 157)

AATAVSHTTHHA (SEQ ID NO: 158)

AATAVSHVTHHA (SEQ ID NO: 159)

VAHHSVVSRRYAI (SEQ ID NO: 160)

TABLE 6

GYGLGGLYGGYLGGLHYGGYLGGLHYGGYLHY (SEQ ID NO: 161)

GVGGLYGGYLGGLHGGYGLGGIYGGYGAHY (SEQ ID NO: 162)

GVGGYGMGGLYGGYGLGGVYGGYGLGG (SEQ ID NO: 163)

GYGLGVGL (SEQ ID NO: 164)

LGLGYGGYGLGLGYGLGHGYGLGLGAGI (SEQ ID NO: 165)

TABLE 6-continued

GLGLGYGYGLGHGLG (SEQ ID NO: 166)

GLGLGYGLGLGL (SEQ ID NO: 167)

MGGLYGGYGLGGVYGGYGLGGIYGGYGAHY (SEQ ID NO: 168)

GVGGLYGGYGLGGLYGGYGLGGLHGGYSLGGLYGGYGAHY (SEQ ID NO: 169)

GVGGLYGGYGLGGLHYGGYGLGGLHYGGYGLHY (SEQ ID NO: 170)

YGYGGLYGGLYGGLG (SEQ ID NO: 171)

YGYGGLYGGLYGGLG (SEQ ID NO: 172)

VAYGGWGYGLGGLHGGWGYGLGGLHGGWGYALGGLYGGLHY (SEQ ID NO: 173)

VGLGYGGLYGGLHY (SEQ ID NO: 174)

VGYGGFGLGFGGLYGGLHY (SEQ ID NO: 175)

SLGAYGGYGLGGLIGGHSVYH (SEQ ID NO: 176)

SLGAYGGYGLGGIVGGYGAYN (SEQ ID NO: 177)

VGYGGFGLGFGGLYGGLHY (SEQ ID NO: 178)

VGLGYGGFGLGYGGLYGGFGY (SEQ ID NO: 179)

VAYGGLGYGFGF (SEQ ID NO: 180)

GYGGLYGGLGYHY (SEQ ID NO: 181)

YGYGGLYGGLYGGLGY (SEQ ID NO: 182)

VGYGGYGLGAYGAYGLGYGLHY (SEQ ID NO: 183)

YGYGGLYGGLYGGLG (SEQ ID NO: 184)

VGYAGYGLG (SEQ ID NO: 185)

YGGFGYGLY (SEQ ID NO: 186)

GYGGLYGHYGGYGLGGAYGH (SEQ ID NO: 187)

GIGGVYGHGIGGLGGVYGHGIGGVYGHGIGGLYGHGFGGAYGGYGGYGIGG (SEQ ID NO: 188)

VTYGGLGLGGLYGGLGYGGLGYGGLGYGGLGYGGLGYGGLGYGGLGAGGLYG (SEQ ID NO: 189)

GAVGLGYGLGGGYGGLYGLHL (SEQ ID NO: 190)

ALGLGLYGGAHL (SEQ ID NO: 191)

TABLE 6-continued

GLGLNYGVYGLH (SEQ ID NO: 192)

GYGGWGYGLGGWGHGLGGLG (SEQ ID NO: 193)

YGGIGLGGLYGGYGAHF (SEQ ID NO: 194)

HSVGWGLGGWGGYGLGYGVHA (SEQ ID NO: 195)

ALGAYGGYGFGGIVGGHSVYH (SEQ ID NO: 196)

ALGGYGGYGLGGIVGG (SEQ ID NO: 197)

ALGAYGGYGLGGLVGGFGAYH (SEQ ID NO: 198)

VGFGGYGLGGYGLGGYGLGGYGLGGYGLGGLVGGYGSYH (SEQ ID NO: 199)

VGYGGYGLGGYGGYGLGGLTGGYGV (SEQ ID NO: 200)

GYGLGLGYGLGLGAG (SEQ ID NO: 201)

LGLGYGYGLGLGYGLGLGAGI (SEQ ID NO: 202)

HLGLGLGYGYGLGHGLG (SEQ ID NO: 203)

GLGLGYGLGLGYGYGV (SEQ ID NO: 204)

GYGLGLGLGGAGYGY (SEQ ID NO: 205)

VGGYGGFGLGGYGGYGLGG (SEQ ID NO: 206)

VGYGGLYGHYGGYGLGGVYHGVGLGGVYHGIGGAYGGYGLGVGGLYGGYGGYGIGG (SEQ ID NO: 207)

VGGYGGFGLGGYGGYGLGG (SEQ ID NO: 208)

VGYGGLYGHYGGYGLGGVYHGVGLGGVYHGVGLGGVYSH (SEQ ID NO: 209)

GIGGAYGGYGLGVGGLYGGYGGYGIGG (SEQ ID NO: 210)

VLSGGLGLSGLSGGYGTYR (SEQ ID NO: 211)

GYGGVGYGGLGYGGLGYGVGGLYGLQY (SEQ ID NO: 212)

GYGGWGYGLGGWGHGLGGLGSYGLHY (SEQ ID NO: 213)

HSVGWGLGGWGGYGLGYGVRS (SEQ ID NO: 214)

YGDVYGGLYGGLYGGLLGA (SEQ ID NO: 215)

VAYGGLGLGALGYGGLGYGGLGYGGLGAGGLYGLHY (SEQ ID NO: 216)

GYGLGLGLYGAHL (SEQ ID NO: 217)

AYGGWGYSLGRWGQGLGGLGTYGLHY (SEQ ID NO: 218)

HSVGWGLGGWGGYGLGYGVHA (SEQ ID NO: 219)

ALGGYGGYGLGGIVGGHSVYH (SEQ ID NO: 220)

ALGEYGGYGLGGIVGGH (SEQ ID NO: 221)

GFGGYGLGGYGLGGYGLGGYG (SEQ ID NO: 222)

IGFGGWGHGYGYSGLGFGGWGHGLGGWGHGYGY (SEQ ID NO: 223)

HAVGFGGWGHGIGLGHGFGY (SEQ ID NO: 224)

HAVGFGGWGHGFGY (SEQ ID NO: 225)

HSVSYGGWGFGHGGLYGLH (SEQ ID NO: 226)

HADYGVSGLGGYVSSY (SEQ ID NO: 227)

HSVGWGLGGWGGYGLGYGVHA (SEQ ID NO: 228)

ALGAYGGYGFGGIVGGHSVYH (SEQ ID NO: 229)

VGFGGYGLGGYGLGGYGLGGYGLGGYGLGGVVGGFGGYH (SEQ ID NO: 230)

FGYGGVGYGGLGYGGLGYGVGGLYGLQY (SEQ ID NO: 231)

VAYGGLGLGALGYGGLGYGGLGAGGLYGLHY (SEQ ID NO: 232)

AGLGYGLGGVYGGYGLHA (SEQ ID NO: 233)

YGYGGLYGGLGYHAGYGLGGYGLGYGLHY (SEQ ID NO: 234)

VGWGLGGLYGGLHH (SEQ ID NO: 235)

GYGGYGLGLGGLYGGLHY (SEQ ID NO: 236)

GYGGYGLGFGGLYGGFGY (SEQ ID NO: 237)

AYGYGYGLGGYGGYGLYGGYGLHH (SEQ ID NO: 238)

VAYGGWGYGLGGLHGGWGYGLGGLYGGLH (SEQ ID NO: 239)

GYGGYGLGLGGLYGGLHY (SEQ ID NO: 240)

VGYAGYGYGLGSYGGYAGLGLGLYGAGYHY (SEQ ID NO: 242)

YAYGGLYGGYGLGAYGY (SEQ ID NO: 243)

TABLE 6-continued

```
                                      (SEQ ID NO: 244)
VGYAGYGYGLGAYGGYAGLGLGLYGAGYHY (SEQ ID NO: 245)
YAYGGLYGGYGLGAYGY (SEQ ID NO: 246)
VGYGGFGLAGYGYGY (SEQ ID NO: 247)
YGYGGLYGGYAGLGLGLYGAGYHY (SEQ ID NO: 248)
YAYGGLYGGYGLGAYGY (SEQ ID NO: 249)
VGYAGYGYGLGAYGGYAGLGLGLYGAGYHY (SEQ ID NO: 250)
YAYGGLYGGYGLGAYGY (SEQ ID NO: 251)
VGYAGYGLGLYGAGYHY (SEQ ID NO: 252)
YAYGGLYGGYGLGAYGY (SEQ ID NO: 253)
VGYAGYGLGAYGGYAGYGLGAFGGYAGYGLGAFGGYAGLGLGLYGAGYH
Y (SEQ ID NO: 254)
LGFGGLLGGYGGLHHGVYGLGGYGGLYGGYGLGGYGLHGLHY (SEQ ID NO: 255)
LGFGGVLGYGGLHHGVYGLGGYGGLHGAYGLGGYGGLHGAYGLGGYGGL
YGGYGLGGH (SEQ ID NO: 256)
VGYGGYGYGGLGAYGHYGGYGLGGLYGGYGLGGAYGGYGLGGGYGGYGV
GVHSRYGVG (SEQ ID NO: 257)
GYGYGGLLGGYGLHY (SEQ ID NO: 258)
YGYGLAGYGGLYGGLHGAAYGLGGYGLHY (SEQ ID NO: 259)
LGYGLAGYGGLYGGLYGGHGLGGYGGVYGGYGLHGLHY (SEQ ID NO: 260)
LGFGGVLGYGGLHH (SEQ ID NO: 261)
GVYGLGHGAYGLGGYGGLHGAYGLGGYGGLYGGYGLGGYGALHGGLYGG
YGLGGGLL (SEQ ID NO: 262)
YSYGGLVGGYGGLYHHA (SEQ ID NO: 263)
LFGGILGGYGGVLAGYGGLHHGAYGLGGYGGLYGGYGLGGYGLHGLHY (SEQ ID NO: 264)
LGFGGVLGYGGLHHGVYGLGGYGGLHGAYGLGGYGGLHGAYGLGGYGGL
YGGTLSTL (SEQ ID NO: 265)
GYGYGGLLGGLGHAVG (SEQ ID NO: 266)
VGYGYGGLLGGYGGLYGGWGGVYGGLG (SEQ ID NO: 267)
VGYGYGGFLGGYGLGVYGHGY (SEQ ID NO: 268)
LGYGLAGYGGLYGGLYGGHGLGGYGGVYGGYGLHGLHY
```

TABLE 6-continued

```
                                      (SEQ ID NO: 269)
LGFGGVLGYGGLHHGVYGLGGYGGLHGAYGLGGYGGLHGAYGLGGYGGL
YGGYGLGGYGALHGGLYGGYGLGGGL (SEQ ID NO: 270)
GYGYGGLLGGYGLHY (SEQ ID NO: 271)
YGYGLAGYGGLYGGYGLGGYGLGY (SEQ ID NO: 272)
LGYGLAGYGGLYGGLYGGHGLGGYGGVYGGYGLHGLHY (SEQ ID NO: 273)
LGFGGVLGYGGLHHGVYGLGGYGGLHGAYGLGGYGLGGFHGGYGLGG (SEQ ID NO: 274)
VGLGLGGFHGGYGFGGYGLGGFHGGYG (SEQ ID NO: 275)
VGFGGYGYGGIGGLYGGHYGGYGLGGAYGHYGGYGLGG (SEQ ID NO: 276)
GYGYGGLLGGLGHAVG (SEQ ID NO: 277)
GYGYGGLLGGYGGLYGGWGGVYGGLG (SEQ ID NO: 278)
VGYGYGGFLGGYGLGVYGHGY (SEQ ID NO: 279)
LGYGGLLGGYGGLYGGYGLGGYGLGY (SEQ ID NO: 280)
YGYGLAGYGGLYGGLLH (SEQ ID NO: 281)
LGYGLAGYGGLYGGLYGGHGLGGYGGVYGGYGLHGLHY (SEQ ID NO: 282)
LGFGGVLGYGGLHHGAYGLGGYGGLYGGYGLGGYGGLYGGYGALHGGYG
LGY (SEQ ID NO: 283)
YGLAGYGGLYGGLLH (SEQ ID NO: 284)
TALGYGGLYGGYGLGAYGLGY (SEQ ID NO: 285)
LGYGGLLGGYGGLYGRYGVGGYGLGY (SEQ ID NO: 286)
GGYGSLLGGHGGLYGGLGL (SEQ ID NO: 287)
YGYGGVLGGYGQGL (SEQ ID NO: 288)
LGYGGLLGGYGGLHHGVYG (SEQ ID NO: 289)
GGYGGLYGGYGLGGYGGLHGAYGLGGYGGVYGGYGLGGH (SEQ ID NO: 290)
VGYGGYGYGGLGAYGHYGGYGLGGLYGGYG (SEQ ID NO: 291)
VGYGYGGLLGGYGGLYGGWGGVYGGLG (SEQ ID NO: 292)
VGYGYGGFLGGYGLGVYGHGY (SEQ ID NO: 293)
LGYGLAGYGGLYGGLYGGHGLGGYGGVYGGYGLHGLHY (SEQ ID NO: 294)
LGFGGVLGYGGLHHGVYGLGGYGGLHGAYGLGGYGGLYGGYGLGGH
```

TABLE 6-continued

VYGGYGLGGH (SEQ ID NO: 295)

VGYGGYGYGGGLYGGHYGGYGHFGGVHSHYGVG (SEQ ID NO: 296)

YGDVYGGLYGGLYGGLLGA (SEQ ID NO: 297)

LGYGGLLGGYGALHGGLYGGYGLGGLHY (SEQ ID NO: 298)

Example 4

It will be recognized from the foregoing that SRT proteins are h-bonded thermoplastic elastomers extracted from the tentacles of the squid suction cups (FIG. 2A) that exhibit an unusual and reversible transition (i.e., thermoplastic) from a solid to a melt and, therefore, can be thermally shaped into any 3D geometry (e.g. fibers, colloids, and thin films). These proteins have been shown to have excellent mechanical properties in both wet and dry conditions, exceeding most natural and synthetic polymers while having the unique capability of self-healing and self-assembly. As described above, SRT proteins have a segmented copolymer sequence containing amorphous and crystalline domains, and may be alternatives to synthetic polymers. This unique example of structural proteins has demonstrated extraordinary physical properties, due to their unique semi-crystalline structure. It has been demonstrated as described herein that it is possible to control and improve the physical properties (i.e., mechanical and thermal) of SRT based biopolymers using a specific polypeptide sequence for both crystalline and amorphous regions. High yield (0.5 g/L) heterologous expression of these tandem repeat proteins in bacteria is demonstrated herein. These repetitive block copolymers are organized in a repetitive fashion, facilitating better alignment for anti-parallel beta (13) sheet formation, using molecular tandem repeat method, which requires amorphous, and crystalline repeat units to be separated by a small cloning sequence. Without intending to be bound by any particular theory, it is considered that the number of tandem repeat (TR) units defines the ultimate material properties, as they determine the molecular weight and interconnectivity of the crystals in these synthetic proteins (FIG. 2B). The synthetic proteins with 4, 7, and 11 repeat units were prepared, which resulted in synthetic proteins with molecular weights of 15 (Tr15), 25 (Tr25), and 42 kDa (Tr42), respectively as shown in the protein gel of FIG. 2C. The crystal dimensions of these repetitive synthetic proteins are relatively independent of the number of repeat units. The crystal domains of these synthetic proteins contain anti-parallel β sheets formed by 4 strands of the crystalline polypeptide sequence. This β sheet orientation results in a crystal with 3 nm long in the backbone direction and 2 nm wide in the hydrogen bonding direction. The amorphous sequence separates these crystals with tie chains corresponding to separation of 3 nm. The interconnectivity of these tie chains is related to the number of repeat units. In addition, in certain implementations, the crystals of these synthetic proteins do not demonstrate stacking of multiple β sheets, which makes them suitable for generating intercalated composites with 2D materials.

In order to demonstrate non-limiting embodiments of this disclosure, we combined synthetic proteins with graphene oxide and other compositions, such as MXene, to generate molecular composites that assemble into specific structures. The interlayer distance of these structures can be controlled using a single parameter (i.e., the number of repetitions in the sequence of the tandem proteins). This provides nanoscale control on the structure of the composite, and consequently on the material properties.

The fabrication of free-standing molecular composite films of synthetic proteins and two-dimensional (2D) materials were performed using vacuum assisted self-assembly (VASA) methods [K. W. Putz, et al., Advanced Functional Materials 20(19) (2010) 3322-3329] and ink jet printing, as further described below. VASA and printing enables assembly of highly ordered composites of 2D materials in bulk form.

For the VASA approach, Tr-proteins and GO first were dissolved in a common organic solvent (dimethyl sulfoxide (DMSO)), although it will be recognized that many other organic solvents may be substituted for DMSO in the VASA-based and printing methods described herein.

For VASA, these solutions were mixed and homogenized using ultrasonication. The resulting homogeneous solution was filtered directionally through anodized aluminum oxide membranes using a vacuum assisted solvent filtration apparatus (FIG. 7A). The rate of the assembly process was controlled by the vacuum, which led to highly ordered composites with alternating layers of protein and 2D materials. After complete removal of the solvent, the resulting free-standing molecular composite films were peeled from the inorganic membrane (FIG. 7B).

Prior to experimental characterization, composite films were dried in a vacuum to remove excessive solvent molecules. The initial characterization of the resulting composites was performed using electron microscopy, which demonstrated a compact stacking of alternating GO and protein layers (FIG. 7C, FIG. 10). The scanning electron microscopy (SEM) image shows several surface defects, yet the cross-section of the free-standing composite film looks void-free (FIG. 7C). The proper alternating stacking of the GO and synthetic protein layers can also be observed in the high-resolution transmission microscopy (HRTEM) image provided in the inset of FIG. 7C. In complementary to structural analysis using electron microscopy, we performed chemical analysis of the composite films using energy-dispersive X-ray spectroscopy (EDS). The EDS analysis has demonstrated a clear outline of the material distribution for GO and synthetic protein. The images correspond to carbon and oxygen signal shows patterns covering the entire cross-section of composite film homogeneously, as these elements are common for both GO and synthetic protein (FIG. 7D (ii, iii)). On the other hand, the image corresponding to nitrogen signal demonstrates a discontinuous pattern, consisting of stacked lines, since nitrogen only exists in synthetic protein layers (FIG. 7D(iv)).

To analyze the microstructure of the molecular composites further X-ray diffraction (XRD) analysis were performed on composites prepared with synthetic proteins molecular weights of 15 kDa, 25 kDa, and 42 kDa, which are named as TR15, TR25, TR42, respectively (FIG. 8A). The XRD characterization demonstrates that diffraction peaks corresponding to the (001) plane of GO shifts toward higher angles for composites consisting of proteins with higher molecular weight. This indicates the interlayer distance between GO layers increases with increasing molecular weight of the synthetic proteins. The synthetic protein TR15 kDa increase the interlayer distance of 2D materials by 4.8 Å. On the other hand, synthetic protein TR42 increase the interlayer distance of 2D materials by 9.6 Å. In order to identify the origin of the increase in interlayer distance for GO, we performed thermogravimetric analysis coupled with mass spectrometry (TGA-MS) for each molecular composite. This characterization is essential to identify the composition of these materials, as the increase in interlayer distance could be originating from higher protein concentrations. TGA-MS studies show that molecular composites prepared with different molecular weights has quite similar trends for mass loss with increasing temperature (FIG. 8B). The composition analysis performed on the TGA-MS data reveals that these composites have very similar protein concentration (55 wt %±10 wt %). This is a clear indication of the change in interlayer distance is originating from the molecular interactions between GO and synthetic proteins, and also the structure of the synthetic protein, which act as a programmable molecular spacer between GO layers. To support the chemical composition studies (TGA, EDS), we performed mass spectroscopy analysis on these composites, which confirmed the existence and the amount of the protein in these molecular composite films (FIG. 11).

Following the structural and compositional characterization of molecular composites, we developed a thermal actuator by combining excellent thermal conductivity of GO (SRT:0.3 W/mK, GO:300 W/mK) and superior thermal expansion coefficient of synthetic proteins (SRT: $-95 \times 10^{-6} K^{-1}$, GO: $-50 \times 10^{-6} K^{-1}$). This actuator consists of two films: a molecular composite film composed of GO and TR42 and a separate synthetic protein film of TR42 (FIG. 9A). The composite film is responsible for homogeneous and rapid heat dissipation and uniform actuation. The GO layers in the composite dissipates heat properly and protein layers initiate thermal expansion triggering actuation, due to intrinsically superior thermal expansion coefficient. The second film of TR42 protein is implemented to improve the ultimate curvature of the actuator. The thermal actuation is initiated using joule heating.

The heater electrodes are patterned on the films using gold sputtering and shadow masking, but those skilled in the art will recognize that other techniques can be used. The thickness of the gold electrodes is 60 nm, which are significantly thinner than composite (40 μm) and synthetic protein films (20 μm). This is important for minimizing the influence of gold electrodes on thermal actuation. The fabricated actuators are tested under fixed voltage values to test the corresponding curvature occurring due to thermal actuation (FIG. 9B, C). These actuators have demonstrated drastic curvature values reaching 1.2 $cm^{-1}$ with relatively small length (1.6 cm). The high-power values (1.2 $W/cm^2$) required to achieve this actuation is rather deceiving and potentially originating from the low heating efficiency of the electrodes. Because, the change in temperature needed to establish a curvature of 1.2 $cm^{-1}$ is only 47° C. for this actuator, which is comparable to the state of the art thermal actuators (FIG. 9C). A unique advantage of this actuator is the high-strength yet flexible nature of protein interlayers, which improve the force generation of actuators. In addition, these actuators can be relaxed to their initial state at a fast rate by immersing them in water, as the water act as a plasticizer and make these synthetic biopolymers rubbery. The flexibility of the molecular composite can be tuned by controlling the molecular weight of the protein, which increases as a function of the interlayer distances (e.g., GO is more brittle compared to GO-SRT composite). In contrary, the curvature of the actuation scales inversely with the relative thickness of the layered materials. Therefore, novel thermal actuators for applications in IR-imaging, soft robotics, and thermal sensing could be built by tuning the interlayer distance of GO layers using structural proteins, given the benefit of the present dislcosure. Also, the low temperature actuation (curvature: 1.2 $cm^{-1}$, T: 67° C.) and biocompatible nature of the materials makes this actuation approach quite feasible for prosthetic applications.

In summary, the Examples above demonstrate layered 2D systems, where interlayer distances can be precisely and finely tuned by the molecular weight of the protein-based polymer form a mechanism for thermal actuation that can be controlled in a molecular composite. The disclosure demonstrates the ability to use the tandem proteins in contact with layered GO sheets to control fast (<10 ms) actuation mechanism of biomorph structure at low voltages (~1V), which are nanoscale characteristics that are important to the operation of the flexible 2D devices made from these materials. Thus, this disclosure provides a basis for creating functional devices with user defined thermal expansion and transport properties from composites of two-dimensional (2D) materials and repetitive proteins. The variability of the amino-acid sequences in the proteins, which dictates the degree of crystallinity and alignment of the protein layers, can be used to control the interactions at the 2D material/protein interface, ultimately dictating the functional physical properties (e.g., electrical resistivity and thermal conductivity) of the devices. Successful development of programmable 2D composites will have a significant impact on multiple applications in various fields (e.g., synthetic biology, autonomy, nanotechnology, and energy) and open new avenues of 2D layered materials research.

Example 5

This example provides description of MXenes and uses thereof, and generation of compositions of this disclosure using ink jet printing. The Examples use MXenes as a representative composition that can be combined with proteins as described herein, but it will be recognized by those skilled in the art that other materials, some of which are described above, can be substituted for the MXenes.

In more details, MXenes are conductive 2D-layered materials, which have potential applications in next-generation, programmable, flexible, and optically superior, energy efficient and mechanical strong materials and devices. This disclosure illustrates fabrication of 2D nanocomposites that comprise layers of MXenes and layers of semi-crystalline self-assembling proteins. As described above, the disclosure provides examples of 2D protein composites of metallic MXene made using inkjet printing. As an alternative to chemical vapor deposition (CVD), protein-based 2D assembly provides unique advantages of precisely tuning interlayer distances (nanometer level precision) for application in electronic and optical applications, as well as processibility in inkjet printing as well as membrane production. Conducting nanocomposites described herein and in this and the Examples that follow are expected to have a significant impact on antenna design, wearable electronics in textiles as well as biochemical sensing that could be integrated into a wide array of electronic devices.

Two-dimensional titanium carbide sheets possess functional groups at their surface, which can facilitate several physical interactions including hydrogen bonding (FIG. 13a). Proteins can form connections with these 2D crystals via hydrogen bonding, however governing the ultimate structure of this assembly entails use of polypeptides that comprise amino acid sequence that can be modulated using synthetic biology, as described further above. In particular, in the Examples above, we demonstrated that it is possible to control the assembly and interconnectivity of hydrogen bonding 2D crystals (Graphene oxide) using proteins consisting of tandem repeats of block copolymer-like amino acid sequence derived from squid ring teeth (FIG. 13b). In this and the following Examples, we modulated ink formulations to initiate formation of this assembly during solvent evaporation of printed patterns (FIG. 13c). The initial pristine MXene solutions containing exfoliated sheets of MXene in DMSO (2.25 mg/m) remains stable for an extended period of time (~6 months). As the concentration of synthetic proteins is increased, the rate of sheet aggregation/assembly increases (FIG. 13d). To establish more rapid assembly kinetics in MXene inks, we utilized synthetic proteins with highest number of repeats (n=11, tandem repeat 42 kDa (TR42)), and consequently with highest number of available sites for hydrogen bonding (FIG. 13b). We observed that instant aggregation (~10 s) occurs at a critical protein concentration corresponding to 1 mg/ml. For inks with protein concentrations slightly lower than 1 mg/ml the assembly process takes 12 hours at room temperature without agitation, stirring, and sonication. In light of this assessment, we prepared ink solutions with protein concentrations 0.5 mg/ml (P7), and 0.95 mg/ml (P5) from initial MXene/DMSO solutions (2.25 mg/ml) (FIG. 13d).

The initial printing performance of pristine and protein based (P5 and P7) MXene inks are evaluated by printing circles with 1 cm diameter on to paper (FIG. 14a). Each printed sample goes darker with increasing number of passes, which is indicative of uniform printing. The higher magnification images of printed samples at the edges of circles indicates a better stability for patterns printed using protein based MXene inks. Circles printed with pristine MXene inks exhibit splattered droplets at the edge of circles (FIG. 14a(ii)), which is potentially originating from satellite droplets observed during printing process (FIG. 13e). On the other hand, there is no indication of droplet splatter for circles printed using protein based MXene inks (P5, P7) (FIG. 14a(iii)). Further assessment of surface characteristics by scanning electron microscopy (SEM) imaging of circles printed from protein based MXene ink P5 revealed relatively uniform deposition of MXene flakes across printed areas (FIG. 14a(iv)). SEM images with higher magnification presents the planar structural organization of MXene sheets and protein assemblies (bright spots) located on MXene sheets (FIG. 14a(v)). The planar organization of MXene sheets are also confirmed by the cross-sectional SEM image acquired from printed samples of ink P5 (FIG. 14a(vi)). Microstructure characterization by X-ray diffraction from printed samples on paper indicates MXene inks form an intercalated sheet structure in which MXene layers are either stacked on top of each other, separated by interfacial DMSO and protein molecules (FIG. 14b). Samples printed from pristine MXene inks demonstrate presence of stacked MXene layers represented by (002) planes in XRD pattern ($2\theta=7\pm0.15$), and intercalated DMSO molecules in between layers, which leads to formation of secondary periodicity for (002) planes ($2\theta=5.75\pm0.1$) (FIG. 14c). The influence of protein mediated assembly of MXene sheets begin to show in samples printed from P7 inks, as the intercalation of protein molecules adds a tertiary periodicity for (002) planes of MXene (FIG. 14c). In addition, diffraction peaks originating from crystalline (100) plane of synthetic proteins ($2\theta=9.15$) also become apparent (FIG. 14c). These vague diffraction signals become more dominant for samples printed from ink P5, potentially due to increased protein concentration (FIG. 14c). The changes in spacing between MXene sheets are quantified using X-ray diffraction data (FIG. 14d). This analysis reveals that protein mediated assembly helps keep sheets interconnected in exchange of increased separation between sheets, which has an influence on electrical properties of printed MXene patternss (FIG. 14d). The characterization of sheet resistance of inks printed on paper substrates shows resistance values higher than patterns processed using water-based MXene solutions, possibly due to elevated intersheet separation originating from intercalating DMSO and protein molecules (FIG. 14e). Even though, the sheet resistance values achieved from these printed patterns on paper are comparable to state of the art graphene based ink-jet printed electrodes without any need for further treatment (FIG. 14e).

Besides paper substrates, the printing performance of pristine and protein based MXene inks were evaluated for other substrates relevant for inkjet-printing including glass, PET, polymethylmethacrylate (PMMA), and polydimethylsiloxane (PDMS). The printing performance assessment of PMMA provided inclusive results, as DMSO effectively dissolves PMMA. In addition, contact angle measurements performed for PDMS substrates showed insufficient wetting of MXene inks of PDMS surface. Consequently, and without intending to be constrained by any particular theory, the printing performance analysis was extended to focus on other, more potent substrates, including fused silica glass, and particularly PET, due to potential applications in flexible electronics (FIG. 15).

To analyze printing capabilities of pristine and protein based MXene inks on glass and PET substrates, large circles (d=2 cm) are printed using pristine MXene ink, ink P5 formulation (FIG. 15a(i, ii, iii, iv, v, vi)). Pristine MXene inks demonstrated irregular material deposition for both glass and PET substrates (FIG. 15a(i, iii, v). In the case of porous paper substrates, pristine MXene inks are absorbed more homogeneously by the surface, because of rapid dissipation of DMSO solvent in paper (FIG. 14a). However, relatively flat and non-porous glass and PET substrates involve an additional mechanism of adhesion for MXene sheets to be deposited uniformly. The printed circles using ink P5 offered a much better coverage and shape confirmation in comparison to pristine MXene ink (FIG. 14a(ii, iv, vi)). To exploit protein mediated adhesive capabilities of these MXene inks, parallel electrodes with a width of 120 μm are printed with separation distances of 40 μm (30 μm is the resolution of the printer moving stage) and 150 μm (FIG. 14a(vii, viii)). The resulting electrodes were continuous for 2 cm and can conduct electricity (R~40 kΩ each), which highlights printing capabilities of protein based inks for devices patterned on flexible substrates for soft electronics. Device performance of printed patterns using protein based MXene inks is also characterized by assembling a light emitting diode (LED) circuit using printed electrodes on PET substrate, which sustained conductivity under excessive bending deformation (maximum radius of curvature=3.6 mm).

Beyond stabilizing printing process for MXene sheets, tandem repeat proteins induce an additional feature to printed nanoparticles, as humidity mediated swelling leads to reversible alteration of resistivity of printed patterns on PET substrates (FIG. 16a). The most drastic change in resistance occurs at thinner electrodes (10 pass), yet, deviation in sheet resistance is also far greater for thinner electrodes (FIG. 16a). To analytically estimate humidity sensing performance of electrodes printed from protein based MXene inks, a sensor response is defined from initial resistance ($R_0$), saturation resistance ($R_s$=resistance values at 100% relative humidity). The thicker electrodes reach saturation resistance at lower levels of humidity, on the other hand thinner electrodes demonstrate a gradual increase in resistance up to 90% humidity (FIG. 16b). As a consequence, thicker electrodes exhibit binary-like response (on/off) and thinner electrodes are more suitable for humidity sensing. The binary-like response of thicker electrodes is more visible for sheet resistance measurements performed during continuous humidity cycles for various humidity conditions (FIG. 16c, d, e). Thin electrodes (10 Pass) cannot reach saturation resistance or present inconsistent resistance cycles during changes of humidity. On the other hand, thick printed electrodes (20 and 30 pass) reaches saturation values at relatively low changes in humidity (10%), and exhibit more consistent changes in resistance during humidity changes.

The following materials and methods were used to obtain the results described in this Example.

Preparation of MXene inks: Solutions containing of MXene sheets exfoliated in water (4.5 mg/ml) are centrifuged (13200 rpm, 15 mins) and water is exchanged with either DMSO or TR42 protein/DMSO solutions (TR42 protein concentration of 0.5 mg/ml for ink P7, and 0.95 mg/ml for ink P5). For preparation of pristine MXene inks, centrifuged MXene sheets are redispersed in DMSO using bath sonication under controlled temperature (25° C.) for 2 hours. This centrifugation, solvent exchange, and redispersion cycle is performed 3 times to ensure complete solvent exchange to DMSO. The concentration of the resulting MXene/DMSO solution is diluted to 2.25 mg/ml for generating pristine MXene inks that can be printed without clogging printer tips. For preparation of ink P7 and P5, centrifuged MXene sheets are redispersed in respective TR42 protein/DMSO solutions using bath sonication under controlled temperature (25° C.) for 2 hours. This protocol consisting of centrifugation, solvent exchange, and redispersion is performed for 3 cycles, and MXene concentration of these inks are diluted to 2.25 mg/ml to ensure continuous printing.

Printing process and device and fabrication: Prepared inks were printed using a custom made multi-channel piezo inkjet printer. Due to large flake size of MXene sheets, a single nozzle with a diameter of 125-250 µm was used during printing processes. The resolution is defined as the smallest width of printed line is 120 µm on PET (FIG. 15a (vii, viii)). The minimum distance between two parallel lines for reliable printing is 40 µm, which can go up to 150 µm depending on the substrate (the resolution of moving stage is 30 µm) (FIG. 15a(vii)). The entire printing processes were carried out at operational frequency of 200 Hz. The droplet spacings for printed electrode patterns including lines, circles, rectangles, and circuits on different substrates using different inks can be found in Table 7.

Conductive inks printing setup: Piezoelectric drop-on-demand inkjet (PIJ) printing is used in this disclosure for forming droplets of the conductive ink solution comprising 2D materials and structural proteins. A representative experimental setup is shown in FIG. 13 and primarily consisted of an inkjet printer (Jetlab®, MicroFab Technologies Inc., Plano, Tex.). The printer was housed in a vertical laminar flow cabinet (Air Science Purair VLF 36, Fort Myers, Fla.) for ensuring clean printing conditions. The conductive ink droplets were formed by using a PIJ dispensing device with an orifice diameter of 120 µm (MJ-ABL-01-120-8MX, MicroFab Technologies). A unipolar voltage pulse was used for actuating the dispenser to expel the conductive ink droplets. The voltage pulse was characterized by a rise time of 3-5 µs duration, a dwell time of 20-25 µs duration, a fall time of 3-5 µs duration and an idle time of 3-5 µs duration. In addition, the amplitude of the voltage pulse was 25-30 V and the frequency of the pulse was 200 Hz. The back pressure was set at −10 to −12 mmHg (−1.333 to −1.599 kPa) such that the meniscus at the dispensing device nozzle orifice resulted in stable droplets formation. The droplets landed on a substrate and printed in various shapes, such as disc, square, ring, triangle, rectangle or any shape based on computer-aided design drawings or images, and multiple layers were printed on top of each other in order to build 3D composites. The layer thickness of printed composites was controlled by controlling the number of layers as well as the distance between adjacent droplets during printing.

Characterization: X-ray diffraction experiments were performed using reflection mode with PANalytical)(Pert Pro MPD (CuKα radiation, λ=1.5406 Å, operating at 40 keV, and cathode current of 20 mA) under standard laboratory conditions. Raman spectroscopy experiments were performed using LabRam system (Horiba Jobin-Yvon, France) using an excitation wavelength of 633.82 nm (He—Ne laser) and 3.5 mW power (10% of peak power). A 50× long working distance objective with numerical aperture of 0.50 was used and corresponding spot size was 30 µm×30 µm. The spectral resolution of the experiments was set to 2 cm$^{-1}$. Surface tension measurements of ink formulations were analyzed using a standard contact angle measurement system (First Ten Angstroms, FTA1000 B Class). Viscosity measurements of ink formulations were characterized by TA Instruments Discovery hybrid rheometer HR-2 at room temperature using a concentric cylinder geometry. Viscosity values were measured across a shear rate range of 5 to 200 s$^{-1}$. Optical images were acquired using benchtop optical imaging system (Thermofisher Scientific, EVO FL Auto Imaging System). Scanning electron microscopy (SEM) images were acquired using ZEISS 55 Ultra FESEM at 3 kV beam voltage. The thickness of printed patterns was measured using Veeco Dektak 6M profilometer. The sheet resistance values of the printed electrodes were measured using a custom built automated 4-point probe measurement system connected to a Keithey 2400 Sourcemeter (n=3, error bars represent standard deviation). Conductive thin lines printed using MXene inks were measured using a probe station connected to Keithley 2400 Sourcemeter. LED circuit bending experiments were performed in two-point probe configuration using a deformation stage custom built from optical mechanical stages. The LED circuit was powered by HP/Agilent Sourcemeter. The voltage readout on LED was acquired using HP/Agilent Sourcemeter. Sensor response measurements were also performed in two-point probe configuration using a digital multimeter. Samples were incubated in vacuum chamber for 10 mins prior to measurements.

Viscosity of ink formulations: The viscosity of the SRT/Mxene inks were measured in a rheometer as function of shear rate (FIG. 18). All inks exhibit a Newtonian fluid behavior (viscosity independent of shear rate), indicating that there is no aggregation in the measured range (5 to 200 s-1). Bare Mxene inks (without protein) have an average viscosity of 3.06±0.05 cP, while viscosity increases with protein concentration. P7 and P5 SRT/Mxene inks (with 0.5 and 1.0 mg/mL SRT concentration) have average viscosities of 3.33±0.05 cP and 3.39±0.04 cP respectively. The measurements were calibrated with bare DMSO solution, measuring a viscosity of 2.04±0.05 cP (1.99 cP reported in literature).

Printing process and droplet spacing: Optimal droplet spacing for continuous printing is calculated using maximum droplet spacing necessary for coalescence described by Stringer and Derby (Jonathan Stringer and Brian Derby, Formation and Stability of Lines Produced by Inkjet Printing, *Langmuir*, 2010, 26 (12), pp 10365-10372, the disclosure of which is incorporated herein by reference). The average droplet size for pristine MXene ink, ink P7, ink P5 are from 50 to 70 μm.

Contact angle values for each ink and substrate are presented at FIG. 18. Theoretical and experimental droplet spacing values are presented in Table 7.

TABLE 7

Theoretically calculated and experimentally employed droplet spacing values:

| | Inks | | | | | |
| --- | --- | --- | --- | --- | --- | --- |
| | Control | | Ink P7 | | Ink P5 | |
| Substrates | Theoretical | Experimental | Theoretical | Experimental | Theoretical | Experimental |
| Glass | 148 μm | 150 μm | 119 μm | 120 μm | 95 μm | 90 μm |
| PDMS | 40 μm | 60 μm | 36 μm | 60 μm | 37 μm | 60 μm |
| PET | 182 μm | 180 μm | 126 μm | 120 μm | 95 μm | 90 μm |
| PMMA | 137 μm | 120 μm | 100 μm | 90 μm | 81 μm | 90 μm |

Raman spectroscopy: Raman spectroscopy measurements were performed on patterns printed using ink P5. The Raman features originating from MXene sheets located in between 100 $cm^{-1}$ and 800 $cm^{-1}$ remains intact for printed patterns with various thicknesses (FIG. 21). It is also possible to observe a shoulder getting more prominent towards low wavenumbers becomes more visible with increasing thickness. This shoulder is originating from the fluorescence response of tandem repeat proteins. The MXene response matches exfoliated two-dimensional titanium carbide, which is indicative of 2D nature of MXene flakes are translated efficiently to printed MXene patterns.

While the invention has been described through specific embodiments, routine modifications will be apparent to those skilled in the art and such modifications are intended to be within the scope of the present invention.

What is claimed is:

1. A method of making a composite material comprising at least one two-dimensional (2D) inorganic layer comprising two-dimensional titanium carbide (MXene) and an at least one organic layer, the organic layer comprising one or more polypeptides which comprise alternating repeats of crystallite-forming subsequences and amorphous subsequences, wherein the crystallite-forming subsequences form crystallites comprising stacks of one or more β-sheets, and wherein the amorphous subsequences form a network of hydrogen bonds, the method comprising i) combining the one or more polypeptides with an inorganic material and an organic solvent, and ii) depositing the one or more polypeptides, the inorganic material and the organic solvent onto a substrate, thereby forming at least one composite layer comprising the one or more polypeptides and the inorganic material, and optionally repeating i) and ii) to form the composite material that is a multilayer composite material.

2. The method of claim 1, wherein the at least one organic layer has a thickness of from 0.5 nm-10.0 nm.

3. The method of claim 1, wherein the at least one inorganic layer has a thickness of from 0.5 nm-10.0 nm.

4. The method of claim 1, wherein the crystallite-forming subsequence is from about 2 nm to about 5 nm long.

5. The method of claim 1, wherein the one or more polypeptides comprises from 4 to 20 repeats of the crystallite-forming subsequences.

6. The method of claim 1, wherein the one or more polypeptide comprises from 4 to 20 repeats of the crystallite-forming subsequences.

7. The method of claim 1, wherein the one or more polypeptides comprises a sequence that exhibits crystallinity between 0% and 60%.

8. The method of claim 1, wherein the amorphous subsequence comprises from 10 to 60 amino acids.

9. The method of claim 1, comprising forming the multilayer composite material, wherein the multilayer composite material comprises between 2 and $10^9$ composite layers, each of which composite layers comprises an organic layer and an inorganic layer.

10. The method of claim 1, wherein the depositing the one or more polypeptides, the inorganic layer and the organic solvent onto the substrate comprises vacuum assisted self-assembly, or by passing the one or more polypeptides, the inorganic material and the organic solvent through a nozzle onto the substrate, wherein the composite material optionally comprises a heterostructure.

11. The method of claim 10, comprising the passing through the nozzle, wherein the one or more polypeptides, the inorganic material and the organic solvent are in a droplet having a diameter of from 50 to 70 µm.

12. The method of claim 10, wherein the one or more polypeptides, the inorganic material and the organic solvent are placed on the substrate to form lines having a minimum distance between one another of not less than 40 µm.

13. The method of claim 10, wherein the composite material consists essentially of the one or more polypeptides and the inorganic material.

14. The method of claim 10, comprising the passing through the nozzle.

15. The method of claim 14, wherein the passing through the nozzle comprises inkjet printing onto the substrate.

16. The method of claim 15, wherein the one or more polypeptides, the inorganic material and the organic solvent are in a droplet having a diameter of from 50 to 70 µm, and wherein the one or more polypeptides, the inorganic material and the organic solvent are placed on the substrate to form lines having a minimum distance between one another of not less than 40 µm.

17. A composite material made by a method of claim 10.

18. A composite material made by a method of claim 15.

19. A composite material made by a method of claim 16.

20. A method of making a composite material as in claim 10, comprising selecting a crystallite-forming subsequence and selecting an amorphous subsequence, the crystallite-forming subsequence comprising amino acid sequences that are capable of forming the crystallite-forming subsequences, wherein the crystallite-forming subsequences are from about 2 nm to about 5 nm long and comprise from 10 to 30 amino acids, and selecting an amino acid sequence that is capable of forming the amorphous subsequence, wherein the amorphous subsequence is about 3 nm long and comprise about 15 amino acids, and forming the composite material by incorporating an amino acid sequence that is capable of forming the crystallite-forming subsequences and an amino acid sequence that is capable of forming the an amorphous subsequence into a synthetic or recombinant polypeptide, and mixing the synthetic or recombinant polypeptide with an inorganic material that is two-dimensional titanium carbide (MXene) or a combination of the MXene and graphite oxide, and an organic solvent, and depositing the synthetic or recombinant polypeptide, the inorganic material and the organic solvent onto a substrate.

21. The method of claim 20, wherein the depositing onto the substrate comprises depositing the synthetic or recombinant polypeptide, the inorganic layer and the organic solvent onto the substrate comprises vacuum assisted self-assembly, or by passing the one or more polypeptides, the inorganic material and the organic solvent through a nozzle onto the substrate.

* * * * *

SEQUENCE LISTING

<160> NUMBER OF SEQ ID NOS: 312

<210> SEQ ID NO 1
<211> LENGTH: 15
<212> TYPE: PRT
<213> ORGANISM: Loligo vulgaris

<400> SEQUENCE: 1

Tyr Tyr Arg Lys Ser Val Ser Thr Val Ser His Gly Ala His Tyr
1               5                   10                  15

<210> SEQ ID NO 2
<211> LENGTH: 14
<212> TYPE: PRT
<213> ORGANISM: Loligo vulgaris

<400> SEQUENCE: 2

Val Ser Ser Ser Val Ser His Val Ser His Gly Ala His Tyr
1               5                   10

<210> SEQ ID NO 3
<211> LENGTH: 14
<212> TYPE: PRT
<213> ORGANISM: Loligo vulgaris

<400> SEQUENCE: 3

Ala Ala Thr Ala Val Ser His Thr Thr His Gly Ile His His

```
<210> SEQ ID NO 4
<211> LENGTH: 9
<212> TYPE: PRT
<213> ORGANISM: Loligo vulgaris

<400> SEQUENCE: 4

Ala Ala Thr Thr Ala Val Thr His His
1               5

<210> SEQ ID NO 5
<211> LENGTH: 12
<212> TYPE: PRT
<213> ORGANISM: Loligo vulgaris

<400> SEQUENCE: 5

His Val Gly Thr Ser Val His Ser Val Ser His Gly
1               5                   10

<210> SEQ ID NO 6
<211> LENGTH: 13
<212> TYPE: PRT
<213> ORGANISM: Loligo vulgaris

<400> SEQUENCE: 6

His Val Gly Thr Ser Val His Ser Val Ser His Gly Val
1               5                   10

<210> SEQ ID NO 7
<211> LENGTH: 9
<212> TYPE: PRT
<213> ORGANISM: Loligo vulgaris

<400> SEQUENCE: 7

Val Thr Ser Ala Val His Thr Val Ser
1               5

<210> SEQ ID NO 8
<211> LENGTH: 11
<212> TYPE: PRT
<213> ORGANISM: Loligo vulgaris

<400> SEQUENCE: 8

Ala Ala Thr Thr Ala Val Thr Gln Thr His His
1               5                   10

<210> SEQ ID NO 9
<211> LENGTH: 9
<212> TYPE: PRT
<213> ORGANISM: Loligo vulgaris

<400> SEQUENCE: 9

Ala Ala Thr Thr Ala Val Thr His His
1               5

<210> SEQ ID NO 10
<211> LENGTH: 12
<212> TYPE: PRT
<213> ORGANISM: Loligo vulgaris

<400> SEQUENCE: 10

Ala Ala Thr Ala Val Ser His Thr Thr His His Ala
1               5                   10
```

```
<210> SEQ ID NO 11
<211> LENGTH: 15
<212> TYPE: PRT
<213> ORGANISM: Loligo vulgaris

<400> SEQUENCE: 11

Ala Val Ser Thr Val Ser His Gly Leu Gly Tyr Gly Leu His His
1               5                   10                  15

<210> SEQ ID NO 12
<211> LENGTH: 10
<212> TYPE: PRT
<213> ORGANISM: Loligo vulgaris

<400> SEQUENCE: 12

Arg Ser Val Ser His Thr Thr His Ser Ala
1               5                   10

<210> SEQ ID NO 13
<211> LENGTH: 15
<212> TYPE: PRT
<213> ORGANISM: Loligo vulgaris

<400> SEQUENCE: 13

Tyr Tyr Arg Arg Ser Phe Ser Thr Val Ser His Gly Ala His Tyr
1               5                   10                  15

<210> SEQ ID NO 14
<211> LENGTH: 13
<212> TYPE: PRT
<213> ORGANISM: Loligo vulgaris

<400> SEQUENCE: 14

Val Ser Ser Val Arg Thr Val Ser His Gly Leu His His
1               5                   10

<210> SEQ ID NO 15
<211> LENGTH: 11
<212> TYPE: PRT
<213> ORGANISM: Loligo vulgaris

<400> SEQUENCE: 15

Ala Ala Thr Ala Val Ser His Thr Thr His His
1               5                   10

<210> SEQ ID NO 16
<211> LENGTH: 10
<212> TYPE: PRT
<213> ORGANISM: Loligo vulgaris

<400> SEQUENCE: 16

Val Gly Ala Ala Val Ser Thr Val His His
1               5                   10

<210> SEQ ID NO 17
<211> LENGTH: 10
<212> TYPE: PRT
<213> ORGANISM: Loligo vulgaris

<400> SEQUENCE: 17

Ala Ala Thr Ala Val Ser His Asn Ser Ser
1               5                   10

<210> SEQ ID NO 18
```

```
<210> SEQ ID NO 18
<211> LENGTH: 15
<212> TYPE: PRT
<213> ORGANISM: Loligo vulgaris

<400> SEQUENCE: 18

Tyr Ile Gly Arg Ser Val Ser Thr Val Ser His Gly Ser His Tyr
1               5                   10                  15

<210> SEQ ID NO 19
<211> LENGTH: 14
<212> TYPE: PRT
<213> ORGANISM: Loligo vulgaris

<400> SEQUENCE: 19

Met Ser Ser Ser Val Ser His Val Ser His Thr Ala His Ser
1               5                   10

<210> SEQ ID NO 20
<211> LENGTH: 9
<212> TYPE: PRT
<213> ORGANISM: Loligo vulgaris

<400> SEQUENCE: 20

Val Val Ser His Val Thr His Thr Ile
1               5

<210> SEQ ID NO 21
<211> LENGTH: 14
<212> TYPE: PRT
<213> ORGANISM: Loligo vulgaris

<400> SEQUENCE: 21

Val Gly Ala Ser Val Ser Thr Val Ser His Gly Ile Gly His
1               5                   10

<210> SEQ ID NO 22
<211> LENGTH: 14
<212> TYPE: PRT
<213> ORGANISM: Loligo vulgaris

<400> SEQUENCE: 22

Val Gly Gln Ser Val Ser Thr Val Ser His Gly Val His Ala
1               5                   10

<210> SEQ ID NO 23
<211> LENGTH: 12
<212> TYPE: PRT
<213> ORGANISM: Loligo vulgaris

<400> SEQUENCE: 23

Thr Gly Ser Ser Ile Ser Thr Val Ser His Gly Val
1               5                   10

<210> SEQ ID NO 24
<211> LENGTH: 10
<212> TYPE: PRT
<213> ORGANISM: Loligo vulgaris

<400> SEQUENCE: 24

Val Gly Ala Ala Val Ser Thr Val His His
1               5                   10

<210> SEQ ID NO 25
<211> LENGTH: 11
<212> TYPE: PRT
```

-continued

<213> ORGANISM: Loligo vulgaris

<400> SEQUENCE: 25

Ala Ala Thr Ala Val Ser His Thr Thr His His
1               5                   10

<210> SEQ ID NO 26
<211> LENGTH: 11
<212> TYPE: PRT
<213> ORGANISM: Loligo vulgaris

<400> SEQUENCE: 26

Gly Ala Ala Ala Tyr Ser His Thr Val His His
1               5                   10

<210> SEQ ID NO 27
<211> LENGTH: 11
<212> TYPE: PRT
<213> ORGANISM: Loligo vulgaris

<400> SEQUENCE: 27

Ala Ala Thr Thr Tyr Arg Gln Thr Thr His His
1               5                   10

<210> SEQ ID NO 28
<211> LENGTH: 12
<212> TYPE: PRT
<213> ORGANISM: Loligo vulgaris

<400> SEQUENCE: 28

Ala Ala Thr Ala Val Ser His Thr Thr His His Ala
1               5                   10

<210> SEQ ID NO 29
<211> LENGTH: 10
<212> TYPE: PRT
<213> ORGANISM: Loligo vulgaris

<400> SEQUENCE: 29

Ala Ala Ala Ser Val Ser Thr Val His His
1               5                   10

<210> SEQ ID NO 30
<211> LENGTH: 12
<212> TYPE: PRT
<213> ORGANISM: Loligo vulgaris

<400> SEQUENCE: 30

Ala Ala Thr Ala Val Ser His Thr Thr His His Ala
1               5                   10

<210> SEQ ID NO 31
<211> LENGTH: 15
<212> TYPE: PRT
<213> ORGANISM: Loligo vulgaris

<400> SEQUENCE: 31

Ala Val Ser Thr Val Ser His Gly Leu Gly Tyr Gly Leu His His
1               5                   10                  15

<210> SEQ ID NO 32
<211> LENGTH: 11
<212> TYPE: PRT
<213> ORGANISM: Loligo vulgaris

<400> SEQUENCE: 32

Ala Thr Ala Val Ser His Thr Thr His His Ala
1               5                   10

<210> SEQ ID NO 33
<211> LENGTH: 15
<212> TYPE: PRT
<213> ORGANISM: Loligo vulgaris

<400> SEQUENCE: 33

Tyr Ile Gly Arg Ser Val Ser Thr Val Ser His Gly Ser His Tyr
1               5                   10                  15

<210> SEQ ID NO 34
<211> LENGTH: 14
<212> TYPE: PRT
<213> ORGANISM: Loligo vulgaris

<400> SEQUENCE: 34

Met Ser Ser Ser Val Ser His Val Ser His Thr Ala His Ser
1               5                   10

<210> SEQ ID NO 35
<211> LENGTH: 9
<212> TYPE: PRT
<213> ORGANISM: Loligo vulgaris

<400> SEQUENCE: 35

Val Val Ser His Val Thr His Thr Ile
1               5

<210> SEQ ID NO 36
<211> LENGTH: 15
<212> TYPE: PRT
<213> ORGANISM: Loligo vulgaris

<400> SEQUENCE: 36

Thr Gly Ala Ser Val Asn Thr Val Ser His Gly Ile Ser His Ala
1               5                   10                  15

<210> SEQ ID NO 37
<211> LENGTH: 12
<212> TYPE: PRT
<213> ORGANISM: Loligo vulgaris

<400> SEQUENCE: 37

Ala Ser Thr Ser Val Ser His Thr Thr His Ser Val
1               5                   10

<210> SEQ ID NO 38
<211> LENGTH: 14
<212> TYPE: PRT
<213> ORGANISM: Loligo vulgaris

<400> SEQUENCE: 38

Val Gly Ala Ser Val Ser Thr Val Ser His Gly Ile Gly His
1               5                   10

<210> SEQ ID NO 39
<211> LENGTH: 9
<212> TYPE: PRT
<213> ORGANISM: Loligo vulgaris

<400> SEQUENCE: 39

-continued

His Thr Val Ser His Val Ser His Gly
1               5

<210> SEQ ID NO 40
<211> LENGTH: 13
<212> TYPE: PRT
<213> ORGANISM: Loligo vulgaris

<400> SEQUENCE: 40

Val Ala His His Gly Thr Ile Ser Arg Arg Tyr Ala Ile
1               5                   10

<210> SEQ ID NO 41
<211> LENGTH: 13
<212> TYPE: PRT
<213> ORGANISM: Loligo vulgaris

<400> SEQUENCE: 41

Val Thr His Tyr Ser His Val Ser His Asp Val His Gln
1               5                   10

<210> SEQ ID NO 42
<211> LENGTH: 11
<212> TYPE: PRT
<213> ORGANISM: Loligo vulgaris

<400> SEQUENCE: 42

Ala Val Gly His Thr Thr Val Thr His Ala Val
1               5                   10

<210> SEQ ID NO 43
<211> LENGTH: 13
<212> TYPE: PRT
<213> ORGANISM: Loligo vulgaris

<400> SEQUENCE: 43

Ala Ala Thr Ser Val Lys Thr Val Ser His Gly Phe His
1               5                   10

<210> SEQ ID NO 44
<211> LENGTH: 14
<212> TYPE: PRT
<213> ORGANISM: Loligo vulgaris

<400> SEQUENCE: 44

Val Gly Ser Thr Ile Ser His Thr Thr His Gly Val His His
1               5                   10

<210> SEQ ID NO 45
<211> LENGTH: 14
<212> TYPE: PRT
<213> ORGANISM: Loligo vulgaris

<400> SEQUENCE: 45

Ala Ala Thr Ser Val Ser His Thr Thr His Gly Val His His
1               5                   10

<210> SEQ ID NO 46
<211> LENGTH: 14
<212> TYPE: PRT
<213> ORGANISM: Loligo vulgaris

<400> SEQUENCE: 46

Ala Ala Ser Ser Val Thr His Thr Thr His Gly Val Ala His
1               5                   10

<210> SEQ ID NO 47
<211> LENGTH: 17
<212> TYPE: PRT
<213> ORGANISM: Loligo vulgaris

<400> SEQUENCE: 47

Gly Leu Leu Gly Ala Ala Ala Thr Thr Tyr Lys His Thr Thr His His
1               5                   10                  15

Ala

<210> SEQ ID NO 48
<211> LENGTH: 12
<212> TYPE: PRT
<213> ORGANISM: Loligo vulgaris

<400> SEQUENCE: 48

Ala Ala Thr Thr Tyr Ser His Thr Ala His His Ala
1               5                   10

<210> SEQ ID NO 49
<211> LENGTH: 11
<212> TYPE: PRT
<213> ORGANISM: Loligo vulgaris

<400> SEQUENCE: 49

Ala Ala Ala Ser Thr Val Ser Thr Val His His
1               5                   10

<210> SEQ ID NO 50
<211> LENGTH: 11
<212> TYPE: PRT
<213> ORGANISM: Loligo vulgaris

<400> SEQUENCE: 50

Ala Ala Thr Tyr Ser His Thr Thr His His Ala
1               5                   10

<210> SEQ ID NO 51
<211> LENGTH: 10
<212> TYPE: PRT
<213> ORGANISM: Loligo vulgaris

<400> SEQUENCE: 51

Ala Ala Ala Ser Val Ser Thr Ala His His
1               5                   10

<210> SEQ ID NO 52
<211> LENGTH: 11
<212> TYPE: PRT
<213> ORGANISM: Loligo vulgaris

<400> SEQUENCE: 52

Ala Ala Thr Ser Tyr Ser His Ala Leu His His
1               5                   10

<210> SEQ ID NO 53
<211> LENGTH: 17
<212> TYPE: PRT
<213> ORGANISM: Loligo vulgaris

<400> SEQUENCE: 53

Gly Leu Leu Gly Ala Ala Ala Thr Thr Tyr Lys His Thr Thr His His
1               5                   10                  15

Ala

```
<210> SEQ ID NO 54
<211> LENGTH: 12
<212> TYPE: PRT
<213> ORGANISM: Loligo vulgaris

<400> SEQUENCE: 54

Ala Ala Thr Thr Tyr Ser His Thr Ala His His Ala
1               5                   10

<210> SEQ ID NO 55
<211> LENGTH: 11
<212> TYPE: PRT
<213> ORGANISM: Loligo vulgaris

<400> SEQUENCE: 55

Ala Ala Ala Ser Thr Val Ser Thr Val His His
1               5                   10

<210> SEQ ID NO 56
<211> LENGTH: 11
<212> TYPE: PRT
<213> ORGANISM: Loligo vulgaris

<400> SEQUENCE: 56

Ala Ala Thr Tyr Ser His Thr Thr His His Ala
1               5                   10

<210> SEQ ID NO 57
<211> LENGTH: 11
<212> TYPE: PRT
<213> ORGANISM: Loligo vulgaris

<400> SEQUENCE: 57

Ala Ala Ala Ala Ser Val Ser Thr Val His His
1               5                   10

<210> SEQ ID NO 58
<211> LENGTH: 12
<212> TYPE: PRT
<213> ORGANISM: Loligo vulgaris

<400> SEQUENCE: 58

Ala Ala Thr Ser Phe Ser His Thr Ala His His Ala
1               5                   10

<210> SEQ ID NO 59
<211> LENGTH: 11
<212> TYPE: PRT
<213> ORGANISM: Loligo vulgaris

<400> SEQUENCE: 59

Ala Ala Ala Ser Thr Val Ser Thr Val His His
1               5                   10

<210> SEQ ID NO 60
<211> LENGTH: 11
<212> TYPE: PRT
<213> ORGANISM: Loligo vulgaris

<400> SEQUENCE: 60

Ala Ala Thr Tyr Ser His Thr Thr His His Ala
1               5                   10
```

```
<210> SEQ ID NO 61
<211> LENGTH: 9
<212> TYPE: PRT
<213> ORGANISM: Loligo vulgaris

<400> SEQUENCE: 61

Ser Val Ala Thr Arg Arg Val Val Tyr
1               5

<210> SEQ ID NO 62
<211> LENGTH: 9
<212> TYPE: PRT
<213> ORGANISM: Loligo vulgaris

<400> SEQUENCE: 62

Ala Val Ser His Val Thr His Thr Ile
1               5

<210> SEQ ID NO 63
<211> LENGTH: 12
<212> TYPE: PRT
<213> ORGANISM: Loligo vulgaris

<400> SEQUENCE: 63

Ala Ala Thr Ser Val Ser His Thr Thr His Ser Val
1               5                   10

<210> SEQ ID NO 64
<211> LENGTH: 14
<212> TYPE: PRT
<213> ORGANISM: Loligo vulgaris

<400> SEQUENCE: 64

Val Gly Ala Ser Val Ser Thr Val Ser His Gly Val His Ala
1               5                   10

<210> SEQ ID NO 65
<211> LENGTH: 15
<212> TYPE: PRT
<213> ORGANISM: Loligo vulgaris

<400> SEQUENCE: 65

Val Ile His Gly Gly Ala Thr Leu Ser Thr Val Ser His Gly Val
1               5                   10                  15

<210> SEQ ID NO 66
<211> LENGTH: 12
<212> TYPE: PRT
<213> ORGANISM: Loligo vulgaris

<400> SEQUENCE: 66

Thr Gly Thr Ser Val Ser Thr Val Ser His Gly Val
1               5                   10

<210> SEQ ID NO 67
<211> LENGTH: 10
<212> TYPE: PRT
<213> ORGANISM: Loligo vulgaris

<400> SEQUENCE: 67

His Ser Val Ser Thr Val Ser His Gly Ala
1               5                   10
```

<210> SEQ ID NO 68
<211> LENGTH: 14
<212> TYPE: PRT
<213> ORGANISM: Loligo vulgaris

<400> SEQUENCE: 68

Ala Gly Ser Ser Ile Ser Thr Val Ser His Gly Val His Ala
1               5                   10

<210> SEQ ID NO 69
<211> LENGTH: 14
<212> TYPE: PRT
<213> ORGANISM: Loligo vulgaris

<400> SEQUENCE: 69

Thr Gly Ser Ser Ile Ser Thr Val Ser His Gly Val His Ser
1               5                   10

<210> SEQ ID NO 70
<211> LENGTH: 13
<212> TYPE: PRT
<213> ORGANISM: Loligo vulgaris

<400> SEQUENCE: 70

His Ile Gly Thr Ser Val Ser Ser Val Ser His Gly Ala
1               5                   10

<210> SEQ ID NO 71
<211> LENGTH: 13
<212> TYPE: PRT
<213> ORGANISM: Loligo vulgaris

<400> SEQUENCE: 71

His Val Gly Thr Ser Val His Ser Val Ser His Gly Val
1               5                   10

<210> SEQ ID NO 72
<211> LENGTH: 11
<212> TYPE: PRT
<213> ORGANISM: Loligo vulgaris

<400> SEQUENCE: 72

His Ala Ser Thr Thr Thr His Ser Ile Gly Leu
1               5                   10

<210> SEQ ID NO 73
<211> LENGTH: 9
<212> TYPE: PRT
<213> ORGANISM: Loligo vulgaris

<400> SEQUENCE: 73

His Ser Val Ser His Val Ser His Gly
1               5

<210> SEQ ID NO 74
<211> LENGTH: 13
<212> TYPE: PRT
<213> ORGANISM: Loligo vulgaris

<400> SEQUENCE: 74

Val Ala His His Gly Thr Ile Ser Arg Arg Tyr Ala Ile
1               5                   10

<210> SEQ ID NO 75
<211> LENGTH: 9

-continued

```
<212> TYPE: PRT
<213> ORGANISM: Loligo vulgaris

<400> SEQUENCE: 75

His Ser Val Ser His Val Ser His Gly
1               5

<210> SEQ ID NO 76
<211> LENGTH: 13
<212> TYPE: PRT
<213> ORGANISM: Loligo vulgaris

<400> SEQUENCE: 76

Val Ala His His Gly Thr Ile Ser Arg Arg Tyr Ala Ile
1               5                   10

<210> SEQ ID NO 77
<211> LENGTH: 14
<212> TYPE: PRT
<213> ORGANISM: Loligo vulgaris

<400> SEQUENCE: 77

Ser His Gly Val Ser His Thr Ala Gly Tyr Ser Ser His Tyr
1               5                   10

<210> SEQ ID NO 78
<211> LENGTH: 10
<212> TYPE: PRT
<213> ORGANISM: Loligo vulgaris

<400> SEQUENCE: 78

Gly His Ala Val Thr His Thr Val His His
1               5                   10

<210> SEQ ID NO 79
<211> LENGTH: 14
<212> TYPE: PRT
<213> ORGANISM: Loligo vulgaris

<400> SEQUENCE: 79

Ser Ala Gly Gly Thr Thr Val Ser His Ser Thr His Gly Val
1               5                   10

<210> SEQ ID NO 80
<211> LENGTH: 11
<212> TYPE: PRT
<213> ORGANISM: Loligo vulgaris

<400> SEQUENCE: 80

Ala Val Ser His Val Thr His Thr Ile His Ala
1               5                   10

<210> SEQ ID NO 81
<211> LENGTH: 11
<212> TYPE: PRT
<213> ORGANISM: Loligo vulgaris

<400> SEQUENCE: 81

His Ala Val Ser Thr Val Ala His Gly Ile His
1               5                   10

<210> SEQ ID NO 82
<211> LENGTH: 12
<212> TYPE: PRT
<213> ORGANISM: Loligo vulgaris
```

<400> SEQUENCE: 82

Ala Ala Thr Ser Val Ser His Thr Thr His Ser Val
1               5                   10

<210> SEQ ID NO 83
<211> LENGTH: 11
<212> TYPE: PRT
<213> ORGANISM: Loligo vulgaris

<400> SEQUENCE: 83

Ala Val Arg His Thr Thr Val Thr His Ala Val
1               5                   10

<210> SEQ ID NO 84
<211> LENGTH: 13
<212> TYPE: PRT
<213> ORGANISM: Loligo vulgaris

<400> SEQUENCE: 84

Ala Ala Thr Ser Val Lys Thr Val Ser His Gly Tyr His
1               5                   10

<210> SEQ ID NO 85
<211> LENGTH: 15
<212> TYPE: PRT
<213> ORGANISM: Loligo vulgaris

<400> SEQUENCE: 85

Val Gly Ser Thr Ser Val Ser His Thr Thr His Gly Val His His
1               5                   10                  15

<210> SEQ ID NO 86
<211> LENGTH: 14
<212> TYPE: PRT
<213> ORGANISM: Loligo vulgaris

<400> SEQUENCE: 86

Ala Ala Thr Thr Val Ser His Thr Thr His Gly Ala His His
1               5                   10

<210> SEQ ID NO 87
<211> LENGTH: 14
<212> TYPE: PRT
<213> ORGANISM: Loligo vulgaris

<400> SEQUENCE: 87

Ala Ala Ser Ser Val Thr His Thr Thr His Gly Val Ala His
1               5                   10

<210> SEQ ID NO 88
<211> LENGTH: 17
<212> TYPE: PRT
<213> ORGANISM: Loligo vulgaris

<400> SEQUENCE: 88

Ser Ser Tyr Tyr Gly Arg Ser Ala Ser Thr Val Ser His Gly Thr His
1               5                   10                  15

Tyr

<210> SEQ ID NO 89
<211> LENGTH: 12
<212> TYPE: PRT
<213> ORGANISM: Loligo vulgaris

<400> SEQUENCE: 89

Thr Ser Val Ser Gln Val Ser His Thr Ala His Ser
1               5                   10

<210> SEQ ID NO 90
<211> LENGTH: 10
<212> TYPE: PRT
<213> ORGANISM: Loligo vulgaris

<400> SEQUENCE: 90

Val Arg Tyr His Gly Tyr Ser Ile Gly His
1               5                   10

<210> SEQ ID NO 91
<211> LENGTH: 11
<212> TYPE: PRT
<213> ORGANISM: Loligo vulgaris

<400> SEQUENCE: 91

Ala Val Ser His Val Thr His Thr Ile His Ala
1               5                   10

<210> SEQ ID NO 92
<211> LENGTH: 12
<212> TYPE: PRT
<213> ORGANISM: Loligo vulgaris

<400> SEQUENCE: 92

Ala Ala Thr Ser Val Ser His Thr Thr His Ser Val
1               5                   10

<210> SEQ ID NO 93
<211> LENGTH: 14
<212> TYPE: PRT
<213> ORGANISM: Loligo vulgaris

<400> SEQUENCE: 93

Val Gly Ala Ser Val Ser Thr Val Ser His Gly Val His Ala
1               5                   10

<210> SEQ ID NO 94
<211> LENGTH: 12
<212> TYPE: PRT
<213> ORGANISM: Loligo vulgaris

<400> SEQUENCE: 94

Thr Gly Thr Ser Val Ser Thr Val Ser His Gly Val
1               5                   10

<210> SEQ ID NO 95
<211> LENGTH: 12
<212> TYPE: PRT
<213> ORGANISM: Loligo vulgaris

<400> SEQUENCE: 95

Thr Gly Ala Ser Val Ser Thr Val Ser His Gly Leu
1               5                   10

<210> SEQ ID NO 96
<211> LENGTH: 14
<212> TYPE: PRT
<213> ORGANISM: Loligo vulgaris

<400> SEQUENCE: 96

Ala Gly Ser Ser Ile Ser Thr Val Ser His Gly Val His Ala
1               5                   10

<210> SEQ ID NO 97
<211> LENGTH: 14
<212> TYPE: PRT
<213> ORGANISM: Loligo vulgaris

<400> SEQUENCE: 97

Ala Thr Ala Ser Val Ser His Thr His Gly Val His His
1               5                   10

<210> SEQ ID NO 98
<211> LENGTH: 12
<212> TYPE: PRT
<213> ORGANISM: Loligo vulgaris

<400> SEQUENCE: 98

Ala Ala Thr Thr Val Ser His Ser Thr His Ala Val
1               5                   10

<210> SEQ ID NO 99
<211> LENGTH: 12
<212> TYPE: PRT
<213> ORGANISM: Loligo vulgaris

<400> SEQUENCE: 99

Ala Ala Thr Thr Val Ser His Ser Thr His Ala Val
1               5                   10

<210> SEQ ID NO 100
<211> LENGTH: 12
<212> TYPE: PRT
<213> ORGANISM: Loligo vulgaris

<400> SEQUENCE: 100

Gly Ala Thr Thr Tyr Ser His Thr His Ala Val
1               5                   10

<210> SEQ ID NO 101
<211> LENGTH: 9
<212> TYPE: PRT
<213> ORGANISM: Loligo vulgaris

<400> SEQUENCE: 101

Ala Val Ser His Val Thr His Thr Ile
1               5

<210> SEQ ID NO 102
<211> LENGTH: 12
<212> TYPE: PRT
<213> ORGANISM: Loligo vulgaris

<400> SEQUENCE: 102

Ala Ala Thr Ser Val Ser His Thr His Ser Val
1               5                   10

<210> SEQ ID NO 103
<211> LENGTH: 20
<212> TYPE: PRT
<213> ORGANISM: Loligo vulgaris

<400> SEQUENCE: 103

Val Ile His Gly Gly Ala Thr Leu Ser Thr Val Ser His Gly Val Ser

```
1               5                   10                  15
Glu Gln Ile Asp
            20

<210> SEQ ID NO 104
<211> LENGTH: 14
<212> TYPE: PRT
<213> ORGANISM: Loligo vulgaris

<400> SEQUENCE: 104

Ala Gly Ser Ser Ile Ser Thr Val Ser His Gly Val His Ala
1               5                   10

<210> SEQ ID NO 105
<211> LENGTH: 10
<212> TYPE: PRT
<213> ORGANISM: Loligo vulgaris

<400> SEQUENCE: 105

Gly His Ala Val Thr His Thr Val His His
1               5                   10

<210> SEQ ID NO 106
<211> LENGTH: 14
<212> TYPE: PRT
<213> ORGANISM: Loligo vulgaris

<400> SEQUENCE: 106

Ser Ala Gly Gly Thr Thr Val Ser His Ser Thr His Gly Val
1               5                   10

<210> SEQ ID NO 107
<211> LENGTH: 11
<212> TYPE: PRT
<213> ORGANISM: Loligo vulgaris

<400> SEQUENCE: 107

Ala Val Arg His Thr Thr Val Thr His Ala Val
1               5                   10

<210> SEQ ID NO 108
<211> LENGTH: 13
<212> TYPE: PRT
<213> ORGANISM: Loligo vulgaris

<400> SEQUENCE: 108

Ala Ala Thr Ser Val Lys Thr Val Ser His Gly Tyr His
1               5                   10

<210> SEQ ID NO 109
<211> LENGTH: 15
<212> TYPE: PRT
<213> ORGANISM: Loligo vulgaris

<400> SEQUENCE: 109

Val Gly Ser Thr Ser Val Ser His Thr Thr His Gly Val His His
1               5                   10                  15

<210> SEQ ID NO 110
<211> LENGTH: 6
<212> TYPE: PRT
<213> ORGANISM: Loligo vulgaris

<400> SEQUENCE: 110
```

Gly Ala Ala Phe His Tyr
1               5

<210> SEQ ID NO 111
<211> LENGTH: 14
<212> TYPE: PRT
<213> ORGANISM: Loligo vulgaris

<400> SEQUENCE: 111

Ala Ala Thr Thr Val Ser His Thr Thr His Gly Ala His His
1               5                   10

<210> SEQ ID NO 112
<211> LENGTH: 14
<212> TYPE: PRT
<213> ORGANISM: Loligo vulgaris

<400> SEQUENCE: 112

Ala Ala Ser Ser Val Thr His Thr Thr His Gly Val Ala His
1               5                   10

<210> SEQ ID NO 113
<211> LENGTH: 11
<212> TYPE: PRT
<213> ORGANISM: Loligo vulgaris

<400> SEQUENCE: 113

Ala Ala Ala Val Ser His Thr Thr His His Ala
1               5                   10

<210> SEQ ID NO 114
<211> LENGTH: 11
<212> TYPE: PRT
<213> ORGANISM: Loligo vulgaris

<400> SEQUENCE: 114

Ala Ala Thr Ala Val Ser His Thr Thr His His
1               5                   10

<210> SEQ ID NO 115
<211> LENGTH: 10
<212> TYPE: PRT
<213> ORGANISM: Loligo vulgaris

<400> SEQUENCE: 115

Val Gly Ala Ala Val Ser Thr Val His His
1               5                   10

<210> SEQ ID NO 116
<211> LENGTH: 10
<212> TYPE: PRT
<213> ORGANISM: Loligo vulgaris

<400> SEQUENCE: 116

Val Gly Gly Ala Val Ser Thr Val His His
1               5                   10

<210> SEQ ID NO 117
<211> LENGTH: 11
<212> TYPE: PRT
<213> ORGANISM: Loligo vulgaris

<400> SEQUENCE: 117

Gly Val Ala Ala Tyr Ser His Ser Val His His
1               5                   10

<210> SEQ ID NO 118
<211> LENGTH: 13
<212> TYPE: PRT
<213> ORGANISM: Loligo vulgaris

<400> SEQUENCE: 118

Val Ser Ser Val Ser Thr Val Ser His Gly Leu His His
1               5                   10

<210> SEQ ID NO 119
<211> LENGTH: 10
<212> TYPE: PRT
<213> ORGANISM: Loligo vulgaris

<400> SEQUENCE: 119

Val Gly Ala Ala Val Ser Thr Val His His
1               5                   10

<210> SEQ ID NO 120
<211> LENGTH: 10
<212> TYPE: PRT
<213> ORGANISM: Loligo vulgaris

<400> SEQUENCE: 120

Val Gly Gly Ala Val Ser Thr Val His His
1               5                   10

<210> SEQ ID NO 121
<211> LENGTH: 11
<212> TYPE: PRT
<213> ORGANISM: Loligo vulgaris

<400> SEQUENCE: 121

Gly Val Ala Ala Tyr Ser His Ser Val His His
1               5                   10

<210> SEQ ID NO 122
<211> LENGTH: 14
<212> TYPE: PRT
<213> ORGANISM: Loligo vulgaris

<400> SEQUENCE: 122

Val Ala Ser Ser Val Ser His Thr Thr His Gly Val His His
1               5                   10

<210> SEQ ID NO 123
<211> LENGTH: 12
<212> TYPE: PRT
<213> ORGANISM: Loligo vulgaris

<400> SEQUENCE: 123

Ala Ala Thr Thr Val Ser Arg Thr Thr His His Ala
1               5                   10

<210> SEQ ID NO 124
<211> LENGTH: 12
<212> TYPE: PRT
<213> ORGANISM: Loligo vulgaris

<400> SEQUENCE: 124

Ala Ala Thr Ala Val Ser His Val Thr His His Ala
1               5                   10

-continued

<210> SEQ ID NO 125
<211> LENGTH: 12
<212> TYPE: PRT
<213> ORGANISM: Loligo vulgaris

<400> SEQUENCE: 125

Ala Ala Thr Ser Val Ser Arg Thr Thr His His Ala
1               5                   10

<210> SEQ ID NO 126
<211> LENGTH: 12
<212> TYPE: PRT
<213> ORGANISM: Loligo vulgaris

<400> SEQUENCE: 126

Ala Thr Ala Ala Val Ser His Thr Thr His His Ala
1               5                   10

<210> SEQ ID NO 127
<211> LENGTH: 12
<212> TYPE: PRT
<213> ORGANISM: Loligo vulgaris

<400> SEQUENCE: 127

Ala Ala Thr Ala Val Ser His Thr Thr His His Ala
1               5                   10

<210> SEQ ID NO 128
<211> LENGTH: 12
<212> TYPE: PRT
<213> ORGANISM: Loligo vulgaris

<400> SEQUENCE: 128

Ala Ala Thr Ala Val Ser His Thr Thr His His Ala
1               5                   10

<210> SEQ ID NO 129
<211> LENGTH: 12
<212> TYPE: PRT
<213> ORGANISM: Loligo vulgaris

<400> SEQUENCE: 129

Ala Ala Thr Thr Val Ser Arg Thr Thr His His Ala
1               5                   10

<210> SEQ ID NO 130
<211> LENGTH: 11
<212> TYPE: PRT
<213> ORGANISM: Loligo vulgaris

<400> SEQUENCE: 130

Ala Ala Ala Val Ser His Val Thr His His Ala
1               5                   10

<210> SEQ ID NO 131
<211> LENGTH: 12
<212> TYPE: PRT
<213> ORGANISM: Loligo vulgaris

<400> SEQUENCE: 131

Ala Ala Thr Ser Val Ser His Thr Thr His His Ala
1               5                   10

<210> SEQ ID NO 132
<211> LENGTH: 12

```
<212> TYPE: PRT
<213> ORGANISM: Loligo vulgaris

<400> SEQUENCE: 132

Ala Ala Thr Ala Val Ser His Thr His His Ala
1               5                   10

<210> SEQ ID NO 133
<211> LENGTH: 12
<212> TYPE: PRT
<213> ORGANISM: Loligo vulgaris

<400> SEQUENCE: 133

Ala Ala Thr Ala Val Ser His Thr His His Ala
1               5                   10

<210> SEQ ID NO 134
<211> LENGTH: 12
<212> TYPE: PRT
<213> ORGANISM: Loligo vulgaris

<400> SEQUENCE: 134

Ala Ala Thr Ser Val Ser Arg Thr Thr His His Ala
1               5                   10

<210> SEQ ID NO 135
<211> LENGTH: 12
<212> TYPE: PRT
<213> ORGANISM: Loligo vulgaris

<400> SEQUENCE: 135

Ala Thr Ala Ala Val Ser His Thr Thr His His Ala
1               5                   10

<210> SEQ ID NO 136
<211> LENGTH: 12
<212> TYPE: PRT
<213> ORGANISM: Loligo vulgaris

<400> SEQUENCE: 136

Ala Ala Thr Ala Val Ser His Thr His His Ala
1               5                   10

<210> SEQ ID NO 137
<211> LENGTH: 12
<212> TYPE: PRT
<213> ORGANISM: Loligo vulgaris

<400> SEQUENCE: 137

Ala Ala Thr Ala Val Ser His Val Thr His His Ala
1               5                   10

<210> SEQ ID NO 138
<211> LENGTH: 9
<212> TYPE: PRT
<213> ORGANISM: Loligo vulgaris

<400> SEQUENCE: 138

His Thr Val Ser His Val Ser His Gly
1               5

<210> SEQ ID NO 139
<211> LENGTH: 13
<212> TYPE: PRT
<213> ORGANISM: Loligo vulgaris
```

```
<400> SEQUENCE: 139

Val Ala His His Ser Val Val Ser Arg Arg Tyr Ala Ile
1               5                   10

<210> SEQ ID NO 140
<211> LENGTH: 12
<212> TYPE: PRT
<213> ORGANISM: Loligo vulgaris

<400> SEQUENCE: 140

Ala Ala Thr Ser Val Ser His Thr Thr His His Ala
1               5                   10

<210> SEQ ID NO 141
<211> LENGTH: 12
<212> TYPE: PRT
<213> ORGANISM: Loligo vulgaris

<400> SEQUENCE: 141

Ala Ala Thr Ala Val Ser His Thr Thr His His Ala
1               5                   10

<210> SEQ ID NO 142
<211> LENGTH: 12
<212> TYPE: PRT
<213> ORGANISM: Loligo vulgaris

<400> SEQUENCE: 142

Ala Ala Thr Ala Val Ser His Thr Thr His His Ala
1               5                   10

<210> SEQ ID NO 143
<211> LENGTH: 12
<212> TYPE: PRT
<213> ORGANISM: Loligo vulgaris

<400> SEQUENCE: 143

Ala Ala Thr Ala Val Ser His Thr Thr His His Ala
1               5                   10

<210> SEQ ID NO 144
<211> LENGTH: 11
<212> TYPE: PRT
<213> ORGANISM: Loligo vulgaris

<400> SEQUENCE: 144

Ala Ala Ala Val Ser His Val Thr His His Ala
1               5                   10

<210> SEQ ID NO 145
<211> LENGTH: 11
<212> TYPE: PRT
<213> ORGANISM: Loligo vulgaris

<400> SEQUENCE: 145

Ala Ala Thr Ala Val His Thr Thr His His Ala
1               5                   10

<210> SEQ ID NO 146
<211> LENGTH: 12
<212> TYPE: PRT
<213> ORGANISM: Loligo vulgaris

<400> SEQUENCE: 146
```

Val Gly Ala Ala Val Ser His Val Thr His His Ala
1               5                   10

<210> SEQ ID NO 147
<211> LENGTH: 12
<212> TYPE: PRT
<213> ORGANISM: Loligo vulgaris

<400> SEQUENCE: 147

Val Ala Thr Ser Val Ser Arg Thr Thr His His Ala
1               5                   10

<210> SEQ ID NO 148
<211> LENGTH: 12
<212> TYPE: PRT
<213> ORGANISM: Loligo vulgaris

<400> SEQUENCE: 148

Ala Ala Thr Ala Val Ser His Thr Thr His His Ala
1               5                   10

<210> SEQ ID NO 149
<211> LENGTH: 10
<212> TYPE: PRT
<213> ORGANISM: Loligo vulgaris

<400> SEQUENCE: 149

Ser Ala Thr Ala Val Ser His Thr Ser His
1               5                   10

<210> SEQ ID NO 150
<211> LENGTH: 11
<212> TYPE: PRT
<213> ORGANISM: Loligo vulgaris

<400> SEQUENCE: 150

Ala Ser Ser Ala Val Ser His Thr Ser His His
1               5                   10

<210> SEQ ID NO 151
<211> LENGTH: 12
<212> TYPE: PRT
<213> ORGANISM: Loligo vulgaris

<400> SEQUENCE: 151

Val Ala Thr Val Thr Ser Gln Thr Ser His His Val
1               5                   10

<210> SEQ ID NO 152
<211> LENGTH: 10
<212> TYPE: PRT
<213> ORGANISM: Loligo vulgaris

<400> SEQUENCE: 152

Ala Ala Ser Ala Val Ser Thr Ser Thr His
1               5                   10

<210> SEQ ID NO 153
<211> LENGTH: 12
<212> TYPE: PRT
<213> ORGANISM: Loligo vulgaris

<400> SEQUENCE: 153

Val Ala Thr Ser Val Ser Arg Thr Thr His His Ala

```
<210> SEQ ID NO 154
<211> LENGTH: 12
<212> TYPE: PRT
<213> ORGANISM: Loligo vulgaris

<400> SEQUENCE: 154

Ala Ala Thr Ala Val Ser His Val Thr His His Ala
1               5                   10

<210> SEQ ID NO 155
<211> LENGTH: 13
<212> TYPE: PRT
<213> ORGANISM: Loligo vulgaris

<400> SEQUENCE: 155

Val Ala His His Ser Val Val Ser Arg Arg Tyr Ala Ile
1               5                   10

<210> SEQ ID NO 156
<211> LENGTH: 11
<212> TYPE: PRT
<213> ORGANISM: Loligo vulgaris

<400> SEQUENCE: 156

His Ala Val Gly Ala Val Ser Thr Leu His His
1               5                   10

<210> SEQ ID NO 157
<211> LENGTH: 9
<212> TYPE: PRT
<213> ORGANISM: Loligo vulgaris

<400> SEQUENCE: 157

His Ser Val Ala Val Gly Val His His
1               5

<210> SEQ ID NO 158
<211> LENGTH: 12
<212> TYPE: PRT
<213> ORGANISM: Loligo vulgaris

<400> SEQUENCE: 158

Ala Ala Thr Ala Val Ser His Thr Thr His His Ala
1               5                   10

<210> SEQ ID NO 159
<211> LENGTH: 12
<212> TYPE: PRT
<213> ORGANISM: Loligo vulgaris

<400> SEQUENCE: 159

Ala Ala Thr Ala Val Ser His Val Thr His His Ala
1               5                   10

<210> SEQ ID NO 160
<211> LENGTH: 13
<212> TYPE: PRT
<213> ORGANISM: Loligo vulgaris

<400> SEQUENCE: 160

Val Ala His His Ser Val Val Ser Arg Arg Tyr Ala Ile
1               5                   10
```

<210> SEQ ID NO 161
<211> LENGTH: 35
<212> TYPE: PRT
<213> ORGANISM: Loligo vulgaris

<400> SEQUENCE: 161

Gly Tyr Gly Leu Gly Gly Leu Tyr Gly Tyr Gly Leu Gly Gly Leu
1               5                   10                  15
His Tyr Gly Gly Tyr Gly Leu Gly Gly Leu His Tyr Gly Gly Tyr Gly
                20                  25                  30
Leu His Tyr
        35

<210> SEQ ID NO 162
<211> LENGTH: 31
<212> TYPE: PRT
<213> ORGANISM: Loligo vulgaris

<400> SEQUENCE: 162

Gly Val Gly Gly Leu Tyr Gly Gly Tyr Gly Leu Gly Gly Leu His Gly
1               5                   10                  15
Gly Tyr Gly Leu Gly Gly Ile Tyr Gly Gly Tyr Gly Ala His Tyr
                20                  25                  30

<210> SEQ ID NO 163
<211> LENGTH: 27
<212> TYPE: PRT
<213> ORGANISM: Loligo vulgaris

<400> SEQUENCE: 163

Gly Val Gly Gly Tyr Gly Met Gly Gly Leu Tyr Gly Gly Tyr Gly Leu
1               5                   10                  15
Gly Gly Val Tyr Gly Gly Tyr Gly Leu Gly Gly
                20                  25

<210> SEQ ID NO 164
<211> LENGTH: 8
<212> TYPE: PRT
<213> ORGANISM: Loligo vulgaris

<400> SEQUENCE: 164

Gly Tyr Gly Leu Gly Val Gly Leu
1               5

<210> SEQ ID NO 165
<211> LENGTH: 28
<212> TYPE: PRT
<213> ORGANISM: Loligo vulgaris

<400> SEQUENCE: 165

Leu Gly Leu Gly Tyr Gly Gly Tyr Gly Leu Gly Leu Gly Tyr Gly Leu
1               5                   10                  15
Gly His Gly Tyr Gly Leu Gly Leu Gly Ala Gly Ile
                20                  25

<210> SEQ ID NO 166
<211> LENGTH: 15
<212> TYPE: PRT
<213> ORGANISM: Loligo vulgaris

<400> SEQUENCE: 166

Gly Leu Gly Leu Gly Tyr Gly Tyr Gly Leu Gly His Gly Leu Gly

<210> SEQ ID NO 167
<211> LENGTH: 12
<212> TYPE: PRT
<213> ORGANISM: Loligo vulgaris

<400> SEQUENCE: 167

Gly Leu Gly Leu Gly Tyr Gly Leu Gly Leu Gly Leu
1               5                   10

<210> SEQ ID NO 168
<211> LENGTH: 30
<212> TYPE: PRT
<213> ORGANISM: Loligo vulgaris

<400> SEQUENCE: 168

Met Gly Gly Leu Tyr Gly Gly Tyr Gly Leu Gly Gly Val Tyr Gly Gly
1               5                   10                  15

Tyr Gly Leu Gly Gly Ile Tyr Gly Gly Tyr Gly Ala His Tyr
            20                  25                  30

<210> SEQ ID NO 169
<211> LENGTH: 40
<212> TYPE: PRT
<213> ORGANISM: Loligo vulgaris

<400> SEQUENCE: 169

Gly Val Gly Gly Leu Tyr Gly Gly Tyr Gly Leu Gly Gly Leu Tyr Gly
1               5                   10                  15

Gly Tyr Gly Leu Gly Gly Leu His Gly Gly Tyr Ser Leu Gly Gly Leu
            20                  25                  30

Tyr Gly Gly Tyr Gly Ala His Tyr
            35                  40

<210> SEQ ID NO 170
<211> LENGTH: 33
<212> TYPE: PRT
<213> ORGANISM: Loligo vulgaris

<400> SEQUENCE: 170

Gly Val Gly Gly Leu Tyr Gly Gly Tyr Gly Leu Gly Gly Leu His Tyr
1               5                   10                  15

Gly Gly Tyr Gly Leu Gly Gly Leu His Tyr Gly Gly Tyr Gly Leu His
            20                  25                  30

Tyr

<210> SEQ ID NO 171
<211> LENGTH: 15
<212> TYPE: PRT
<213> ORGANISM: Loligo vulgaris

<400> SEQUENCE: 171

Tyr Gly Tyr Gly Gly Leu Tyr Gly Gly Leu Tyr Gly Gly Leu Gly
1               5                   10                  15

<210> SEQ ID NO 172
<211> LENGTH: 15
<212> TYPE: PRT
<213> ORGANISM: Loligo vulgaris

<400> SEQUENCE: 172

```
Tyr Gly Tyr Gly Gly Leu Tyr Gly Gly Leu Tyr Gly Gly Leu Gly
1               5                   10                  15
```

<210> SEQ ID NO 173
<211> LENGTH: 41
<212> TYPE: PRT
<213> ORGANISM: Loligo vulgaris

<400> SEQUENCE: 173

```
Val Ala Tyr Gly Gly Trp Gly Tyr Gly Leu Gly Leu His Gly Gly
1               5                   10                  15

Trp Gly Tyr Gly Leu Gly Gly Leu His Gly Gly Trp Gly Tyr Ala Leu
            20                  25                  30

Gly Gly Leu Tyr Gly Gly Leu His Tyr
        35                  40
```

<210> SEQ ID NO 174
<211> LENGTH: 14
<212> TYPE: PRT
<213> ORGANISM: Loligo vulgaris

<400> SEQUENCE: 174

```
Val Gly Leu Gly Tyr Gly Gly Leu Tyr Gly Gly Leu His Tyr
1               5                   10
```

<210> SEQ ID NO 175
<211> LENGTH: 19
<212> TYPE: PRT
<213> ORGANISM: Loligo vulgaris

<400> SEQUENCE: 175

```
Val Gly Tyr Gly Gly Phe Gly Leu Gly Phe Gly Gly Leu Tyr Gly Gly
1               5                   10                  15

Leu His Tyr
```

<210> SEQ ID NO 176
<211> LENGTH: 21
<212> TYPE: PRT
<213> ORGANISM: Loligo vulgaris

<400> SEQUENCE: 176

```
Ser Leu Gly Ala Tyr Gly Gly Tyr Gly Leu Gly Gly Leu Ile Gly Gly
1               5                   10                  15

His Ser Val Tyr His
            20
```

<210> SEQ ID NO 177
<211> LENGTH: 21
<212> TYPE: PRT
<213> ORGANISM: Loligo vulgaris

<400> SEQUENCE: 177

```
Ser Leu Gly Ala Tyr Gly Gly Tyr Gly Leu Gly Gly Ile Val Gly Gly
1               5                   10                  15

Tyr Gly Ala Tyr Asn
            20
```

<210> SEQ ID NO 178
<211> LENGTH: 19
<212> TYPE: PRT
<213> ORGANISM: Loligo vulgaris

<400> SEQUENCE: 178

```
Val Gly Tyr Gly Gly Phe Gly Leu Gly Phe Gly Gly Leu Tyr Gly Gly
1               5                   10                  15

Leu His Tyr
```

<210> SEQ ID NO 179
<211> LENGTH: 21
<212> TYPE: PRT
<213> ORGANISM: Loligo vulgaris

<400> SEQUENCE: 179

```
Val Gly Leu Gly Tyr Gly Gly Phe Gly Leu Gly Tyr Gly Gly Leu Tyr
1               5                   10                  15

Gly Gly Phe Gly Tyr
            20
```

<210> SEQ ID NO 180
<211> LENGTH: 12
<212> TYPE: PRT
<213> ORGANISM: Loligo vulgaris

<400> SEQUENCE: 180

```
Val Ala Tyr Gly Gly Leu Gly Tyr Gly Phe Gly Phe
1               5                   10
```

<210> SEQ ID NO 181
<211> LENGTH: 13
<212> TYPE: PRT
<213> ORGANISM: Loligo vulgaris

<400> SEQUENCE: 181

```
Gly Tyr Gly Gly Leu Tyr Gly Gly Leu Gly Tyr His Tyr
1               5                   10
```

<210> SEQ ID NO 182
<211> LENGTH: 16
<212> TYPE: PRT
<213> ORGANISM: Loligo vulgaris

<400> SEQUENCE: 182

```
Tyr Gly Tyr Gly Gly Leu Tyr Gly Gly Leu Tyr Gly Gly Leu Gly Tyr
1               5                   10                  15
```

<210> SEQ ID NO 183
<211> LENGTH: 22
<212> TYPE: PRT
<213> ORGANISM: Loligo vulgaris

<400> SEQUENCE: 183

```
Val Gly Tyr Gly Gly Tyr Gly Leu Gly Ala Tyr Gly Ala Tyr Gly Leu
1               5                   10                  15

Gly Tyr Gly Leu His Tyr
            20
```

<210> SEQ ID NO 184
<211> LENGTH: 22
<212> TYPE: PRT
<213> ORGANISM: Loligo vulgaris

<400> SEQUENCE: 184

```
Val Gly Tyr Gly Gly Tyr Gly Leu Gly Ala Tyr Gly Ala Tyr Gly Leu
1               5                   10                  15

Gly Tyr Gly Leu His Tyr
```

20

<210> SEQ ID NO 185
<211> LENGTH: 9
<212> TYPE: PRT
<213> ORGANISM: Loligo vulgaris

<400> SEQUENCE: 185

Val Gly Tyr Ala Gly Tyr Gly Leu Gly
1               5

<210> SEQ ID NO 186
<211> LENGTH: 9
<212> TYPE: PRT
<213> ORGANISM: Loligo vulgaris

<400> SEQUENCE: 186

Tyr Gly Gly Phe Gly Tyr Gly Leu Tyr
1               5

<210> SEQ ID NO 187
<211> LENGTH: 20
<212> TYPE: PRT
<213> ORGANISM: Loligo vulgaris

<400> SEQUENCE: 187

Gly Tyr Gly Gly Leu Tyr Gly His Tyr Gly Tyr Gly Leu Gly Gly
1               5                   10                  15

Ala Tyr Gly His
            20

<210> SEQ ID NO 188
<211> LENGTH: 51
<212> TYPE: PRT
<213> ORGANISM: Loligo vulgaris

<400> SEQUENCE: 188

Gly Ile Gly Gly Val Tyr Gly His Gly Ile Gly Gly Leu Gly Gly Val
1               5                   10                  15

Tyr Gly His Gly Ile Gly Gly Val Tyr Gly His Gly Ile Gly Gly Leu
            20                  25                  30

Tyr Gly His Gly Phe Gly Gly Ala Tyr Gly Tyr Gly Gly Tyr Gly
        35                  40                  45

Ile Gly Gly
    50

<210> SEQ ID NO 189
<211> LENGTH: 53
<212> TYPE: PRT
<213> ORGANISM: Loligo vulgaris

<400> SEQUENCE: 189

Val Thr Tyr Gly Gly Leu Gly Leu Gly Gly Leu Gly Tyr Gly Gly Leu
1               5                   10                  15

Gly Tyr Gly Gly Leu Gly Tyr Gly Gly Leu Gly Tyr Gly Gly Leu Gly
            20                  25                  30

Tyr Gly Gly Leu Gly Tyr Gly Gly Leu Gly Tyr Gly Gly Leu Gly Ala
        35                  40                  45

Gly Gly Leu Tyr Gly
    50

```
<210> SEQ ID NO 190
<211> LENGTH: 21
<212> TYPE: PRT
<213> ORGANISM: Loligo vulgaris

<400> SEQUENCE: 190

Gly Ala Val Gly Leu Gly Tyr Gly Leu Gly Gly Tyr Gly Leu
1               5                   10                  15

Tyr Gly Leu His Leu
            20

<210> SEQ ID NO 191
<211> LENGTH: 12
<212> TYPE: PRT
<213> ORGANISM: Loligo vulgaris

<400> SEQUENCE: 191

Ala Leu Gly Leu Gly Leu Tyr Gly Gly Ala His Leu
1               5                   10

<210> SEQ ID NO 192
<211> LENGTH: 12
<212> TYPE: PRT
<213> ORGANISM: Loligo vulgaris

<400> SEQUENCE: 192

Gly Leu Gly Leu Asn Tyr Gly Val Tyr Gly Leu His
1               5                   10

<210> SEQ ID NO 193
<211> LENGTH: 20
<212> TYPE: PRT
<213> ORGANISM: Loligo vulgaris

<400> SEQUENCE: 193

Gly Tyr Gly Gly Trp Gly Tyr Gly Leu Gly Gly Trp Gly His Gly Leu
1               5                   10                  15

Gly Gly Leu Gly
            20

<210> SEQ ID NO 194
<211> LENGTH: 17
<212> TYPE: PRT
<213> ORGANISM: Loligo vulgaris

<400> SEQUENCE: 194

Tyr Gly Gly Ile Gly Leu Gly Gly Leu Tyr Gly Gly Tyr Gly Ala His
1               5                   10                  15

Phe

<210> SEQ ID NO 195
<211> LENGTH: 21
<212> TYPE: PRT
<213> ORGANISM: Loligo vulgaris

<400> SEQUENCE: 195

His Ser Val Gly Trp Gly Leu Gly Gly Trp Gly Gly Tyr Gly Leu Gly
1               5                   10                  15

Tyr Gly Val His Ala
            20

<210> SEQ ID NO 196
<211> LENGTH: 21
```

```
<212> TYPE: PRT
<213> ORGANISM: Loligo vulgaris

<400> SEQUENCE: 196

Ala Leu Gly Ala Tyr Gly Gly Tyr Gly Phe Gly Gly Ile Val Gly Gly
1               5                   10                  15

His Ser Val Tyr His
            20

<210> SEQ ID NO 197
<211> LENGTH: 16
<212> TYPE: PRT
<213> ORGANISM: Loligo vulgaris

<400> SEQUENCE: 197

Ala Leu Gly Gly Tyr Gly Gly Tyr Gly Leu Gly Gly Ile Val Gly Gly
1               5                   10                  15

<210> SEQ ID NO 198
<211> LENGTH: 21
<212> TYPE: PRT
<213> ORGANISM: Loligo vulgaris

<400> SEQUENCE: 198

Ala Leu Gly Ala Tyr Gly Gly Tyr Gly Leu Gly Gly Leu Val Gly Gly
1               5                   10                  15

Phe Gly Ala Tyr His
            20

<210> SEQ ID NO 199
<211> LENGTH: 39
<212> TYPE: PRT
<213> ORGANISM: Loligo vulgaris

<400> SEQUENCE: 199

Val Gly Phe Gly Gly Tyr Gly Leu Gly Tyr Gly Leu Gly Gly Tyr
1               5                   10                  15

Gly Leu Gly Gly Tyr Gly Leu Gly Gly Tyr Gly Leu Gly Gly Leu Val
            20                  25                  30

Gly Gly Tyr Gly Ser Tyr His
            35

<210> SEQ ID NO 200
<211> LENGTH: 25
<212> TYPE: PRT
<213> ORGANISM: Loligo vulgaris

<400> SEQUENCE: 200

Val Gly Tyr Gly Gly Tyr Gly Leu Gly Tyr Gly Gly Tyr Gly Leu
1               5                   10                  15

Gly Gly Leu Thr Gly Gly Tyr Gly Val
            20                  25

<210> SEQ ID NO 201
<211> LENGTH: 15
<212> TYPE: PRT
<213> ORGANISM: Loligo vulgaris

<400> SEQUENCE: 201

Gly Tyr Gly Leu Gly Leu Gly Tyr Gly Leu Gly Leu Gly Ala Gly
1               5                   10                  15
```

```
<210> SEQ ID NO 202
<211> LENGTH: 21
<212> TYPE: PRT
<213> ORGANISM: Loligo vulgaris

<400> SEQUENCE: 202

Leu Gly Leu Gly Tyr Gly Tyr Gly Leu Gly Leu Gly Tyr Gly Leu Gly
1               5                   10                  15

Leu Gly Ala Gly Ile
            20

<210> SEQ ID NO 203
<211> LENGTH: 17
<212> TYPE: PRT
<213> ORGANISM: Loligo vulgaris

<400> SEQUENCE: 203

His Leu Gly Leu Gly Leu Gly Tyr Gly Tyr Gly Leu Gly His Gly Leu
1               5                   10                  15

Gly

<210> SEQ ID NO 204
<211> LENGTH: 16
<212> TYPE: PRT
<213> ORGANISM: Loligo vulgaris

<400> SEQUENCE: 204

Gly Leu Gly Leu Gly Tyr Gly Leu Gly Leu Gly Tyr Gly Tyr Gly Val
1               5                   10                  15

<210> SEQ ID NO 205
<211> LENGTH: 15
<212> TYPE: PRT
<213> ORGANISM: Loligo vulgaris

<400> SEQUENCE: 205

Gly Tyr Gly Leu Gly Leu Gly Leu Gly Ala Gly Tyr Gly Tyr
1               5                   10                  15

<210> SEQ ID NO 206
<211> LENGTH: 19
<212> TYPE: PRT
<213> ORGANISM: Loligo vulgaris

<400> SEQUENCE: 206

Val Gly Gly Tyr Gly Gly Phe Gly Leu Gly Tyr Gly Gly Tyr Gly
1               5                   10                  15

Leu Gly Gly

<210> SEQ ID NO 207
<211> LENGTH: 58
<212> TYPE: PRT
<213> ORGANISM: Loligo vulgaris

<400> SEQUENCE: 207

Val Gly Tyr Gly Gly Leu Tyr Gly His Tyr Gly Gly Tyr Gly Leu Gly
1               5                   10                  15

Gly Val Tyr Gly His Gly Val Gly Leu Gly Val Tyr Gly His Gly
            20                  25                  30

Ile Gly Gly Ala Tyr Gly Gly Tyr Gly Leu Val Gly Gly Leu Tyr
        35                  40                  45

Gly Gly Tyr Gly Gly Tyr Gly Ile Gly Gly
```

<210> SEQ ID NO 208
<211> LENGTH: 19
<212> TYPE: PRT
<213> ORGANISM: Loligo vulgaris

<400> SEQUENCE: 208

Val Gly Gly Tyr Gly Gly Phe Gly Leu Gly Gly Tyr Gly Gly Tyr Gly
1               5                   10                  15

Leu Gly Gly

<210> SEQ ID NO 209
<211> LENGTH: 41
<212> TYPE: PRT
<213> ORGANISM: Loligo vulgaris

<400> SEQUENCE: 209

Val Gly Tyr Gly Gly Leu Tyr Gly His Tyr Gly Gly Tyr Gly Leu Gly
1               5                   10                  15

Gly Val Tyr Gly His Gly Val Gly Leu Gly Gly Val Tyr Gly His Gly
            20                  25                  30

Val Gly Leu Gly Gly Val Tyr Ser His
            35                  40

<210> SEQ ID NO 210
<211> LENGTH: 27
<212> TYPE: PRT
<213> ORGANISM: Loligo vulgaris

<400> SEQUENCE: 210

Gly Ile Gly Gly Ala Tyr Gly Tyr Gly Leu Gly Val Gly Gly Leu
1               5                   10                  15

Tyr Gly Gly Tyr Gly Gly Tyr Gly Ile Gly Gly
            20                  25

<210> SEQ ID NO 211
<211> LENGTH: 19
<212> TYPE: PRT
<213> ORGANISM: Loligo vulgaris

<400> SEQUENCE: 211

Val Leu Ser Gly Gly Leu Gly Leu Ser Gly Leu Ser Gly Gly Tyr Gly
1               5                   10                  15

Thr Tyr Arg

<210> SEQ ID NO 212
<211> LENGTH: 27
<212> TYPE: PRT
<213> ORGANISM: Loligo vulgaris

<400> SEQUENCE: 212

Gly Tyr Gly Gly Val Gly Tyr Gly Leu Gly Tyr Gly Gly Leu Gly
1               5                   10                  15

Tyr Gly Val Gly Gly Leu Tyr Gly Leu Gln Tyr
            20                  25

<210> SEQ ID NO 213
<211> LENGTH: 26
<212> TYPE: PRT
<213> ORGANISM: Loligo vulgaris

```
<400> SEQUENCE: 213

Gly Tyr Gly Gly Trp Gly Tyr Gly Leu Gly Gly Trp Gly His Gly Leu
1               5                   10                  15

Gly Gly Leu Gly Ser Tyr Gly Leu His Tyr
            20                  25

<210> SEQ ID NO 214
<211> LENGTH: 21
<212> TYPE: PRT
<213> ORGANISM: Loligo vulgaris

<400> SEQUENCE: 214

His Ser Val Gly Trp Gly Leu Gly Gly Trp Gly Gly Tyr Gly Leu Gly
1               5                   10                  15

Tyr Gly Val Arg Ser
            20

<210> SEQ ID NO 215
<211> LENGTH: 19
<212> TYPE: PRT
<213> ORGANISM: Loligo vulgaris

<400> SEQUENCE: 215

Tyr Gly Asp Val Tyr Gly Gly Leu Tyr Gly Gly Leu Tyr Gly Leu
1               5                   10                  15

Leu Gly Ala

<210> SEQ ID NO 216
<211> LENGTH: 35
<212> TYPE: PRT
<213> ORGANISM: Loligo vulgaris

<400> SEQUENCE: 216

Val Ala Tyr Gly Gly Leu Gly Leu Gly Ala Leu Gly Tyr Gly Gly Leu
1               5                   10                  15

Gly Tyr Gly Gly Leu Gly Tyr Gly Leu Gly Ala Gly Gly Leu Tyr
            20                  25                  30

Gly Leu His
        35

<210> SEQ ID NO 217
<211> LENGTH: 13
<212> TYPE: PRT
<213> ORGANISM: Loligo vulgaris

<400> SEQUENCE: 217

Gly Tyr Gly Leu Gly Leu Gly Leu Tyr Gly Ala His Leu
1               5                   10

<210> SEQ ID NO 218
<211> LENGTH: 26
<212> TYPE: PRT
<213> ORGANISM: Loligo vulgaris

<400> SEQUENCE: 218

Ala Tyr Gly Gly Trp Gly Tyr Ser Leu Gly Arg Trp Gly Gln Gly Leu
1               5                   10                  15

Gly Gly Leu Gly Thr Tyr Gly Leu His Tyr
            20                  25

<210> SEQ ID NO 219
```

-continued

```
<211> LENGTH: 21
<212> TYPE: PRT
<213> ORGANISM: Loligo vulgaris

<400> SEQUENCE: 219

His Ser Val Gly Trp Gly Leu Gly Gly Trp Gly Gly Tyr Gly Leu Gly
1               5                   10                  15

Tyr Gly Val His Ala
            20

<210> SEQ ID NO 220
<211> LENGTH: 21
<212> TYPE: PRT
<213> ORGANISM: Loligo vulgaris

<400> SEQUENCE: 220

Ala Leu Gly Gly Tyr Gly Gly Tyr Gly Leu Gly Gly Ile Val Gly Gly
1               5                   10                  15

His Ser Val Tyr His
            20

<210> SEQ ID NO 221
<211> LENGTH: 17
<212> TYPE: PRT
<213> ORGANISM: Loligo vulgaris

<400> SEQUENCE: 221

Ala Leu Gly Glu Tyr Gly Gly Tyr Gly Leu Gly Gly Ile Val Gly Gly
1               5                   10                  15

His

<210> SEQ ID NO 222
<211> LENGTH: 20
<212> TYPE: PRT
<213> ORGANISM: Loligo vulgaris

<400> SEQUENCE: 222

Gly Phe Gly Gly Tyr Gly Leu Gly Gly Tyr Gly Leu Gly Gly Tyr Gly
1               5                   10                  15

Leu Gly Gly Tyr
            20

<210> SEQ ID NO 223
<211> LENGTH: 33
<212> TYPE: PRT
<213> ORGANISM: Loligo vulgaris

<400> SEQUENCE: 223

Ile Gly Phe Gly Gly Trp Gly His Gly Tyr Gly Tyr Ser Gly Leu Gly
1               5                   10                  15

Phe Gly Gly Trp Gly His Gly Leu Gly Gly Trp Gly His Gly Tyr Gly
            20                  25                  30

Tyr

<210> SEQ ID NO 224
<211> LENGTH: 33
<212> TYPE: PRT
<213> ORGANISM: Loligo vulgaris

<400> SEQUENCE: 224

Ile Gly Phe Gly Gly Trp Gly His Gly Tyr Gly Tyr Ser Gly Leu Gly
1               5                   10                  15
```

Phe Gly Gly Trp Gly His Gly Leu Gly Gly Trp His Gly Tyr Gly
            20                  25                  30

Tyr

<210> SEQ ID NO 225
<211> LENGTH: 14
<212> TYPE: PRT
<213> ORGANISM: Loligo vulgaris

<400> SEQUENCE: 225

His Ala Val Gly Phe Gly Gly Trp Gly His Gly Phe Gly Tyr
1               5                  10

<210> SEQ ID NO 226
<211> LENGTH: 19
<212> TYPE: PRT
<213> ORGANISM: Loligo vulgaris

<400> SEQUENCE: 226

His Ser Val Ser Tyr Gly Gly Trp Gly Phe Gly His Gly Gly Leu Tyr
1               5                   10                  15

Gly Leu His

<210> SEQ ID NO 227
<211> LENGTH: 16
<212> TYPE: PRT
<213> ORGANISM: Loligo vulgaris

<400> SEQUENCE: 227

His Ala Asp Tyr Gly Val Ser Gly Leu Gly Gly Tyr Val Ser Ser Tyr
1               5                   10                  15

<210> SEQ ID NO 228
<211> LENGTH: 21
<212> TYPE: PRT
<213> ORGANISM: Loligo vulgaris

<400> SEQUENCE: 228

His Ser Val Gly Trp Gly Leu Gly Gly Trp Gly Tyr Gly Leu Gly
1               5                   10                  15

Tyr Gly Val His Ala
            20

<210> SEQ ID NO 229
<211> LENGTH: 21
<212> TYPE: PRT
<213> ORGANISM: Loligo vulgaris

<400> SEQUENCE: 229

Ala Leu Gly Ala Tyr Gly Gly Tyr Gly Phe Gly Gly Ile Val Gly Gly
1               5                   10                  15

His Ser Val Tyr His
            20

<210> SEQ ID NO 230
<211> LENGTH: 39
<212> TYPE: PRT
<213> ORGANISM: Loligo vulgaris

<400> SEQUENCE: 230

Val Gly Phe Gly Gly Tyr Gly Leu Gly Gly Tyr Gly Leu Gly Gly Tyr
1               5                   10                  15

Gly Leu Gly Gly Tyr Gly Leu Gly Tyr Gly Leu Gly Gly Val Val
                20                  25                  30
Gly Gly Phe Gly Gly Tyr His
         35

<210> SEQ ID NO 231
<211> LENGTH: 28
<212> TYPE: PRT
<213> ORGANISM: Loligo vulgaris

<400> SEQUENCE: 231

Phe Gly Tyr Gly Gly Val Gly Tyr Gly Gly Leu Gly Tyr Gly Gly Leu
1               5                   10                  15
Gly Tyr Gly Val Gly Gly Leu Tyr Gly Leu Gln Tyr
            20                  25

<210> SEQ ID NO 232
<211> LENGTH: 31
<212> TYPE: PRT
<213> ORGANISM: Loligo vulgaris

<400> SEQUENCE: 232

Val Ala Tyr Gly Gly Leu Gly Leu Gly Ala Leu Gly Tyr Gly Gly Leu
1               5                   10                  15
Gly Tyr Gly Gly Leu Gly Ala Gly Gly Leu Tyr Gly Leu His Tyr
            20                  25                  30

<210> SEQ ID NO 233
<211> LENGTH: 18
<212> TYPE: PRT
<213> ORGANISM: Loligo vulgaris

<400> SEQUENCE: 233

Ala Gly Leu Gly Tyr Gly Leu Gly Gly Val Tyr Gly Gly Tyr Gly Leu
1               5                   10                  15
His Ala

<210> SEQ ID NO 234
<211> LENGTH: 29
<212> TYPE: PRT
<213> ORGANISM: Loligo vulgaris

<400> SEQUENCE: 234

Tyr Gly Tyr Gly Gly Leu Tyr Gly Gly Leu Gly Tyr His Ala Gly Tyr
1               5                   10                  15
Gly Leu Gly Gly Tyr Gly Leu Gly Tyr Gly Leu His Tyr
            20                  25

<210> SEQ ID NO 235
<211> LENGTH: 14
<212> TYPE: PRT
<213> ORGANISM: Loligo vulgaris

<400> SEQUENCE: 235

Val Gly Trp Gly Leu Gly Gly Leu Tyr Gly Gly Leu His His
1               5                   10

<210> SEQ ID NO 236
<211> LENGTH: 18
<212> TYPE: PRT
<213> ORGANISM: Loligo vulgaris

<400> SEQUENCE: 236

Gly Tyr Gly Gly Tyr Gly Leu Gly Leu Gly Gly Leu Tyr Gly Gly Leu
1               5                   10                  15

His Tyr

<210> SEQ ID NO 237
<211> LENGTH: 18
<212> TYPE: PRT
<213> ORGANISM: Loligo vulgaris

<400> SEQUENCE: 237

Gly Tyr Gly Gly Tyr Gly Leu Gly Phe Gly Gly Leu Tyr Gly Gly Phe
1               5                   10                  15

Gly Tyr

<210> SEQ ID NO 238
<211> LENGTH: 24
<212> TYPE: PRT
<213> ORGANISM: Loligo vulgaris

<400> SEQUENCE: 238

Ala Tyr Gly Tyr Gly Tyr Gly Leu Gly Gly Tyr Gly Gly Tyr Gly Leu
1               5                   10                  15

Tyr Gly Gly Tyr Gly Leu His His
            20

<210> SEQ ID NO 239
<211> LENGTH: 29
<212> TYPE: PRT
<213> ORGANISM: Loligo vulgaris

<400> SEQUENCE: 239

Val Ala Tyr Gly Gly Trp Gly Tyr Gly Leu Gly Gly Leu His Gly Gly
1               5                   10                  15

Trp Gly Tyr Gly Leu Gly Gly Leu Tyr Gly Gly Leu His
            20                  25

<210> SEQ ID NO 240
<211> LENGTH: 18
<212> TYPE: PRT
<213> ORGANISM: Loligo vulgaris

<400> SEQUENCE: 240

Gly Tyr Gly Gly Tyr Gly Leu Gly Leu Gly Gly Leu Tyr Gly Gly Leu
1               5                   10                  15

His Tyr

<210> SEQ ID NO 241
<211> LENGTH: 18
<212> TYPE: PRT
<213> ORGANISM: Loligo vulgaris

<400> SEQUENCE: 241

Gly Tyr Gly Gly Tyr Gly Leu Gly Phe Gly Gly Leu Tyr Gly Gly Phe
1               5                   10                  15

Gly Tyr

<210> SEQ ID NO 242
<211> LENGTH: 30
<212> TYPE: PRT
<213> ORGANISM: Loligo vulgaris

<400> SEQUENCE: 242

Val Gly Tyr Ala Gly Tyr Gly Tyr Gly Leu Gly Ser Tyr Gly Tyr
1               5                   10                  15
Ala Gly Leu Gly Leu Gly Leu Tyr Gly Ala Gly Tyr His Tyr
            20                  25                  30

<210> SEQ ID NO 243
<211> LENGTH: 17
<212> TYPE: PRT
<213> ORGANISM: Loligo vulgaris

<400> SEQUENCE: 243

Tyr Ala Tyr Gly Gly Leu Tyr Gly Gly Tyr Gly Leu Gly Ala Tyr Gly
1               5                   10                  15
Tyr

<210> SEQ ID NO 244
<211> LENGTH: 30
<212> TYPE: PRT
<213> ORGANISM: Loligo vulgaris

<400> SEQUENCE: 244

Val Gly Tyr Ala Gly Tyr Gly Tyr Gly Leu Gly Ala Tyr Gly Tyr
1               5                   10                  15
Ala Gly Leu Gly Leu Gly Leu Tyr Gly Ala Gly Tyr His Tyr
            20                  25                  30

<210> SEQ ID NO 245
<211> LENGTH: 17
<212> TYPE: PRT
<213> ORGANISM: Loligo vulgaris

<400> SEQUENCE: 245

Tyr Ala Tyr Gly Gly Leu Tyr Gly Gly Tyr Gly Leu Gly Ala Tyr Gly
1               5                   10                  15
Tyr

<210> SEQ ID NO 246
<211> LENGTH: 15
<212> TYPE: PRT
<213> ORGANISM: Loligo vulgaris

<400> SEQUENCE: 246

Val Gly Tyr Gly Gly Phe Gly Leu Ala Gly Tyr Gly Tyr Gly Tyr
1               5                   10                  15

<210> SEQ ID NO 247
<211> LENGTH: 24
<212> TYPE: PRT
<213> ORGANISM: Loligo vulgaris

<400> SEQUENCE: 247

Tyr Gly Tyr Gly Gly Leu Tyr Gly Gly Tyr Ala Gly Leu Gly Leu Gly
1               5                   10                  15
Leu Tyr Gly Ala Gly Tyr His Tyr
            20

<210> SEQ ID NO 248
<211> LENGTH: 17
<212> TYPE: PRT
<213> ORGANISM: Loligo vulgaris

<400> SEQUENCE: 248

Tyr Ala Tyr Gly Gly Leu Tyr Gly Gly Tyr Gly Leu Gly Ala Tyr Gly
1               5                   10                  15

Tyr

<210> SEQ ID NO 249
<211> LENGTH: 30
<212> TYPE: PRT
<213> ORGANISM: Loligo vulgaris

<400> SEQUENCE: 249

Val Gly Tyr Ala Gly Tyr Gly Tyr Gly Leu Gly Ala Tyr Gly Gly Tyr
1               5                   10                  15

Ala Gly Leu Gly Leu Gly Leu Tyr Gly Ala Gly Tyr His Tyr
                20                  25                  30

<210> SEQ ID NO 250
<211> LENGTH: 17
<212> TYPE: PRT
<213> ORGANISM: Loligo vulgaris

<400> SEQUENCE: 250

Tyr Ala Tyr Gly Gly Leu Tyr Gly Gly Tyr Gly Leu Gly Ala Tyr Gly
1               5                   10                  15

Tyr

<210> SEQ ID NO 251
<211> LENGTH: 17
<212> TYPE: PRT
<213> ORGANISM: Loligo vulgaris

<400> SEQUENCE: 251

Val Gly Tyr Ala Gly Tyr Gly Leu Gly Leu Tyr Gly Ala Gly Tyr His
1               5                   10                  15

Tyr

<210> SEQ ID NO 252
<211> LENGTH: 17
<212> TYPE: PRT
<213> ORGANISM: Loligo vulgaris

<400> SEQUENCE: 252

Tyr Ala Tyr Gly Gly Leu Tyr Gly Gly Tyr Gly Leu Gly Ala Tyr Gly
1               5                   10                  15

Tyr

<210> SEQ ID NO 253
<211> LENGTH: 50
<212> TYPE: PRT
<213> ORGANISM: Loligo vulgaris

<400> SEQUENCE: 253

Val Gly Tyr Ala Gly Tyr Gly Leu Gly Ala Tyr Gly Gly Tyr Ala Gly
1               5                   10                  15

Tyr Gly Leu Gly Ala Phe Gly Gly Tyr Ala Gly Tyr Gly Leu Gly Ala
                20                  25                  30

Phe Gly Gly Tyr Ala Gly Leu Gly Leu Gly Leu Tyr Gly Ala Gly Tyr
            35                  40                  45

His Tyr

<210> SEQ ID NO 254
<211> LENGTH: 42
<212> TYPE: PRT
<213> ORGANISM: Loligo vulgaris

<400> SEQUENCE: 254

Leu Gly Phe Gly Gly Leu Leu Gly Gly Tyr Gly Gly Leu His His Gly
1               5                   10                  15

Val Tyr Gly Leu Gly Gly Tyr Gly Gly Leu Tyr Gly Tyr Gly Leu
            20                  25                  30

Gly Gly Tyr Gly Leu His Gly Leu His Tyr
        35                  40

<210> SEQ ID NO 255
<211> LENGTH: 58
<212> TYPE: PRT
<213> ORGANISM: Loligo vulgaris

<400> SEQUENCE: 255

Leu Gly Phe Gly Gly Val Leu Gly Tyr Gly Gly Leu His His Gly Val
1               5                   10                  15

Tyr Gly Leu Gly Gly Tyr Gly Gly Leu His Gly Ala Tyr Gly Leu Gly
            20                  25                  30

Gly Tyr Gly Gly Leu His Gly Ala Tyr Gly Leu Gly Tyr Gly Gly
        35                  40                  45

Leu Tyr Gly Gly Tyr Gly Leu Gly Gly His
    50                  55

<210> SEQ ID NO 256
<211> LENGTH: 58
<212> TYPE: PRT
<213> ORGANISM: Loligo vulgaris

<400> SEQUENCE: 256

Val Gly Tyr Gly Gly Tyr Gly Tyr Gly Leu Gly Ala Tyr Gly His
1               5                   10                  15

Tyr Gly Gly Tyr Gly Leu Gly Gly Leu Tyr Gly Gly Tyr Gly Leu Gly
            20                  25                  30

Gly Ala Tyr Gly Gly Tyr Gly Leu Gly Gly Tyr Gly Gly Tyr Gly
        35                  40                  45

Val Gly Val His Ser Arg Tyr Gly Val Gly
    50                  55

<210> SEQ ID NO 257
<211> LENGTH: 15
<212> TYPE: PRT
<213> ORGANISM: Loligo vulgaris

<400> SEQUENCE: 257

Gly Tyr Gly Tyr Gly Gly Leu Leu Gly Tyr Gly Leu His Tyr
1               5                   10                  15

<210> SEQ ID NO 258
<211> LENGTH: 29
<212> TYPE: PRT
<213> ORGANISM: Loligo vulgaris

<400> SEQUENCE: 258

Tyr Gly Tyr Gly Leu Ala Gly Tyr Gly Gly Leu Tyr Gly Gly Leu His

<210> SEQ ID NO 259
<211> LENGTH: 38
<212> TYPE: PRT
<213> ORGANISM: Loligo vulgaris

<400> SEQUENCE: 259

Leu Gly Tyr Gly Leu Ala Gly Tyr Gly Gly Leu Tyr Gly Gly Leu Tyr
1               5                   10                  15

Gly Gly His Gly Leu Gly Gly Tyr Gly Gly Val Tyr Gly Gly Tyr Gly
            20                  25                  30

Leu His Gly Leu His Tyr
        35

<210> SEQ ID NO 260
<211> LENGTH: 14
<212> TYPE: PRT
<213> ORGANISM: Loligo vulgaris

<400> SEQUENCE: 260

Leu Gly Phe Gly Gly Val Leu Gly Tyr Gly Gly Leu His His
1               5                   10

<210> SEQ ID NO 261
<211> LENGTH: 57
<212> TYPE: PRT
<213> ORGANISM: Loligo vulgaris

<400> SEQUENCE: 261

Gly Val Tyr Gly Leu Gly His Gly Ala Tyr Leu Gly Gly Tyr Gly
1               5                   10                  15

Gly Leu His Gly Ala Tyr Gly Leu Gly Gly Tyr Gly Gly Leu Tyr Gly
            20                  25                  30

Gly Tyr Gly Leu Gly Gly Tyr Gly Ala Leu His Gly Gly Leu Tyr Gly
        35                  40                  45

Gly Tyr Gly Leu Gly Gly Gly Leu Leu
            50                  55

<210> SEQ ID NO 262
<211> LENGTH: 17
<212> TYPE: PRT
<213> ORGANISM: Loligo vulgaris

<400> SEQUENCE: 262

Tyr Ser Tyr Gly Gly Leu Val Gly Gly Tyr Gly Gly Leu Tyr His His
1               5                   10                  15

Ala

<210> SEQ ID NO 263
<211> LENGTH: 48
<212> TYPE: PRT
<213> ORGANISM: Loligo vulgaris

<400> SEQUENCE: 263

Leu Phe Gly Gly Ile Leu Gly Gly Tyr Gly Gly Val Leu Ala Gly Tyr
1               5                   10                  15

Gly Gly Leu His His Gly Ala Tyr Gly Leu Gly Gly Tyr Gly Gly Leu
            20                  25                  30

Tyr Gly Gly Tyr Gly Leu Gly Gly Tyr Gly Leu His Gly Leu His Tyr
        35                  40                  45

<210> SEQ ID NO 264
<211> LENGTH: 57
<212> TYPE: PRT
<213> ORGANISM: Loligo vulgaris

<400> SEQUENCE: 264

Leu Gly Phe Gly Gly Val Leu Gly Tyr Gly Leu His His Gly Val
1               5                   10                  15

Tyr Gly Leu Gly Gly Tyr Gly Gly Leu His Gly Ala Tyr Gly Leu Gly
            20                  25                  30

Gly Tyr Gly Gly Leu His Gly Ala Tyr Gly Leu Gly Gly Tyr Gly Gly
        35                  40                  45

Leu Tyr Gly Gly Thr Leu Ser Thr Leu
    50                  55

<210> SEQ ID NO 265
<211> LENGTH: 16
<212> TYPE: PRT
<213> ORGANISM: Loligo vulgaris

<400> SEQUENCE: 265

Gly Tyr Gly Tyr Gly Gly Leu Leu Gly Gly Leu Gly His Ala Val Gly
1               5                   10                  15

<210> SEQ ID NO 266
<211> LENGTH: 27
<212> TYPE: PRT
<213> ORGANISM: Loligo vulgaris

<400> SEQUENCE: 266

Val Gly Tyr Gly Tyr Gly Gly Leu Leu Gly Gly Tyr Gly Gly Leu Tyr
1               5                   10                  15

Gly Gly Trp Gly Gly Val Tyr Gly Gly Leu Gly
            20                  25

<210> SEQ ID NO 267
<211> LENGTH: 21
<212> TYPE: PRT
<213> ORGANISM: Loligo vulgaris

<400> SEQUENCE: 267

Val Gly Tyr Gly Tyr Gly Gly Phe Leu Gly Gly Tyr Gly Leu Gly Val
1               5                   10                  15

Tyr Gly His Gly Tyr
            20

<210> SEQ ID NO 268
<211> LENGTH: 38
<212> TYPE: PRT
<213> ORGANISM: Loligo vulgaris

<400> SEQUENCE: 268

Leu Gly Tyr Gly Leu Ala Gly Tyr Gly Gly Leu Tyr Gly Gly Leu Tyr
1               5                   10                  15

Gly Gly His Gly Leu Gly Gly Tyr Gly Gly Val Tyr Gly Gly Tyr Gly
            20                  25                  30

Leu His Gly Leu His Tyr
        35

<210> SEQ ID NO 269
<211> LENGTH: 75
<212> TYPE: PRT
<213> ORGANISM: Loligo vulgaris

<400> SEQUENCE: 269

Leu Gly Phe Gly Gly Val Leu Gly Tyr Gly Leu His His Gly Val
1               5                   10                  15

Tyr Gly Leu Gly Gly Tyr Gly Gly Leu His Gly Ala Tyr Gly Leu Gly
            20                  25                  30

Gly Tyr Gly Gly Leu His Gly Ala Tyr Gly Leu Gly Gly Tyr Gly Gly
        35                  40                  45

Leu Tyr Gly Gly Tyr Gly Leu Gly Gly Tyr Gly Ala Leu His Gly Gly
    50                  55                  60

Leu Tyr Gly Gly Tyr Gly Leu Gly Gly Leu
65                  70                  75

<210> SEQ ID NO 270
<211> LENGTH: 15
<212> TYPE: PRT
<213> ORGANISM: Loligo vulgaris

<400> SEQUENCE: 270

Gly Tyr Gly Tyr Gly Gly Leu Leu Gly Gly Tyr Gly Leu His Tyr
1               5                   10                  15

<210> SEQ ID NO 271
<211> LENGTH: 24
<212> TYPE: PRT
<213> ORGANISM: Loligo vulgaris

<400> SEQUENCE: 271

Tyr Gly Tyr Gly Leu Ala Gly Tyr Gly Gly Leu Tyr Gly Gly Tyr Gly
1               5                   10                  15

Leu Gly Gly Tyr Gly Leu Gly Tyr
            20

<210> SEQ ID NO 272
<211> LENGTH: 38
<212> TYPE: PRT
<213> ORGANISM: Loligo vulgaris

<400> SEQUENCE: 272

Leu Gly Tyr Gly Leu Ala Gly Tyr Gly Gly Leu Tyr Gly Gly Leu Tyr
1               5                   10                  15

Gly Gly His Gly Leu Gly Gly Tyr Gly Gly Val Tyr Gly Gly Tyr Gly
            20                  25                  30

Leu His Gly Leu His Tyr
        35

<210> SEQ ID NO 273
<211> LENGTH: 47
<212> TYPE: PRT
<213> ORGANISM: Loligo vulgaris

<400> SEQUENCE: 273

Leu Gly Phe Gly Gly Val Leu Gly Tyr Gly Gly Leu His His Gly Val
1               5                   10                  15

Tyr Gly Leu Gly Gly Tyr Gly Gly Leu His Gly Ala Tyr Gly Leu Gly
            20                  25                  30

Gly Tyr Gly Leu Gly Gly Phe His Gly Gly Tyr Gly Leu Gly Gly
            35                  40                  45

<210> SEQ ID NO 274
<211> LENGTH: 27
<212> TYPE: PRT
<213> ORGANISM: Loligo vulgaris

<400> SEQUENCE: 274

Val Gly Leu Gly Leu Gly Gly Phe His Gly Gly Tyr Gly Phe Gly Gly
1               5                   10                  15

Tyr Gly Leu Gly Gly Phe His Gly Gly Tyr Gly
            20                  25

<210> SEQ ID NO 275
<211> LENGTH: 38
<212> TYPE: PRT
<213> ORGANISM: Loligo vulgaris

<400> SEQUENCE: 275

Val Gly Phe Gly Gly Tyr Gly Tyr Gly Gly Ile Gly Gly Leu Tyr Gly
1               5                   10                  15

Gly His Tyr Gly Gly Tyr Gly Leu Gly Gly Ala Tyr Gly His Tyr Gly
            20                  25                  30

Gly Tyr Gly Leu Gly Gly
        35

<210> SEQ ID NO 276
<211> LENGTH: 16
<212> TYPE: PRT
<213> ORGANISM: Loligo vulgaris

<400> SEQUENCE: 276

Gly Tyr Gly Tyr Gly Gly Leu Leu Gly Gly Leu Gly His Ala Val Gly
1               5                   10                  15

<210> SEQ ID NO 277
<211> LENGTH: 26
<212> TYPE: PRT
<213> ORGANISM: Loligo vulgaris

<400> SEQUENCE: 277

Gly Tyr Gly Tyr Gly Gly Leu Leu Gly Gly Tyr Gly Gly Leu Tyr Gly
1               5                   10                  15

Gly Trp Gly Gly Val Tyr Gly Gly Leu Gly
            20                  25

<210> SEQ ID NO 278
<211> LENGTH: 21
<212> TYPE: PRT
<213> ORGANISM: Loligo vulgaris

<400> SEQUENCE: 278

Val Gly Tyr Gly Tyr Gly Gly Phe Leu Gly Gly Tyr Gly Leu Gly Val
1               5                   10                  15

Tyr Gly His Gly Tyr
            20

<210> SEQ ID NO 279
<211> LENGTH: 26
<212> TYPE: PRT
<213> ORGANISM: Loligo vulgaris

<400> SEQUENCE: 279

Leu Gly Tyr Gly Gly Leu Leu Gly Gly Tyr Gly Gly Leu Tyr Gly Gly
1               5                   10                  15

Tyr Gly Leu Gly Gly Tyr Gly Leu Gly Tyr
            20                  25

<210> SEQ ID NO 280
<211> LENGTH: 17
<212> TYPE: PRT
<213> ORGANISM: Loligo vulgaris

<400> SEQUENCE: 280

Tyr Gly Tyr Gly Leu Ala Gly Tyr Gly Gly Leu Tyr Gly Gly Leu Leu
1               5                   10                  15

His

<210> SEQ ID NO 281
<211> LENGTH: 38
<212> TYPE: PRT
<213> ORGANISM: Loligo vulgaris

<400> SEQUENCE: 281

Leu Gly Tyr Gly Leu Ala Gly Tyr Gly Gly Leu Tyr Gly Gly Leu Tyr
1               5                   10                  15

Gly Gly His Gly Leu Gly Tyr Gly Val Tyr Gly Tyr Gly
            20                  25                  30

Leu His Gly Leu His Tyr
        35

<210> SEQ ID NO 282
<211> LENGTH: 52
<212> TYPE: PRT
<213> ORGANISM: Loligo vulgaris

<400> SEQUENCE: 282

Leu Gly Phe Gly Gly Val Leu Gly Tyr Gly Gly Leu His His Gly Ala
1               5                   10                  15

Tyr Gly Leu Gly Gly Tyr Gly Gly Leu Tyr Gly Gly Tyr Gly Leu Gly
            20                  25                  30

Gly Tyr Gly Gly Leu Tyr Gly Gly Tyr Gly Ala Leu His Gly Gly Tyr
        35                  40                  45

Gly Leu Gly Tyr
    50

<210> SEQ ID NO 283
<211> LENGTH: 15
<212> TYPE: PRT
<213> ORGANISM: Loligo vulgaris

<400> SEQUENCE: 283

Tyr Gly Leu Ala Gly Tyr Gly Gly Leu Tyr Gly Gly Leu Leu His
1               5                   10                  15

<210> SEQ ID NO 284
<211> LENGTH: 21
<212> TYPE: PRT
<213> ORGANISM: Loligo vulgaris

<400> SEQUENCE: 284

Thr Ala Leu Gly Tyr Gly Gly Leu Tyr Gly Gly Tyr Gly Leu Gly Ala

```
Tyr Gly Leu Gly Tyr
            20

<210> SEQ ID NO 285
<211> LENGTH: 26
<212> TYPE: PRT
<213> ORGANISM: Loligo vulgaris

<400> SEQUENCE: 285

Leu Gly Tyr Gly Gly Leu Leu Gly Gly Tyr Gly Gly Leu Tyr Gly Arg
1               5                   10                  15

Tyr Gly Val Gly Gly Tyr Gly Leu Gly Tyr
            20                  25

<210> SEQ ID NO 286
<211> LENGTH: 19
<212> TYPE: PRT
<213> ORGANISM: Loligo vulgaris

<400> SEQUENCE: 286

Gly Gly Tyr Gly Ser Leu Leu Gly Gly His Gly Gly Leu Tyr Gly Gly
1               5                   10                  15

Leu Gly Leu

<210> SEQ ID NO 287
<211> LENGTH: 13
<212> TYPE: PRT
<213> ORGANISM: Loligo vulgaris

<400> SEQUENCE: 287

Tyr Gly Tyr Gly Gly Val Leu Gly Gly Tyr Gly Gln Gly
1               5                   10

<210> SEQ ID NO 288
<211> LENGTH: 19
<212> TYPE: PRT
<213> ORGANISM: Loligo vulgaris

<400> SEQUENCE: 288

Leu Gly Tyr Gly Gly Leu Leu Gly Gly Tyr Gly Gly Leu His His Gly
1               5                   10                  15

Val Tyr Gly

<210> SEQ ID NO 289
<211> LENGTH: 39
<212> TYPE: PRT
<213> ORGANISM: Loligo vulgaris

<400> SEQUENCE: 289

Gly Gly Tyr Gly Gly Leu Tyr Gly Gly Tyr Gly Leu Gly Gly Tyr Gly
1               5                   10                  15

Gly Leu His Gly Ala Tyr Gly Leu Gly Gly Tyr Gly Gly Val Tyr Gly
            20                  25                  30

Gly Tyr Gly Leu Gly Gly His
            35

<210> SEQ ID NO 290
<211> LENGTH: 30
<212> TYPE: PRT
<213> ORGANISM: Loligo vulgaris
```

-continued

```
<400> SEQUENCE: 290

Val Gly Tyr Gly Tyr Gly Tyr Gly Leu Gly Ala Tyr Gly His
1               5                   10                  15

Tyr Gly Gly Tyr Gly Leu Gly Gly Leu Tyr Gly Gly Tyr Gly
            20                  25                  30

<210> SEQ ID NO 291
<211> LENGTH: 27
<212> TYPE: PRT
<213> ORGANISM: Loligo vulgaris

<400> SEQUENCE: 291

Val Gly Tyr Gly Tyr Gly Gly Leu Leu Gly Tyr Gly Gly Leu Tyr
1               5                   10                  15

Gly Gly Trp Gly Gly Val Tyr Gly Gly Leu Gly
            20                  25

<210> SEQ ID NO 292
<211> LENGTH: 21
<212> TYPE: PRT
<213> ORGANISM: Loligo vulgaris

<400> SEQUENCE: 292

Val Gly Tyr Gly Tyr Gly Gly Phe Leu Gly Tyr Gly Leu Gly Val
1               5                   10                  15

Tyr Gly His Gly Tyr
            20

<210> SEQ ID NO 293
<211> LENGTH: 38
<212> TYPE: PRT
<213> ORGANISM: Loligo vulgaris

<400> SEQUENCE: 293

Leu Gly Tyr Gly Leu Ala Gly Tyr Gly Gly Leu Tyr Gly Gly Leu Tyr
1               5                   10                  15

Gly Gly His Gly Leu Gly Gly Tyr Gly Gly Val Tyr Gly Gly Tyr Gly
            20                  25                  30

Leu His Gly Leu His Tyr
        35

<210> SEQ ID NO 294
<211> LENGTH: 46
<212> TYPE: PRT
<213> ORGANISM: Loligo vulgaris

<400> SEQUENCE: 294

Leu Gly Phe Gly Gly Val Leu Gly Tyr Gly Leu His His Gly Val
1               5                   10                  15

Tyr Gly Leu Gly Gly Tyr Gly Gly Leu His Gly Ala Tyr Gly Leu Gly
            20                  25                  30

Gly Tyr Gly Gly Leu Tyr Gly Gly Tyr Gly Leu Gly Gly His
        35                  40                  45

<210> SEQ ID NO 295
<211> LENGTH: 10
<212> TYPE: PRT
<213> ORGANISM: Loligo vulgaris

<400> SEQUENCE: 295

Val Tyr Gly Gly Tyr Gly Leu Gly Gly His
```

<210> SEQ ID NO 296
<211> LENGTH: 33
<212> TYPE: PRT
<213> ORGANISM: Loligo vulgaris

<400> SEQUENCE: 296

Val Gly Tyr Gly Gly Tyr Gly Tyr Gly Gly Leu Tyr Gly His
1               5                   10                  15

Tyr Gly Gly Tyr Gly His Phe Gly Gly Val His Ser His Tyr Gly Val
                20                  25                  30

Gly

<210> SEQ ID NO 297
<211> LENGTH: 19
<212> TYPE: PRT
<213> ORGANISM: Loligo vulgaris

<400> SEQUENCE: 297

Tyr Gly Asp Val Tyr Gly Gly Leu Tyr Gly Gly Leu Tyr Gly Leu
1               5                   10                  15

Leu Gly Ala

<210> SEQ ID NO 298
<211> LENGTH: 28
<212> TYPE: PRT
<213> ORGANISM: Loligo vulgaris

<400> SEQUENCE: 298

Leu Gly Tyr Gly Gly Leu Leu Gly Gly Tyr Gly Ala Leu His Gly Gly
1               5                   10                  15

Leu Tyr Gly Gly Tyr Gly Leu Gly Gly Leu His Tyr
                20                  25

<210> SEQ ID NO 299
<211> LENGTH: 199
<212> TYPE: PRT
<213> ORGANISM: artificial sequence
<220> FEATURE:
<223> OTHER INFORMATION: Recombinant protein

<400> SEQUENCE: 299

Met Thr Tyr Gly Tyr Gly Gly Leu Tyr Gly Gly Leu Tyr Gly Gly Leu
1               5                   10                  15

Gly Tyr Pro Ala Ala Ala Ser Val Ser Thr Val His His Pro Tyr Gly
                20                  25                  30

Tyr Gly Gly Leu Tyr Gly Gly Leu Tyr Gly Gly Leu Gly Tyr Pro Ala
            35                  40                  45

Ala Ala Ser Val Ser Thr Val His His Pro Tyr Gly Tyr Gly Gly Leu
        50                  55                  60

Tyr Gly Gly Leu Tyr Gly Gly Leu Gly Tyr Pro Ala Ala Ala Ser Val
65                  70                  75                  80

Ser Thr Val His His Pro Tyr Gly Tyr Gly Gly Leu Tyr Gly Gly Leu
                85                  90                  95

Tyr Gly Gly Leu Gly Tyr Pro Ala Ala Ala Ser Val Ser Thr Val His
                100                 105                 110

His Pro Tyr Gly Tyr Gly Gly Leu Tyr Gly Gly Leu Tyr Gly Gly Leu
            115                 120                 125

```
Gly Tyr Pro Ala Ala Ala Ser Val Ser Thr Val His His Pro Tyr Gly
    130                 135                 140

Tyr Gly Gly Leu Tyr Gly Gly Leu Tyr Gly Gly Leu Tyr Gly Pro Ala
145                 150                 155                 160

Ala Ala Ser Val Ser Thr Val His His Pro Tyr Gly Tyr Gly Gly Leu
            165                 170                 175

Tyr Gly Gly Leu Tyr Gly Gly Leu Gly Tyr Pro Ala Ala Ala Ser Val
            180                 185                 190

Ser Thr Val His His Pro Ser
            195
```

```
<210> SEQ ID NO 300
<211> LENGTH: 163
<212> TYPE: PRT
<213> ORGANISM: artificial sequence
<220> FEATURE:
<223> OTHER INFORMATION: Recombinant protein

<400> SEQUENCE: 300

Met Gly Thr Leu Ser Tyr Gly Tyr Gly Gly Leu Tyr Gly Gly Leu Tyr
1               5                   10                  15

Gly Gly Leu Gly Tyr Gly Pro Ala Ala Ala Ser Val Ser Thr Val His
            20                  25                  30

His Pro Ser Thr Gly Thr Leu Ser Tyr Gly Tyr Gly Gly Leu Tyr Gly
            35                  40                  45

Gly Leu Tyr Gly Gly Leu Gly Tyr Gly Pro Ala Ala Ala Ser Val Ser
        50                  55                  60

Thr Val His His Pro Ser Thr Gly Thr Leu Ser Tyr Gly Tyr Gly Gly
65                  70                  75                  80

Leu Tyr Gly Gly Leu Tyr Gly Gly Leu Gly Tyr Gly Pro Ala Ala Ala
                85                  90                  95

Ser Val Ser Thr Val His His Pro Ser Thr Gly Thr Leu Ser Tyr Gly
            100                 105                 110

Tyr Gly Gly Leu Tyr Gly Gly Leu Tyr Gly Gly Leu Gly Tyr Gly Pro
            115                 120                 125

Ala Ala Ala Ser Val Ser Thr Val His His Pro Ser Thr Gly Thr Leu
        130                 135                 140

Ser Tyr Gly Tyr Gly Gly Leu Tyr Gly Gly Leu Tyr Gly Gly Leu Gly
145                 150                 155                 160

Tyr Gly Pro
```

```
<210> SEQ ID NO 301
<211> LENGTH: 268
<212> TYPE: PRT
<213> ORGANISM: artificial sequence
<220> FEATURE:
<223> OTHER INFORMATION: Recombinant protein

<400> SEQUENCE: 301

Met Gly Thr Leu Ser Tyr Gly Tyr Gly Gly Leu Tyr Gly Gly Leu Tyr
1               5                   10                  15

Gly Gly Leu Gly Tyr Gly Pro Ala Ala Ala Ser Val Ser Thr Val His
            20                  25                  30

His Pro Ser Thr Gly Thr Leu Ser Tyr Gly Tyr Gly Gly Leu Tyr Gly
            35                  40                  45

Gly Leu Tyr Gly Gly Leu Gly Tyr Gly Pro Ala Ala Ala Ser Val Ser
        50                  55                  60
```

Thr Val His His Pro Ser Thr Gly Thr Leu Ser Tyr Gly Tyr Gly
65              70                  75                  80

Leu Tyr Gly Gly Leu Tyr Gly Gly Leu Gly Tyr Gly Pro Ala Ala Ala
                85                  90                  95

Ser Val Ser Thr Val His His Pro Ser Thr Gly Thr Leu Ser Tyr Gly
            100                 105                 110

Tyr Gly Gly Leu Tyr Gly Gly Leu Tyr Gly Gly Leu Gly Tyr Gly Pro
            115                 120                 125

Ala Ala Ala Ser Val Ser Thr Val His His Pro Ser Thr Gly Thr Leu
        130                 135                 140

Ser Tyr Gly Tyr Gly Gly Leu Tyr Gly Gly Leu Tyr Gly Gly Leu Gly
145                 150                 155                 160

Tyr Gly Pro Ala Ala Ala Ser Val Ser Thr Val His His Pro Ser Thr
                165                 170                 175

Gly Thr Leu Ser Tyr Gly Tyr Gly Gly Leu Tyr Gly Gly Leu Tyr Gly
            180                 185                 190

Gly Leu Gly Tyr Gly Pro Ala Ala Ala Ser Val Ser Thr Val His His
            195                 200                 205

Pro Ser Thr Gly Thr Leu Ser Tyr Gly Tyr Gly Gly Leu Tyr Gly Gly
210                 215                 220

Leu Tyr Gly Gly Leu Gly Tyr Gly Pro Ala Ala Ala Ser Val Ser Thr
225                 230                 235                 240

Val His His Pro Ser Thr Gly Thr Leu Ser Tyr Gly Tyr Gly Gly Leu
                245                 250                 255

Tyr Gly Gly Leu Tyr Gly Gly Leu Gly Tyr Gly Pro
            260                 265

<210> SEQ ID NO 302
<211> LENGTH: 443
<212> TYPE: PRT
<213> ORGANISM: artificial sequence
<220> FEATURE:
<223> OTHER INFORMATION: Recombinant protein

<400> SEQUENCE: 302

Met Gly Thr Leu Ser Tyr Gly Tyr Gly Gly Leu Tyr Gly Gly Leu Tyr
1               5                   10                  15

Gly Gly Leu Gly Tyr Gly Pro Ala Ala Ala Ser Val Ser Thr Val His
            20                  25                  30

His Pro Ser Thr Gly Thr Leu Ser Tyr Gly Tyr Gly Gly Leu Tyr Gly
        35                  40                  45

Gly Leu Tyr Gly Gly Leu Gly Tyr Gly Pro Ala Ala Ala Ser Val Ser
    50                  55                  60

Thr Val His His Pro Ser Thr Gly Thr Leu Ser Tyr Gly Tyr Gly Gly
65              70                  75                  80

Leu Tyr Gly Gly Leu Tyr Gly Gly Leu Gly Tyr Gly Pro Ala Ala Ala
                85                  90                  95

Ser Val Ser Thr Val His His Pro Ser Thr Gly Thr Leu Ser Tyr Gly
            100                 105                 110

Tyr Gly Gly Leu Tyr Gly Gly Leu Tyr Gly Gly Leu Gly Tyr Gly Pro
            115                 120                 125

Ala Ala Ala Ser Val Ser Thr Val His His Pro Ser Thr Gly Thr Leu
        130                 135                 140

Ser Tyr Gly Tyr Gly Gly Leu Tyr Gly Gly Leu Tyr Gly Gly Leu Gly
145                 150                 155                 160

```
Tyr Gly Pro Ala Ala Ala Ser Val Ser Thr Val His His Pro Ser Thr
            165                 170                 175

Gly Thr Leu Ser Tyr Gly Tyr Gly Gly Leu Tyr Gly Gly Leu Tyr Gly
            180                 185                 190

Gly Leu Gly Tyr Gly Pro Ala Ala Ser Val Ser Thr Val His His
            195                 200                 205

Pro Ser Thr Gly Thr Leu Ser Tyr Gly Tyr Gly Gly Leu Tyr Gly Gly
            210                 215                 220

Leu Tyr Gly Gly Leu Tyr Gly Pro Ala Ala Ser Val Ser Thr
225                 230                 235                 240

Val His His Pro Ser Thr Gly Thr Leu Ser Tyr Gly Tyr Gly Gly Leu
            245                 250                 255

Tyr Gly Gly Leu Tyr Gly Gly Leu Gly Tyr Gly Pro Ala Ala Ala Ser
            260                 265                 270

Val Ser Thr Val His His Pro Ser Thr Gly Thr Leu Ser Tyr Gly Tyr
            275                 280                 285

Gly Gly Leu Tyr Gly Gly Leu Tyr Gly Gly Leu Gly Tyr Gly Pro Ala
            290                 295                 300

Ala Ala Ser Val Ser Thr Val His His Pro Ser Thr Gly Thr Leu Ser
305                 310                 315                 320

Tyr Gly Tyr Gly Gly Leu Tyr Gly Gly Leu Tyr Gly Gly Leu Gly Tyr
            325                 330                 335

Gly Pro Ala Ala Ala Ser Val Ser Thr Val His His Pro Ser Thr Gly
            340                 345                 350

Thr Leu Ser Tyr Gly Tyr Gly Gly Leu Tyr Gly Gly Leu Tyr Gly Gly
            355                 360                 365

Leu Gly Tyr Gly Pro Ala Ala Ala Ser Val Ser Thr Val His His Pro
            370                 375                 380

Ser Thr Gly Thr Leu Ser Tyr Gly Tyr Gly Gly Leu Tyr Gly Gly Leu
385                 390                 395                 400

Tyr Gly Gly Leu Gly Tyr Gly Pro Ala Ala Ala Ser Val Ser Thr Val
            405                 410                 415

His His Pro Ser Thr Gly Thr Leu Ser Tyr Gly Tyr Gly Gly Leu Tyr
            420                 425                 430

Gly Gly Leu Tyr Gly Gly Leu Gly Tyr Gly Pro
            435                 440

<210> SEQ ID NO 303
<211> LENGTH: 195
<212> TYPE: PRT
<213> ORGANISM: Loligo vulgaris

<400> SEQUENCE: 303

Met Ala Ala Lys Leu Ile Thr Leu Leu Ala Val Ile Ala Leu Ser Asn
1               5                   10                  15

Tyr Ala Tyr Ala Leu Leu Pro Gly Leu Leu Gly Gly Tyr Gly Tyr Pro
            20                  25                  30

Ala Ala Thr Thr Tyr Arg Gln Thr Thr His His Gly Tyr Gly Gly Leu
            35                  40                  45

Tyr Gly Gly Leu Gly Tyr His Tyr Pro Ala Ala Thr Ala Val Ser His
            50                  55                  60

Thr Thr His His Ala Pro Tyr Gly Tyr Gly Leu Tyr Gly Leu
65                  70                  75                  80

Tyr Gly Gly Leu Gly Tyr Pro Ala Ala Ala Ser Val Ser Thr Val His
            85                  90                  95
```

His Pro Val Gly Tyr Gly Gly Tyr Gly Leu Gly Ala Tyr Gly Ala Tyr
                100                 105                 110

Gly Leu Gly Tyr Gly Leu His Tyr Pro Ala Ala Thr Ala Val Ser His
            115                 120                 125

Thr Thr His His Ala Pro Tyr Gly Tyr Gly Leu Tyr Gly Gly Leu
130                 135                 140

Tyr Gly Gly Leu Gly Ala Val Ser Thr Val Ser His Gly Leu Gly Tyr
145                 150                 155                 160

Gly Leu His His Pro Val Gly Tyr Ala Gly Tyr Gly Leu Gly Ala Thr
                165                 170                 175

Ala Val Ser His Thr Thr His His Ala Pro Tyr Gly Gly Phe Gly Tyr
            180                 185                 190

Gly Leu Tyr
        195

<210> SEQ ID NO 304
<211> LENGTH: 28
<212> TYPE: PRT
<213> ORGANISM: Loligo vulgaris

<400> SEQUENCE: 304

Tyr Gly Tyr Gly Gly Leu Tyr Gly Gly Leu Tyr Gly Gly Leu Gly Tyr
1               5                   10                  15

Pro Ala Ala Ala Ser Val Ser Thr Val His His Pro
            20                  25

<210> SEQ ID NO 305
<211> LENGTH: 12
<212> TYPE: PRT
<213> ORGANISM: artificial sequence
<220> FEATURE:
<223> OTHER INFORMATION: Protein

<400> SEQUENCE: 305

Pro Ala Ala Ala Ala Ala Ala Ala Val His His Pro
1               5                   10

<210> SEQ ID NO 306
<211> LENGTH: 12
<212> TYPE: PRT
<213> ORGANISM: artificial sequence
<220> FEATURE:
<223> OTHER INFORMATION: Protein

<400> SEQUENCE: 306

Pro Ala Ala Ala Pro Val Ala Pro Val His His Pro
1               5                   10

<210> SEQ ID NO 307
<211> LENGTH: 12
<212> TYPE: PRT
<213> ORGANISM: artificial sequence
<220> FEATURE:
<223> OTHER INFORMATION: Protein

<400> SEQUENCE: 307

Pro Ala Ala Ala Ser Val Ser Thr Val His His Pro
1               5                   10

<210> SEQ ID NO 308
<211> LENGTH: 12
<212> TYPE: PRT

```
<213> ORGANISM: artificial sequence
<220> FEATURE:
<223> OTHER INFORMATION: Protein

<400> SEQUENCE: 308

Pro Ala Ala Ala Ala Leu Pro Ala Val His His Pro
1               5                   10

<210> SEQ ID NO 309
<211> LENGTH: 12
<212> TYPE: PRT
<213> ORGANISM: artificial sequence
<220> FEATURE:
<223> OTHER INFORMATION: Protein

<400> SEQUENCE: 309

Pro Ala Ala Ala Pro Leu Ser Thr Val His His Pro
1               5                   10

<210> SEQ ID NO 310
<211> LENGTH: 37
<212> TYPE: PRT
<213> ORGANISM: artificial sequence
<220> FEATURE:
<223> OTHER INFORMATION: Protein

<400> SEQUENCE: 310

Ser Thr Gly Thr Leu Ser Tyr Gly Tyr Gly Leu Tyr Gly Gly Leu
1               5                   10                  15

Tyr Gly Gly Leu Gly Tyr Gly Pro Ala Ala Ala Ser Val Ser Thr Val
                20                  25                  30

His His Pro Ser Thr
        35

<210> SEQ ID NO 311
<211> LENGTH: 111
<212> TYPE: DNA
<213> ORGANISM: artificial sequence
<220> FEATURE:
<223> OTHER INFORMATION: Synthetic DNA

<400> SEQUENCE: 311
agtactggta ccctcagcta tggctatggt ggcctatatg gaggactgta cggtggtctg      60
ggttacgggc ccgctgccgc aagcgtgagt accgtgcatc atccgagtac t              111

<210> SEQ ID NO 312
<211> LENGTH: 80
<212> TYPE: DNA
<213> ORGANISM: artificial sequence
<220> FEATURE:
<223> OTHER INFORMATION: Synthetic DNA

<400> SEQUENCE: 312
ggatatacct cctgacatgc caccagaccc aatgcccggg cgacggcgtt cgcactcatg      60
gcacgtagta aggctcatga                                                 80
```